United States Patent
Chua et al.

(10) Patent No.: US 12,098,407 B2
(45) Date of Patent: Sep. 24, 2024

(54) METHODS FOR DECOUPLING YIELD AND PRODUCTIVITY OF A NON-CATABOLIC COMPOUND PRODUCED BY A HOST CELL

(71) Applicant: AMYRIS, INC., Emeryville, CA (US)

(72) Inventors: Penelope R. Chua, Emeryville, CA (US); Joshua Adam Lerman, Emeryville, CA (US); Thomas Jon Scherbart, Emeryville, CA (US); Chandresh Thakker, Emeryville, CA (US); Annie Ening Tsong, Emeryville, CA (US); Hanxiao Jiang, Emeryville, CA (US)

(73) Assignee: Amyris Inc., Emeryville, CA (US)

( * ) Notice: Subject to any disclaimer, the term of this patent is extended or adjusted under 35 U.S.C. 154(b) by 91 days.

(21) Appl. No.: 17/616,843

(22) PCT Filed: Jun. 5, 2020

(86) PCT No.: PCT/US2020/036417
§ 371 (c)(1),
(2) Date: Dec. 6, 2021

(87) PCT Pub. No.: WO2020/247816
PCT Pub. Date: Dec. 10, 2020

(65) Prior Publication Data
US 2022/0307059 A1    Sep. 29, 2022

Related U.S. Application Data

(60) Provisional application No. 63/034,883, filed on Jun. 4, 2020, provisional application No. 62/858,152, filed on Jun. 6, 2019.

(51) Int. Cl.
| | |
|---|---|
| *C12N 1/14* | (2006.01) |
| *C12N 1/18* | (2006.01) |
| *C12N 9/02* | (2006.01) |
| *C12N 9/14* | (2006.01) |
| *C12N 15/81* | (2006.01) |
| *C12P 5/00* | (2006.01) |

(52) U.S. Cl.
CPC .............. *C12P 5/007* (2013.01); *C12N 1/18* (2013.01); *C12N 9/0036* (2013.01); *C12N 9/14* (2013.01); *C12N 15/81* (2013.01)

(58) Field of Classification Search
CPC .......... C12N 1/18; C12N 9/0036; C12N 9/14; C12P 5/007
See application file for complete search history.

(56) References Cited

U.S. PATENT DOCUMENTS

| | | |
|---|---|---|
| 2004/0005678 A1 | 1/2004 | Keasling et al. |
| 2012/0088290 A1 | 4/2012 | Dmytruk et al. |
| 2013/0236942 A1 | 9/2013 | Stevens |
| 2015/0322461 A1 | 11/2015 | Semkiv et al. |
| 2016/0281112 A1 | 9/2016 | Calabria et al. |
| 2017/0283834 A1 | 10/2017 | Headman |

FOREIGN PATENT DOCUMENTS

| | | |
|---|---|---|
| JP | 2014-532444 | 12/2014 |
| WO | WO 2014/100526 | 6/2014 |
| WO | WO 2014/100726 | 6/2014 |
| WO | WO 2016/036648 | 3/2016 |

OTHER PUBLICATIONS

International Search Report from International Application No. PCT/US20/36417 mailed Nov. 16, 2020.
Anderson et al., "Biochemical Evidence that Starch Breakdown by *Bacteroides thetaiotaomicron* Involves Outer Membrane Starch-Binding Sites and Periplasmic Starch-Degrading Enzymes," J. Bacteriol, Jun. 1989, 171(12):6468-6472.
Beach et al., "Cloning, Sequencing, and Overexpression of mvaA, Which encodes *Pseudomonas mevalonii* 3-Hydroxy-3-Methylglutaryl Coenzyme A Reductase," J. Bacteriol, Jun. 1989, 171(6):2994-3001.
Bensch et al., "Purification and Properties of 3-Hydroxy-3-methylglutaryl Coenzyme A Reductase from *Pseudomonas*," J. Biol. Chem., Aug. 1970, 245(15):3755-3762.
Cregg et al., "*Pichia pastoris* as a Host System for Transformations," Mol. Cell. Biol., Dec. 1985, 5(12):3376-3385.
Fimognari et al., "Substrate-Competitive Inhibition of Bacterial Mevalonate: Nicotinamide-Adenine Dinucleotide Oxidoreductase (acylating CoA)*," Biochemistry, Oct. 1965, 4(10):2086-2090.
Genbank Accession No. AF529266, "*Zea mays* terpene synthase (tps1) mRNA, complete cds," Jan. 8, 2003, 2 pages.
Hinnen et al., "Transformation of yeast," Proc. Natl. Acad. Sci. USA, Apr. 1978, 75(4):1929-1933.
International Preliminary Report on Patentability in International Application No. PCT/US2020/036417, issued on Dec. 7, 2021, 8 pages.
Pechous et al., "Cloning and Functional Expression of an (E,E)-α-farnesene synthase cDNA from Peel Tissue of Apple Fruit," Planta, Jan. 2004, 219(1):84-94.
Picaud et al., "Expression, purification and characterization of recombinant (E)-β-farnesene synthase from *Artemisia annua*," Phytochemistry, May 2005, 66(9):961-967.
Sandoval et al., "Use of pantothenate as a metabolic switch increases the genetic stability of farnesene producing *Saccharomyces cerevisiae*," Metab Eng., Sep. 2014, 25:215-226.
Siddiqi et al., "Bacterial Metabolism of Mevalonic Acid conversion to acetoacetate," Biochem. Biophys. Res. Commun., Jun. 1962, 8(1-2):110-113.

(Continued)

*Primary Examiner* — Yong D Pak
(74) *Attorney, Agent, or Firm* — Fish & Richardson P.C.

(57) ABSTRACT

Provided herein are compositions and methods for uncoupling the yield and productivity of an isoprenoid compound produced in a host cell. In some embodiments, the yield and productivity are uncoupled by genetically modifying the host cell to reduce flux through the citric acid cycle (TCA). In other embodiments, the yield and productivity are uncoupled by reducing the levels of ATP in the host cell.

17 Claims, 10 Drawing Sheets

Specification includes a Sequence Listing.

(56) References Cited

OTHER PUBLICATIONS

Siddiqi et al., "Bacterial Metabolism of Mevalonic Acid," J. Bacteriol., Jan. 1967, 93(1):207-214.
Song, "A Soluble Form of Phosphatase in *Saccharomyces cerevisiae* Capable of Converting Farnesyl Diphosphate into E,E-Farnesol," Appl. Biochem. Biotechnol., Feb. 2006, 128:149-158.
Takatsuji et al., "Studies on Isoprenoid Biosynthesis with Bacterial Intact Cells," Biochem. Biophys. Res. Commun., Jan. 1983, 110(1):187-193.
Verduyn et al., "Effect of Benzoic Acid on Metabolic Fluxes in Yeasts: A Continuous-Culture Study on the Regulation of Respiration and Alcoholic Fermentation," Yeast, Jul. 1992, 8(7):501-517.
Meadows et al., "Rewriting yeast central carbon metabolism for industrial isoprenoid production," CLEO: Applications and Technology 2019, San Jose, California, May 5-10, 2019, 537(7622):694-697.
Pampulha et al., "Energetics of the Effect of Acetic Acid on Growth of *Saccharomyces cerevisiae*," FEMS Microbiology Letters, Mar. 2000, 184(1):69-72.
Supplementary European Search Report in European Application No. 20817816, dated Jan. 23, 2024, 13 pages.
Supplementary Partial European Search Report in European Application No. 20817816, dated Oct. 23, 2023, 15 pages.
Ullah et al., "Yeast Adaptation to Weak Acids Prevents Futile Energy Expenditure," Frontiers in Microbiology, Jun. 11, 2013, 4(142):1-10.

METHODS FOR DECOUPLING YIELD AND PRODUCTIVITY OF A NON-CATABOLIC COMPOUND PRODUCED BY A HOST CELL

CROSS-REFERENCE TO RELATED APPLICATION

This Application is the National Stage filing under 35 U.S.C. § 371 of PCT Application Ser. No. PCT/US20/36417 filed on Jun. 5, 2020, which claims the benefit of Provisional U.S. Application No. 62/858,152 filed on Jun. 6, 2019 and Provisional U.S. Application No. 63/034,883, filed Jun. 4, 2020. The disclosures of both applications are hereby incorporated herein by reference in their entireties.

BACKGROUND OF THE INVENTION

Yield and productivity are two major cost drivers for any biomanufacturing process. For the biomanufacturing of non-catabolic compounds like isoprenoids, productivity and yield are frequently a function of other cellular rates such as the rate of sugar and/or oxygen consumption. Design of fermentation processes that achieve the optimal combination of productivity and yield for the lowest cost production requires close characterization of this relationship. For the production of isoprenoids, under standard fermentation conditions, yield is consistently inversely correlated with the cell specific rates of oxygen and sugar uptake and by extension productivity, i.e. the faster oxygen and sugar is taken up by isoprenoid producing cells, the lower the isoprenoid yield. This relationship has been termed "rate-yield coupling." This inverse coupling of yield and productivity is problematic because yield and productivity are two key cost drivers in isoprenoid production. Because of rate-yield coupling, any attempt to increase productivity by increasing the rate of oxygen and/or sugar transfer results in a concomitant decrease in yield, thereby negating the cost benefit of increased productivity. The elimination of the inverse correlation between yield and productivity would be beneficial because it would be possible to simultaneously achieve high yield and high productivity and thereby maximize the efficiency (maximize isoprenoid product produced per cost of fermentation) of the isoprenoid production.

SUMMARY OF THE INVENTION

The invention relates generally to methods of uncoupling yield and productivity during the production of a non-catabolic compound during fermentation of a host cell that produces the non-catabolic compound.

In one aspect the invention provides method of decoupling yield and productivity of a non-catabolic compound produced in a host cell capable of making the non-catabolic compound involving the step of reducing ATP utilization during fermentation.

In an embodiment the ATP utilization is reduced by addition of one or more ATP depleting agents. In another embodiment the one or more ATP depleting agents is a weak organic acid. In certain embodiments the weak organic acid is selected from sorbic acid, acetic acid, benzoic acid, and propionic acid. In a preferred embodiment the weak organic acid is benzoic acid.

In other embodiments of the invention the ATP utilization is reduced by over expression of one or more ATP dissipation enzymes. In an embodiment the one or more ATP dissipation enzymes are selected from *Saccharomyces cerevisiae* SSB1 and ATP-diphosphohydrolase. In another embodiment the ATP utilization is reduced by over expression of one or more ATP uncoupling enzymes. In particular embodiments the one or more ATP uncoupling enzymes are selected from NADH oxidase (NOX) and alternative oxidase (AOX).

In further embodiments of the invention the ATP levels are reduced by expression of a futile cycle in the host cell. In certain embodiments the futile cycle is selected from simultaneous over expression of phosphofructokinase and fructose-1,6-bisphosphatase and simultaneous over expression of phosphoenolpyruvate carboxykinase and pyruvate carboxylase.

In an embodiment of the method of the invention the non-catabolic compound is selected from the group consisting of an amino acid, a fatty acid, an isoprenoid, and a polyketide. In certain embodiments the non-catabolic compound is an isoprenoid. In particular embodiments the isoprenoid is selected from the group consisting of a hemiterpene, monoterpene, diterpene, triterpene, tetraterpene, sesquiterpene, and polyterpene. In other embodiments the isoprenoid is selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene, and valencene. In a preferred embodiment the isoprenoid is β-farnesene.

In an embodiment of the method of the invention the host cell is selected from a bacterial cell, a plant cell, and a yeast cell. In certain embodiments the host cell is a yeast cell. In a preferred embodiment the yeast cell is a *Saccharomyces cerevisiae*.

In another aspect of the invention the invention provides a method of decoupling yield and productivity of a non-catabolic compound produced in a host cell capable of making the isoprenoid compound involving the step of reducing carbon flux through the citric acid cycle (TCA) in the host cell.

In an embodiment of the method of the invention carbon flux through the TCA cycle is reduced by inhibition of one or more TCA enzymes. In another embodiment the one or more TCA enzymes are downregulated. In a further embodiment the TCA enzymes are selected from citrate synthase, aconitate hydratase, NAD-dependent isocitrate dehydrogenase, 2-ketoglutarate dehydrogenase, succinyl-CoA ligase, succinate dehydrogenase, fumarate hydralase, peroxisomal malate dehydrogenase, and pyruvate carboxylase. In a preferred embodiment the TCA enzymes are pyruvate carboxylase and citrate synthase.

DETAILED DESCRIPTION OF THE EMBODIMENTS

Figure 1:
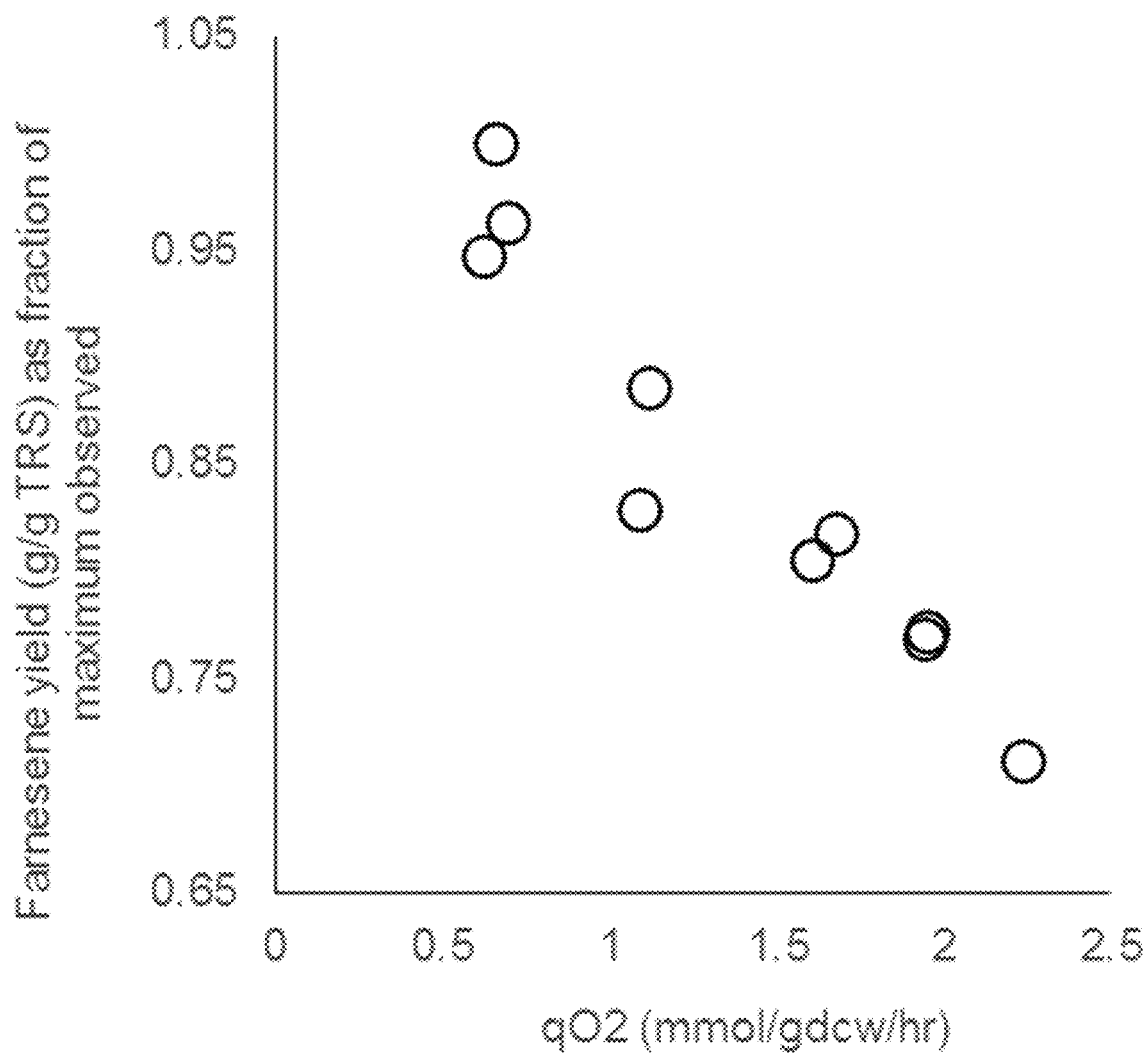
FIG. 1 is a graph of yield of farnesene at different cell specific oxygen uptake values (qO2).

As used herein, the term "productivity" or "$q_P$" with respect to the biomanufacturing of isoprenoid products refers to the moles of isoprenoid product produced per gram of dry cell weight per hour.

As used herein, the term "yield" or "$Y_{P/S}$" with respect to the biomanufacturing of isoprenoid products refers to the rate of isoprenoid product formation over the rate of sugar consumption.

As used herein, the term "$q_S$" or "sugar consumption" refers to the rate of sugar consumed during a fermentation presented as moles sugar consumed per gram dry cell weight per hour.

As used herein, the term "$q_{O2}$" or "oxygen consumption" refers to the rate of oxygen consumed during a fermentation presented as moles $O_2$ consumed per gram dry cell weight per hour.

As used herein, the term "rate-yield coupling" refers to the inverse correlation between yield and productivity during the fermentation based production of an isoprenoid.

As used herein, the term "weak organic acid" or "(WOA)" refers to organic acids having a pKa of 4.0 or greater. Non-limiting illustrative examples of WOAs include sorbic acid, acetic acid, benzoic acid, and propionic acid.

As used herein, the term "futile cycle" refers to at least two metabolic cycles or pathways that when run concurrently in opposite directions have no effect other than the dissipation of energy in the form of hydrolysis of ATP.

As used herein, the term "ATP dissipation reaction" refers to a biochemical reaction that hydrolyzes ATP without utilizing the energy for any physiological process.

As used herein, the term "ATP uncoupling reaction" refers to a biochemical reaction that uncouples NADH oxidation or proton transport from ATP generation.

As used herein, the term "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) be naturally found in the host cell but positioned outside of its natural locus.

As used herein, to "functionally disrupt" or a "functional disruption" of a target gene, e.g., one or more genes of the TCA pathway, means that the target gene is altered in such a way as to decrease in the host cell the activity of the protein encoded by the target gene. In some embodiments, the activity of the protein encoded by the target gene is eliminated in the host cell. In other embodiments, the activity of the protein encoded by the target gene is decreased in the host cell. Functional disruption of the target gene may be achieved by deleting all or a part of the gene so that gene expression is eliminated or reduced, or so that the activity of the gene product is eliminated or reduced. Functional disruption of the target gene may also be achieved by mutating a regulatory element of the gene, e.g., the promoter of the gene so that expression is eliminated or reduced, or by mutating the coding sequence of the gene so that the activity of the gene product is eliminated or reduced. In some embodiments, functional disruption of the target gene results in the removal of the complete open reading frame of the target gene.

As used herein, the term "parent cell" refers to a cell that has an identical genetic background as a host cell disclosed herein except that it does not comprise a particular heterologous nucleotide sequence, and that serves as the starting point for introducing said heterologous nucleotide sequence leading to the generation of a host cell disclosed herein.

As used herein, the term "biosynthetic enzyme" refers to an enzyme that functions in a biosynthetic pathway leading to the production of a naturally occurring molecule.

Genetically Modified Microbes Producing Isoprenoids
Host Cells

Host cells useful in the practice of the present invention include archae, prokaryotic, or eukaryotic cells.

Suitable prokaryotic hosts include but are not limited to any of a variety of gram-positive, gram-negative, or gram-variable bacteria. Examples include but are not limited to cells belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphylococcus, Streptomyces, Synechococcus*, and *Zymomonas*. Examples of prokaryotic strains include but are not limited to: *Bacillus subtilis, Bacillus amyloliquefaciens, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei*, and *Staphylococcus aureus*. In a particular embodiment, the host cell is an *Escherichia coli* cell.

Suitable archae hosts include but are not limited to cells belonging to the genera: *Aeropyrum, Archaeglobus, Halobacterium, Methanococcus, Methanobacterium, Pyrococcus, Sulfolobus*, and *Thermoplasma*. Examples of archae strains include but are not limited to: *Archaeoglobus fulgidus, Halobacterium* sp., *Methanococcus jannaschii, Methanobacterium thermoautotrophicum, Thermoplasma acidophilum, Thermoplasma volcanium, Pyrococcus horikoshii, Pyrococcus abyssi*, and *Aeropyrum pernix*.

Suitable eukaryotic hosts include but are not limited to fungal cells, algal cells, insect cells, and plant cells. In some embodiments, yeasts useful in the present methods include yeasts that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis,* and *Zygozyma*, among others.

In some embodiments, the host microbe is *Saccharomyces cerevisiae, Pichia pastoris, Schizosaccharomyces pombe, Dekkera bruxellensis, Kluyveromyces lactis* (previously called *Saccharomyces lactis*), *Kluyveromyces marxianus, Arxula adeninivorans,* or *Hansenula polymorpha* (now known as *Pichia angusta*). In some embodiments, the host microbe is a strain of the genus *Candida*, such as *Candida lipolytica, Candida guilliermondii, Candida krusei, Candida pseudotropicalis,* or *Candida utilis*.

In a particular embodiment, the host microbe is *Saccharomyces cerevisiae*. In some embodiments, the host is a strain of *Saccharomyces cerevisiae* selected from the group consisting of Baker's yeast, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1, and AL-1. In some embodiments, the host microbe is a strain of *Saccharomyces cerevisiae* selected from the group consisting of PE-2, CAT-1, VR-1, BG-1, CR-1, and SA-1. In a particular embodiment, the strain of *Saccharomyces cerevisiae* is PE-2. In another particular embodiment, the strain of *Saccharomyces cerevisiae* is CAT-1. In another particular embodiment, the strain of *Saccharomyces cerevisiae* is BG-1.

In some embodiments, the host microbe is a microbe that is suitable for industrial fermentation, e.g., bioethanol fermentation. In particular embodiments, the microbe is conditioned to subsist under high solvent concentration, high temperature, expanded substrate utilization, nutrient limitation, osmotic stress due to sugar and salts, acidity, sulfite and bacterial contamination, or combinations thereof, which are recognized stress conditions of the industrial fermentation environment.

NADH-Using HMGRs

In another aspect, provided herein is a genetically modified host cell capable of producing an isoprenoid, the cell comprising one or more heterologous nucleotide sequences encoding acetylaldehyde dehydrogenase acetylating (ADA, EC 1.2.1.10) and one or more heterologous nucleotide sequences encoding one or more enzymes of a biosynthetic pathway for the isoprenoid, wherein the one or more enzymes of the biosynthetic pathway comprise an NADH-using enzyme. Without being bound by theory, it is believed that the increased intracellular pool of NADH generated by ADA in the conversion of acetaldehyde to acetyl-CoA is utilized by the NADH-using biosynthetic enzyme, thus helping to restore intracellular redox balance while increasing the yield of the acetyl-CoA derived product.

In some embodiments, the NADH-using enzyme is an enzyme that is non-native to the biosynthetic pathway. For example, the NADH-using enzyme can replace an NADPH-using enzyme that is native to the biosynthetic pathway. In other embodiments, the NADH-using enzyme is co-expressed with a NADPH-using enzyme that is native to the biosynthetic pathway. In some embodiments, the genetically modified host cell comprises HMGR(s) that can only utilize NADH as a cofactor.

In some embodiments, the genetically modified host cell is capable of producing an isoprenoid, and the cell comprises one or more heterologous nucleotide sequences encoding one or more enzymes of a mevalonate (MEV) pathway for making isopentenyl pyrophosphate, wherein the one or more enzymes comprise a NADH-using HMG-CoA reductase (HMGR). HMG-CoA reductases catalyze the reductive deacylation of (S)-HMG-CoA to (R)-mevalonate, and are composed of two classes, class I and class II HMGrs. Class I includes the enzymes from eukaryotes and most archaea, and class II includes the HMG-CoA reductases of certain prokaryotes and archaea. In addition to the divergence in the sequences, the enzymes of the two classes also differ with regard to their cofactor specificity. Unlike the class I enzymes, which utilize NADPH exclusively, the class II HMG-CoA reductases vary in the ability to discriminate between NADPH and NADH. See, e.g., Hedl et al., *Journal of Bacteriology* 186 (7): 1927-1932 (2004). Co-factor specificities for select class II HMGRs are provided below.

TABLE 1

Co-factor specificities for select class II HMGRs

| Source | Coenzyme specificity | $K_m^{NADPH}$ (µm) | $K_m^{NADH}$ (µm) |
|---|---|---|---|
| P. mevalonii | NADH | | 80 |
| A. fulgidus | NAD(P)H | 500 | 160 |
| S. aureus | NAD(P)H | 70 | 100 |
| E. faecalis | NADPH | 30 | |

Useful HMGRs for the compositions and methods provided herein include HMGRs that are capable of utilizing NADH as a cofactor, e.g., HMGR from *P. mevalonii, A. fulgidus* or *S. aureus*. In particular embodiments, the HMGR is capable of only utilizing NADH as a cofactor, e.g., HMGR from *P. mevalonii, S. pomeroyi* or *D. acidovorans*.

In some embodiments, the NADH-using HMGR is from *Pseudomonas mevalonii*. The sequence of the wild type mvaA gene of *Pseudomonas mevalonii*, which encodes HMGR (E.C. 1.1.1.88), has been previously described. See Beach and Rodwell, *J. Bacteriol.* 171:2994-3001 (1989). Representative mvaA nucleotide sequences of *Pseudomonas mevalonii* include Genbank accession number M24015, and SEQ ID NO: 3 as provided herein. Representative HMGR protein sequences of *Pseudomonas mevalonii* include Genbank accession number AAA2583, and SEQ ID NO: 4 as provided herein.

In some embodiments, the NADH-using HMGR is from *Silicibacter pomeroyi*. A representative HMGR nucleotide sequence of *Silicibacter pomeroyi* includes SEQ ID NO: 5 as provided herein. Representative HMGR protein sequences of *Silicibacter pomeroyi* include Genbank accession number YP_164994 and SEQ ID NO: 6 as provided herein.

In some embodiments, the NADH-using HMGR is from *Delftia acidovorans*. A representative HMGR nucleotide sequence of *Delftia acidovorans* includes SEQ ID NO: 7 as provided herein. Representative HMGR protein sequences of *Delftia acidovorans* include Genbank accession number YP_001561318 and SEQ ID NO: 8 as provided herein.

NADH-using HMGRs also useful in the compositions and methods provided herein include those molecules which are said to be "derivatives" of any of the NADH-using HMGRs described herein, e.g., from *P. mevalonii, S. pomeroyi* and *D. acidovorans*. Such a "derivative" has the following characteristics: (1) it shares substantial homology with any of the NADH-using HMGRs described herein; and (2) is capable of catalyzing the reductive deacylation of (S)-HMG-CoA to (R)-mevalonate using NADH as a cofactor. A derivative of an NADH-using HMGR is said to share "substantial homology" with NADH-using HMGR if the amino acid sequences of the derivative is at least 80%, and more preferably at least 90%, and most preferably at least 95%, the same as that of NADH-using HMGR.

In some embodiments, the NADH-using HMGR is selective for NADH over NADPH as a cofactor. In some embodiments, the NADH-using HMGR is selective for NADH over NADPH as a cofactor at a $K_m^{NADH}:K_m^{NADPH}$ ratio of at least 1:2, 1:3, 1:4, 1:5 or greater than 1:5. In some embodiments, the NADH-using HMGR is engineered to be selective for NADH over NAPDH, for example, through site-directed mutagenesis of the cofactor-binding pocket. Methods for engineering NADH-selectivity are described in Watanabe et al., *Microbiology* 153:3044-3054 (2007), and methods for determining the cofactor specificity of HMGRs are described in Kim et al., *Protein Sci.* 9:1226-1234 (2000), the contents of which are hereby incorporated by reference in their entireties.

In some embodiments, the NADH-using HMGR is derived from a host species that natively comprises a mevalonate degradative pathway, for example, a host species that catabolizes mevalonate as its sole carbon source. Within these embodiments, the NADH-using HMGR, which normally catalyzes the oxidative acylation of internalized (R)-mevalonate to (S)-HMG-CoA within its native host cell, is utilized to catalyze the reverse reaction, that is, the reductive deacylation of (S)-HMG-CoA to (R)-mevalonate, in a genetically modified host cell comprising a mevalonate biosynthetic pathway. Prokaryotes capable of growth on mevalonate as their sole carbon source have been described by: Anderson et al., *J. Bacteriol,* 171(12):6468-6472 (1989); Beach et al., *J. Bacteriol.* 171:2994-3001 (1989); Bensch et al., *J. Biol. Chem.* 245:3755-3762; Fimongnari et al., *Biochemistry* 4:2086-2090 (1965); Siddiqi et al., *Biochem. Biophys. Res. Commun.* 8:110-113 (1962); Siddiqi et al., *J. Bacteriol.* 93:207-214 (1967); and Takatsuji et al., *Biochem. Biophys. Res. Commun.* 110:187-193 (1983), the contents of which are hereby incorporated by reference in their entireties.

Methods of Making Genetically Modified Cells

The methods provided herein include methods for producing a host cell that is genetically engineered to comprise an ADA and/or an NADH-using biosynthetic enzyme. Expression of an ADA and/or an NADH-using biosynthetic enzyme in a host cell can be accomplished by introducing into the host cells a nucleic acid comprising a nucleotide sequence encoding the ADA and/or NADH-using biosynthetic enzyme under the control of regulatory elements that permit expression in the host cell. In some embodiments, the nucleic acid is an extrachromosomal plasmid. In other embodiments, the nucleic acid is a chromosomal integration vector that can integrate the nucleotide sequence into the chromosome of the host cell.

Nucleic acids encoding these proteins can be introduced into the host cell by any method known to one of skill in the art without limitation (see, for example, Hinnen et al. (1978) *Proc. Natl. Acad. Sci. USA* 75:1292-3; Cregg et al. (1985) *Mol. Cell. Biol.* 5:3376-3385; Goeddel et al. eds, 1990, Methods in Enzymology, vol. 185, Academic Press, Inc., CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY). Exemplary techniques include but are not limited to spheroplasting, electroporation, PEG 1000 mediated transformation, and lithium acetate or lithium chloride mediated transformation.

The copy number of an enzyme in a host cell may be altered by modifying the transcription of the gene that encodes the enzyme. This can be achieved for example by modifying the copy number of the nucleotide sequence encoding the enzyme (e.g., by using a higher or lower copy number expression vector comprising the nucleotide sequence, or by introducing additional copies of the nucleotide sequence into the genome of the host cell or by deleting or disrupting the nucleotide sequence in the genome of the host cell), by changing the order of coding sequences on a polycistronic mRNA of an operon or breaking up an operon into individual genes each with its own control elements, or by increasing the strength of the promoter or operator to which the nucleotide sequence is operably linked. Alternatively or in addition, the copy number of an enzyme in a host cell may be altered by modifying the level of translation of an mRNA that encodes the enzyme. This can be achieved for example by modifying the stability of the mRNA, modifying the sequence of the ribosome binding site, modifying the distance or sequence between the ribosome binding site and the start codon of the enzyme coding sequence, modifying the entire intercistronic region located "upstream of" or adjacent to the 5' side of the start codon of the enzyme coding region, stabilizing the 3'-end of the mRNA transcript using hairpins and specialized sequences, modifying the codon usage of enzyme, altering expression of rare codon tRNAs used in the biosynthesis of the enzyme, and/or increasing the stability of the enzyme, as, for example, via mutation of its coding sequence.

The activity of an enzyme in a host cell can be altered in a number of ways, including, but not limited to, expressing a modified form of the enzyme that exhibits increased or decreased solubility in the host cell, expressing an altered form of the enzyme that lacks a domain through which the activity of the enzyme is inhibited, expressing a modified form of the enzyme that has a higher or lower Kcat or a lower or higher Km for the substrate, or expressing an altered form of the enzyme that is more or less affected by feed-back or feed-forward regulation by another molecule in the pathway.

In some embodiments, a nucleic acid used to genetically modify a host cell comprises one or more selectable markers useful for the selection of transformed host cells and for placing selective pressure on the host cell to maintain the foreign DNA.

In some embodiments, the selectable marker is an antibiotic resistance marker. Illustrative examples of antibiotic resistance markers include but are not limited to the BLA, NAT1, PAT, AUR1-C, PDR4, SMR1, CAT, mouse dhfr, HPH, DSDA, KAN$^R$, and SH BLE gene products. The BLA gene product from *E. coli* confers resistance to beta-lactam antibiotics (e.g., narrow-spectrum cephalosporins, cephamycins, and carbapenems (ertapenem), cefamandole, and cefoperazone) and to all the anti-gram-negative-bacterium penicillins except temocillin; the NAT1 gene product from *S. noursei* confers resistance to nourseothricin; the PAT gene product from *S. viridochromogenes* Tu94 confers resistance to bialophos; the AUR1-C gene product from *Saccharomyces cerevisiae* confers resistance to Auerobasidin A (AbA); the PDR4 gene product confers resistance to cerulenin; the SMR1 gene product confers resistance to sulfometuron methyl; the CAT gene product from Tn9 transposon confers resistance to chloramphenicol; the mouse dhfr gene product confers resistance to methotrexate; the HPH gene product of *Klebsiella pneumonia* confers resistance to Hygromycin B; the DSDA gene product of *E. coli* allows cells to grow on plates with D-serine as the sole nitrogen source; the KAN$^R$ gene of the Tn903 transposon confers resistance to G418; and the SH BLE gene product from *Streptoalloteichus hindustanus* confers resistance to Zeocin (bleomycin). In some embodiments, the antibiotic resistance marker is deleted after the genetically modified host cell disclosed herein is isolated.

In some embodiments, the selectable marker rescues an auxotrophy (e.g., a nutritional auxotrophy) in the genetically modified microorganism. In such embodiments, a parent microorganism comprises a functional disruption in one or more gene products that function in an amino acid or nucleotide biosynthetic pathway and that when non-functional renders a parent cell incapable of growing in media without supplementation with one or more nutrients. Such gene products include but are not limited to the HIS3, LEU2, LYS1, LYS2, MET15, TRP1, ADE2, and URA3 gene products in yeast. The auxotrophic phenotype can then be rescued by transforming the parent cell with an expression vector or chromosomal integration construct encoding a functional copy of the disrupted gene product, and the genetically modified host cell generated can be selected for based on the loss of the auxotrophic phenotype of the parent cell. Utilization of the URA3, TRP1, and LYS2 genes as selectable markers has a marked advantage because both positive and negative selections are possible. Positive selection is carried out by auxotrophic complementation of the URA3, TRP1, and LYS2 mutations, whereas negative selection is based on specific inhibitors, i.e., 5-fluoro-orotic acid (FOA), 5-fluoroanthranilic acid, and aminoadipic acid (aAA), respectively, that prevent growth of the prototrophic strains but allows growth of the URA3, TRP1, and LYS2 mutants, respectively. In other embodiments, the selectable marker rescues other non-lethal deficiencies or phenotypes that can be identified by a known selection method.

TCA Cycle Enzymes

The tricarboxylic acid cycle (TCA), also known as the citric acid cycle (CAC) or Krebs cycle is a series of biochemical reactions that are used to generate energy in the form of ATP through the oxidation of acetyl-CoA derived from carbohydrates, fats, and proteins. The TCA also provides precursors for the production of certain amino acids as well as the reducing agent NADH. In an embodiment of the invention, the rate and yield of isoprenoid production are uncoupled by down regulating the activity of one or more of the enzymes that participate in the TCA cycle either directly or indirectly (for example, by providing carbon to the TCA cycle).

In some embodiments, the TCA enzyme is citrate synthase also known as citrate condensing enzyme, CoA-acetylating citrate oxaloacetate-lyase, citric-condensing enzyme, citrogenase, oxaloacetate transacetase, CIT1, CIT3, (comprising the amino acid sequence NP 015325.1 or NP 014398.1), EC 2.3.3.1, EC 2.3.3.8, and EC 2.3.3.3. Citrate synthase catalyzes the conversion of oxaloacetic acid, acetyl-CoA, and water to citrate and Coenzyme A.

In some embodiments, the TCA enzyme is aconitate hydratase also known as cis-aconitase, aconitase, ACO1, (comprising the amino acid sequence NP 013407.1), and EC 4.2.1.3. Aconitate hydratase catalyzes the conversion of citrate to isocitrate through a cis-aconitate intermediate.

In some embodiments, the TCA enzyme is NAD-dependent isocitrate dehydrogenase also known as IDH2, IDH1, EC 1.1.1.42, EC 1.1.1.41, EC 1.1.1.286, and (comprising the amino acid sequence of NP 014779.1 or NP 014361.1). NAD-dependent isocitrate dehydrogenase catalyzes the NAD dependent conversion of isocitrate to 2-oxoglutarate, carbon dioxide, and NADH.

In some embodiments, the TCA enzyme is 2-ketoglutarate dehydrogenase complex also known as dihydrolipoamide dehydrogenase, KGD2, KGD1, LPD1, EC 1.2.4.2, EC 2.3.1.61, and (comprising the amino acid sequence of NP 010432.3, NP 012141.1, or NP 116635.1). 2-Ketoglutarate dehydrogenase complex catalyzes the NAD dependent conversion of 2-oxoglutarate and Coenzyme A to succinyl-CoA, carbon dioxide, and NADH.

In some embodiments, the TCA enzyme is succinyl-CoA ligase also known as LSC2, LSC1, EC 6.2.1.4, EC 6.2.1.5, EC 2.8.3.18, and (comprising the amino acid sequence of NP 011670.3 or NP 014785.3). Succinyl-CoA ligase catalyzes the conversion of succinyl-CoA, ADP, and phosphate to succinate, ATP, and Coenzyme A.

In some embodiments, the TCA enzyme is minor succinate dehydrogenase also known as SDH1, SDH2, SDH3, SDH4, succinate dehydrogenase, EC 1.3.5.4, EC 1.3.5.1, and (comprising the amino acid sequence of NP 012774.1, NP 013059.1, or NP 012781.1). Succinate dehydrogenase catalyzes the conversion of succinate and ubiquinone to fumarate and ubiquinol.

In some embodiments, the TCA enzyme is fumarate hydralase also known as FUM1, EC 4.2.1.2, and (comprising the amino acid sequence of NP 015061.1). Fumarate hydralase catalyzes the conversion of fumarate and water to malate.

In some embodiments, the TCA enzyme is peroxisomal malate dehydrogenase also known as MDH3, mitochondrial malate dehydrogenase, MDH1, cytosolic malate dehydrogenase, MDH2, EC 1.1.1.37, EC 1.1.5.4, and (comprising the amino acid sequence of NP 010205.1, NP 014515.2, or NP 012838.1). Peroxisomal malate dehydrogenase catalyzes the conversion of malate and NAD to oxaloacetic acid and NADH.

In some embodiments, the TCA enzyme is pyruvate carboxylase also known as PYC1, PYC2, EC 4.1.1.32, EC. 4.1.1.49, and (comprising the amino acid sequence of NP 011453.1 or NP 09777.1). Pyruvate carboxylase catalyzes the conversion of pyruvate, bicarbonate, and ATP to phosphate, oxaloacetic acid, and ADP.

Futile Cycles

In an aspect of the invention, yield and productivity of isoprenoids can be uncoupled in host cells producing the isoprenoids by the introduction of one or more futile cycles into the host cell. Futile cycles comprise at least two metabolic cycles or pathways that when run concurrently in opposite directions have no effect other than the dissipation of energy in the form of hydrolysis of ATP. Accordingly, the introduction of one or more futile cycles into the host cell reduces the ATP levels of the cell and thereby uncouple the yield and productivity of isoprenoid production.

In an embodiment, the futile cycle comprises the over expression of phosphofructokinase and fructose-1,6-bisphosphatase. Phosphofructokinase catalyzes the conversion of D-fructose-6-phosphate to D-fructose-1,6-biphosphate. In contrast, fructose-1,6-biophatase (EC 3.1.3.11) catalyzes the hydrolysis of D-fructose-1,6-biphosphate to D-fructose-6-phosphate in a reaction that consumes one molecule of ATP. Accordingly, simultaneous expression of both enzymes results in the dissipation of ATP. See for example, US Patent Application Publications Nos: US20150322461 and US20120088290 both of which are incorporated herein in their entireties.

In another embodiment, the futile cycle comprises the simultaneous over expression of phosphoenolpyruvate carboxykinase and pyruvate carboxylase. Phosphoenolpyruvate carboxykinase catalyzes the conversion of oxaloacetate into phosphoenolpyruvate whereas pyruvate carboxylase catalyzes the inverse reaction. Each enzyme hydrolyzes one ATP molecule per reaction. However, the net cycle also generates one ATP molecule. Accordingly, each cycle reaction dissipates one net ATP molecule. See for example, US Patent Application Publications Nos: US20150322461 and US20120088290.

ATP Dissipation Enzymes

In an aspect of the invention, yield and productivity of isoprenoids can be uncoupled in host cells producing the isoprenoids by the expression of an enzyme that dissipates ATP without producing any other physiologic effect.

In one embodiment, the over expression of the *Saccharomyces cerevisae* SSB1 gene or fragment thereof in a host cell producing an isoprenoid results in the uncoupling of the yield and productivity of the isoprenoid. The SSB1 gene encodes a chaperone protein that hydrolyses an ATP molecule as it binds nascent unfolded proteins. Accordingly, over expression of SSB1 or an enzymatically active fragment thereof results in the dissipation of ATP without producing any other physiologic effect. See for example, US Patent Application Publications Nos: US20150322461 and US20120088290.

In another embodiment, the over expression of ATP-diphosphohydrolase or fragment thereof in a host cell producing an isoprenoid results in the uncoupling of the yield and productivity of the isoprenoid. ATP-diphosphohydrolases are enzymes that catalyze the hydrolysis of both the β- and γ-phosphates of ADP and ATP. Accordingly, over expression of ATP-diphosphohydrolase or an enzymatically active fragment thereof results in the dissipation of ATP without producing any other physiologic effect. See for example, US Patent Application Publications Nos: US20150322461 and US20120088290.

In another embodiment, the over expression of NADH oxidase; EC 1.6.3.4 (NOX) or a functional fragment thereof in a host cell producing an isoprenoid results in the uncoupling of the yield and productivity of the isoprenoid. NOX reduces NADH to NAD+ by directly transferring hydrogen to $O_2$ without generating ATP. NOX lowers intracellular ATP concentrations by bypassing the native electron transport chain which would otherwise generate ATP upon oxidation of NADH to NAD+. Accordingly, over expression of NOX or a functional fragment thereof results in the dissipation of ATP without producing any other physiologic effect.

In another embodiment, the over expression of alternative oxidase (AOX) or a functional fragment thereof in a host cell producing an isoprenoid results in the uncoupling of the yield and productivity of the isoprenoid. Electron flow from ubiquinol to AOX resulting in the reduction of O2 to H2O, is not coupled to proton transport and therefore reduces the motive force used by ATP synthase to produce ATP. Accordingly, over expression of AOX or a functional fragment thereof results in the dissipation of ATP without producing any other physiologic effect.

ATP Depleting Agents

In some embodiments, ATP levels within the host cell are lowered by addition of one or more ATP depleting agents. ATP depleting agents are compounds or molecules that are capable of lowering the ATP levels within the host cell when the host cell is cultured in media containing the ATP depleting agent. In some embodiments, the ATP depleting agent is one which uncouples electron transport from ATP generation. In preferred embodiments, the ATP depleting agent is a weak organic acid. Non-limiting illustrative examples of weak organic acids are acetic acid, propionic acid, sorbic acid, and benzoic acid. The host cells can be cultured in media that contains an amount (concentration) of weak organic acid sufficient to lower ATP levels and thereby uncouple yield and productivity of the non-catabolic compound. In some embodiments the amount of weak organic acids is 0.25 mM or more. In particular embodiments, the host cell culture media has at least 0.25 mM, 0.3 mM, 0.35 mM, 0.40 mM, 0.45 mM, 0.5 mM, 0.55 mM, 0.6 mM, 0.65 mM, 0.70 mM, 0.75 mM, 0.80 mM, 0.85 mM, 0.90 mM, 0.95 mM, 1.0 mM, 2.0 mM, 3.0 mM, 4.0 mM, 5.0 mM, 6.0 mM, 7.0 mM, 8.0 mM, 9.0 mM, or 10.0 mM.

MEV Pathway

In some embodiments, the host cell further comprises one or more heterologous enzymes that function in a biosynthetic pathway for the production of a cytosolic isoprenoid. The production of the elevated level of the cytosolic isoprenoid can be affected through targeted genetic engineering of the host cell. A number of enzymes are known to function in the production of cytosolic isoprenoids or in the utilization of cytosolic acetyl-CoA and its precursors, and any one of these enzymes can be manipulated to change the level of a cytosolic isoprenoid in a host cell.

In some embodiments, the host cell comprises one or more heterologous enzyme of the MEV pathway. In some embodiments, the host cell comprises a heterologous mevalonate kinase. In other embodiments, the host cell comprises a heterologous HMG-CoA reductase. In some embodiments, the host cell comprises a heterologous IPP isomerase. In some embodiments, the host cell comprises a heterologous polyprenyl synthase. In some embodiments, the host cell comprises a heterologous FPP synthase. In some embodiments, the host cell comprises a heterologous terpene synthase. In some embodiments, the host cell comprises a heterologous farnesene synthase.

In some embodiments, the host cell comprises a heterologous nucleotide sequence encoding an enzyme that can condense two molecules of acetyl-coenzyme A to form acetoacetyl-CoA, e.g., an acetyl-CoA thiolase. Illustrative examples of nucleotide sequences encoding such an enzyme include, but are not limited to: (NC_000913 REGION: 2324131.2325315; *Escherichia coli*), (D49362; *Paracoccus denitrificans*), and (L20428; *Saccharomyces cerevisiae*).

In some embodiments, the host cell comprises a heterologous nucleotide sequence encoding an enzyme that can condense acetoacetyl-CoA with another molecule of acetyl-CoA to form 3-hydroxy-3-methylglutaryl-CoA (HMG-CoA), e.g., a HMG-CoA synthase. Illustrative examples of nucleotide sequences encoding such an enzyme include, but are not limited to: (NC_001145. complement 19061.20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

In some embodiments, the host cell comprises a heterologous nucleotide sequence encoding an enzyme that can convert HMG-CoA into mevalonate, e.g., a HMG-CoA reductase. Illustrative examples of nucleotide sequences encoding such an enzyme include, but are not limited to: (NM_206548; *Drosophila melanogaster*), (NC_002758, Locus tag SAV2545, GeneID 1122570; *Staphylococcus aureus*), (NM_204485; *Gallus gallus*), (AB015627; *Streptomyces* sp. KO 3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734.118898; *Saccharomyces cerevisiae*).

In some embodiments, the host cell comprises a heterologous nucleotide sequence encoding an enzyme that can convert mevalonate into mevalonate 5-phosphate, e.g., a mevalonate kinase. Illustrative examples of nucleotide sequences encoding such an enzyme include, but are not limited to: (L77688; *Arabidopsis thaliana*), and (X55875; *Saccharomyces cerevisiae*).

In some embodiments, the host cell comprises a heterologous nucleotide sequence encoding an enzyme that can convert mevalonate 5-phosphate into mevalonate 5-pyrophosphate, e.g., a phosphomevalonate kinase. Illustrative examples of nucleotide sequences encoding such an enzyme include, but are not limited to: (AF429385; *Hevea brasiliensis*), (NM_006556; *Homo sapiens*), and (NC_001145. complement 712315.713670; *Saccharomyces cerevisiae*).

In some embodiments, the host cell comprises a heterologous nucleotide sequence encoding an enzyme that can convert mevalonate 5-pyrophosphate into IPP, e.g., a mevalonate pyrophosphate decarboxylase. Illustrative examples of nucleotide sequences encoding such an enzyme include, but are not limited to: (X97557; *Saccharomyces cerevisiae*), (AF290095; *Enterococcus faecium*), and (U49260; *Homo sapiens*).

In some embodiments, the host cell comprises one or more heterologous nucleotide sequences encoding more than one enzyme of the MEV pathway. In some embodiments, the host cell comprises one or more heterologous nucleotide sequences encoding two enzymes of the MEV pathway. In some embodiments, the host cell comprises one or more heterologous nucleotide sequences encoding an enzyme that can convert HMG-CoA into mevalonate and an enzyme that can convert mevalonate into mevalonate 5-phosphate. In some embodiments, the host cell comprises one or more heterologous nucleotide sequences encoding three enzymes of the MEV pathway. In some embodiments, the host cell comprises one or more heterologous nucleotide sequences encoding four enzymes of the MEV pathway. In some embodiments, the host cell comprises one or more heterologous nucleotide sequences encoding five enzymes of the MEV pathway. In some embodiments, the host cell comprises one or more heterologous nucleotide sequences encoding six enzymes of the MEV pathway.

In some embodiments, the host cell produces a $C_5$ isoprenoid. These compounds are derived from one isoprene unit and are also called hemiterpenes. An illustrative example of a hemiterpene is isoprene. In other embodiments, the isoprenoid is a $C_{10}$ isoprenoid. These compounds are derived from two isoprene units and are also called monoterpenes. Illustrative examples of monoterpenes are limonene, citranellol, geraniol, menthol, perillyl alcohol, linalool, thujone, and myrcene. In other embodiments, the isoprenoid is a $C_{15}$ isoprenoid. These compounds are derived from three isoprene units and are also called sesquiterpenes. Illustrative examples of sesquiterpenes are periplanone B, gingkolide B, amorphadiene, artemisinin, artemisinic acid, valencene, nootkatone, epi-cedrol, epi-aristolochene, farnesol, gossypol, sanonin, periplanone, forskolin, and patchoulol (which is also known as patchouli alcohol). In other embodiments, the isoprenoid is a $C_{20}$ isoprenoid. These compounds are derived from four isoprene units and also called diterpenes. Illustrative examples of diterpenes are casbene, eleutherobin, paclitaxel, prostratin, pseudopterosin, and taxadiene. In yet other examples, the isoprenoid is a $C_{20+}$ isoprenoid. These compounds are derived from more than four isoprene units and include: triterpenes ($C_{30}$ isoprenoid compounds derived from 6 isoprene units) such as arbrusideE, bruceantin, testosterone, progesterone, cortisone, digitoxin, and squalene; tetraterpenes ($C_{40}$ isoprenoid compounds derived from 8 isoprenoids) such as β-carotene; and polyterpenes ($C_{40+}$ isoprenoid compounds derived from more than 8 isoprene units) such as polyisoprene. In some embodiments, the isoprenoid is selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene and valencene. Isoprenoid compounds also include, but are not limited to, carotenoids (such as lycopene, α- and β-carotene, α- and β-cryptoxanthin, bixin, zeaxanthin, astaxanthin, and lutein), steroid compounds, and compounds that are composed of isoprenoids modified by other chemical groups, such as mixed terpene-alkaloids, and coenzyme Q-10.

In some embodiments, the host cell further comprises a heterologous nucleotide sequence encoding an enzyme that can convert IPP generated via the MEV pathway into DMAPP, e.g., an IPP isomerase. Illustrative examples of nucleotide sequences encoding such an enzyme include, but are not limited to: (NC_000913, 3031087.3031635; *Escherichia coli*), and (AF082326; *Haematococcus pluvialis*).

In some embodiments, the host cell further comprises a heterologous nucleotide sequence encoding a polyprenyl synthase that can condense IPP and/or DMAPP molecules to form polyprenyl compounds containing more than five carbons.

In some embodiments, the host cell comprises a heterologous nucleotide sequence encoding an enzyme that can condense one molecule of IPP with one molecule of DMAPP to form one molecule of geranyl pyrophosphate ("GPP"), e.g., a GPP synthase. Illustrative examples of nucleotide sequences encoding such an enzyme include, but are not limited to: (AF513111; *Abies grandis*), (AF513112; *Abies grandis*), (AF513113; *Abies grandis*), (AY534686; *Antirrhinum majus*), (AY534687; *Antirrhinum majus*), (Y17376; *Arabidopsis thaliana*), (AE016877, Locus AP11092; *Bacillus cereus*; ATCC 14579), (AJ243739; *Citrus sinensis*), (AY534745; *Clarkia breweri*), (AY953508; *Ips pini*), (DQ286930; *Lycopersicon esculentum*), (AF182828; *Mentha x piperita*), (AF182827; *Mentha x piperita*), (MPI249453; *Mentha x piperita*), (PZE431697, Locus CAD24425; *Paracoccus zeaxanthinifaciens*), (AY866498; *Picrorhiza kurrooa*), (AY351862; *Vitis vinifera*), and (AF203881, Locus AAF12843; *Zymomonas mobilis*).

In some embodiments, the host cell comprises a heterologous nucleotide sequence encoding an enzyme that can condense two molecules of IPP with one molecule of DMAPP, or add a molecule of IPP to a molecule of GPP, to form a molecule of farnesyl pyrophosphate ("FPP"), e.g., a FPP synthase. Illustrative examples of nucleotide sequences that encode such an enzyme include, but are not limited to: (ATU80605; *Arabidopsis thaliana*), (ATHFPS2R; *Arabidopsis thaliana*), (AAU36376; *Artemisia annua*), (AF461050; *Bos taurus*), (D00694; *Escherichia coli* K-12), (AE009951, Locus AAL95523; *Fusobacterium nucleatum* subsp. *nucleatum* ATCC 25586), (GFFPPSGEN; *Gibberella fujikuroi*), (CP000009, Locus AAW60034; *Gluconobacter oxydans* 621H), (AF019892; *Helianthus annuus*), (HUMFAPS; *Homo sapiens*), (KLPFPSQCR; *Kluyveromyces lactis*), (LAU15777; *Lupinus albus*), (LAU20771; *Lupinus albus*), (AF309508; *Mus musculus*), (NCFPPSGEN; *Neurospora crassa*), (PAFPS1; *Parthenium argentatum*), (PAFPS2; *Parthenium argentatum*), (RATFAPS; *Rattus norvegicus*), (YSCFPP; *Saccharomyces cerevisiae*), (D89104; *Schizosaccharomyces pombe*), (CP000003, Locus AAT87386; *Streptococcus pyogenes*), (CP000017, Locus AAZ51849; *Streptococcus pyogenes*), (NC_008022, Locus YP_598856; *Streptococcus pyogenes* MGAS10270), (NC_008023, Locus YP_600845; *Streptococcus pyogenes* MGAS2096), (NC_008024, Locus YP_602832; *Streptococcus pyogenes* MGAS10750), (MZEFPS; *Zea mays*), (AE000657, Locus AAC06913; *Aquifex aeolicus* VF5), (NM_202836; *Arabidopsis thaliana*), (D84432, Locus BAA12575; *Bacillus subtilis*), (U12678, Locus AAC28894; *Bradyrhizobium japonicum* USDA 110), (BACFDPS; *Geobacillus stearothermophilus*), (NC_002940, Locus NP_873754; *Haemophilus ducreyi* 35000HP), (L42023, Locus AAC23087; *Haemophilus influenzae* Rd KW20), (J05262; *Homo sapiens*), (YP_395294; *Lactobacillus sakei* subsp. *sakei* 23K), (NC_005823, Locus YP_000273; *Leptospira interrogans* serovar Copenhageni str. Fiocruz L1-130), (AB003187; *Micrococcus luteus*), (NC_002946, Locus YP_208768; *Neisseria gonorrhoeae* FA 1090), (U00090, Locus AAB91752; *Rhizobium* sp. NGR234), (J05091; *Saccharomyces cerevisae*), (CP000031, Locus AAV93568; *Silicibacter pomeroyi* DSS-3), (AE008481, Locus AAK99890; *Streptococcus pneumoniae* R6), and (NC_004556, Locus NP 779706; *Xylella fastidiosa* Temecula1).

In some embodiments, the host cell further comprises a heterologous nucleotide sequence encoding an enzyme that can combine IPP and DMAPP or IPP and FPP to form geranylgeranyl pyrophosphate ("GGPP"). Illustrative examples of nucleotide sequences that encode such an enzyme include, but are not limited to: (ATHGERPYRS; *Arabidopsis thaliana*), (BT005328; *Arabidopsis thaliana*), (NM_119845; *Arabidopsis thaliana*), (NZ_AAJM01000380, Locus ZP_00743052; *Bacillus thuringiensis* serovar israelensis, ATCC 35646 sq1563), (CRGGPPS; *Catharanthus roseus*), (NZ_AABF02000074, Locus ZP_00144509; *Fusobacterium nucleatum* subsp. *vincentii*, ATCC 49256), (GFGGPPSGN; *Gibberella fujikuroi*), (AY371321; *Ginkgo biloba*), (AB055496; *Hevea brasiliensis*), (AB017971; *Homo sapiens*), (MCI276129; *Mucor circinelloides* f. lusitanicus), (AB016044; *Mus musculus*), (AABX01000298, Locus NCU01427; *Neurospora crassa*), (NCU20940; *Neurospora crassa*), (NZ_AAKL01000008, Locus ZP_00943566; *Ralstonia solanacearum* UW551), (AB118238; *Rattus norvegicus*), (SCU31632; *Saccharomyces cerevisiae*), (AB016095; *Synechococcus elongates*), (SAGGPS; *Sinapis alba*), (SSOGDS; *Sulfolobus acidocaldarius*), (NC_007759, Locus YP_461832; *Syntrophus aciditrophicus* SB), (NC_006840, Locus YP_204095; *Vibrio fischeri* ES114), (NM_112315; *Arabidopsis thaliana*), (ERWCRTE; *Pantoea agglomerans*), (D90087, Locus BAA14124; *Pantoea ananatis*), (X52291, Locus CAA36538; *Rhodobacter capsulatus*), (AF195122, Locus AAF24294; *Rhodobacter sphaeroides*), and (NC_004350, Locus NP_721015; *Streptococcus mutans* UA159).

In some embodiments, the host cell further comprises a heterologous nucleotide sequence encoding an enzyme that can modify a polyprenyl to form a hemiterpene, a monoterpene, a sesquiterpene, a diterpene, a triterpene, a tetraterpene, a polyterpene, a steroid compound, a carotenoid, or a modified isoprenoid compound.

In some embodiments, the heterologous nucleotide encodes a carene synthase. Illustrative examples of suitable nucleotide sequences include, but are not limited to: (AF461460, REGION 43.1926; *Picea abies*) and (AF527416, REGION: 78.1871; *Salvia stenophylla*).

In some embodiments, the heterologous nucleotide encodes a geraniol synthase. Illustrative examples of suitable nucleotide sequences include, but are not limited to: (AJ457070; *Cinnamomum tenuipilum*), (AY362553; *Ocimum basilicum*), (DQ234300; *Perilla frutescens* strain 1864), (DQ234299; *Perilla citriodora* strain 1861), (DQ234298; *Perilla citriodora* strain 4935), and (DQ088667; *Perilla citriodora*).

In some embodiments, the heterologous nucleotide encodes a linalool synthase. Illustrative examples of a suitable nucleotide sequence include, but are not limited to: (AF497485; *Arabidopsis thaliana*), (AC002294, Locus AAB71482; *Arabidopsis thaliana*), (AY059757; *Arabidopsis thaliana*), (NM_104793; *Arabidopsis thaliana*), (AF154124; *Artemisia annua*), (AF067603; *Clarkia breweri*), (AF067602; *Clarkia concinna*), (AF067601; *Clarkia breweri*), (U58314; *Clarkia breweri*), (AY840091; *Lycopersicon esculentum*), (DQ263741; *Lavandula angustifolia*), (AY083653; *Mentha citrate*), (AY693647; *Ocimum basilicum*), (XM_463918; *Oryza sativa*), (AP004078, Locus BAD07605; *Oryza sativa*), (XM_463918, Locus XP_463918; *Oryza sativa*), (AY917193; *Perilla citriodora*), (AF271259; *Perilla frutescens*), (AY473623; *Picea abies*), (DQ195274; *Picea sitchensis*), and (AF444798; *Perilla frutescens* var. *crispa* cultivar No. 79).

In some embodiments, the heterologous nucleotide encodes a limonene synthase. Illustrative examples of suitable nucleotide sequences include, but are not limited to: (+)-limonene synthases (AF514287, REGION: 47.1867; *Citrus limon*) and (AY055214, REGION: 48.1889; *Agastache rugosa*) and (−)-limonene synthases (DQ195275, REGION: 1.1905; *Picea sitchensis*), (AF006193, REGION: 73.1986; *Abies grandis*), and (MHC4SLSP, REGION: 29.1828; *Mentha spicata*).

In some embodiments, the heterologous nucleotide encodes a myrcene synthase. Illustrative examples of suitable nucleotide sequences include, but are not limited to: (U87908; *Abies grandis*), (AY195609; *Antirrhinum majus*), (AY195608; *Antirrhinum majus*), (NM_127982; *Arabidop-* sis thaliana TPS10), (NM_113485; *Arabidopsis thaliana* ATTPS-CIN), (NM 113483; *Arabidopsis thaliana* ATTPS-CIN), (AF271259; *Perilla frutescens*), (AY473626; *Picea abies*), (AF369919; *Picea abies*), and (AJ304839; *Quercus ilex*).

In some embodiments, the heterologous nucleotide encodes an ocimene synthase. Illustrative examples of suitable nucleotide sequences include, but are not limited to: (AY195607; *Antirrhinum majus*), (AY195609; *Antirrhinum majus*), (AY195608; *Antirrhinum majus*), (AK221024; *Arabidopsis thaliana*), (NM_113485; *Arabidopsis thaliana* ATTPS-CIN), (NM_113483; *Arabidopsis thaliana* ATTPS-CIN), (NM_117775; *Arabidopsis thaliana* ATTPS03), (NM_001036574; *Arabidopsis thaliana* ATTPS03), (NM_127982; *Arabidopsis thaliana* TPS10), (AB110642; *Citrus unshiu* CitMTSL4), and (AY575970; *Lotus corniculatus* var. *japonicus*).

In some embodiments, the heterologous nucleotide encodes an α-pinene synthase. Illustrative examples of suitable nucleotide sequences include, but are not limited to: (+)α-pinene synthase (AF543530, REGION: 1.1887; *Pinus taeda*), (−)α-pinene synthase (AF543527, REGION: 32.1921; *Pinus taeda*), and (+)/(−)α-pinene synthase (AGU87909, REGION: 6111892; *Abies grandis*).

In some embodiments, the heterologous nucleotide encodes a β-pinene synthase. Illustrative examples of suitable nucleotide sequences include, but are not limited to: (−)β-pinene synthases (AF276072, REGION: 1.1749; *Artemisia annua*) and (AF514288, REGION: 26.1834; *Citrus limon*).

In some embodiments, the heterologous nucleotide encodes a sabinene synthase. An illustrative example of a suitable nucleotide sequence includes but is not limited to AF051901, REGION: 26.1798 from *Salvia officinalis*.

In some embodiments, the heterologous nucleotide encodes a γ-terpinene synthase. Illustrative examples of suitable nucleotide sequences include: (AF514286, REGION: 30.1832 from *Citrus limon*) and (AB110640, REGION 1.1803 from *Citrus unshiu*).

In some embodiments, the heterologous nucleotide encodes a terpinolene synthase. Illustrative examples of a suitable nucleotide sequence include but is not limited to: (AY693650 from *Oscimum basilicum*) and (AY906866, REGION: 10.1887 from *Pseudotsuga menziesii*).

In some embodiments, the heterologous nucleotide encodes an amorphadiene synthase. An illustrative example of a suitable nucleotide sequence is SEQ ID NO. 37 of U.S. Patent Publication No. 2004/0005678.

In some embodiments, the heterologous nucleotide encodes a α-farnesene synthase. Illustrative examples of suitable nucleotide sequences include, but are not limited to DQ309034 from *Pyrus communis* cultivar d'Anjou (pear; gene name AFS1) and AY182241 from *Malus domestica* (apple; gene AFS1). Pechouus et al., *Planta* 219(1):84-94 (2004).

In some embodiments, the heterologous nucleotide encodes a β-farnesene synthase. Illustrative examples of suitable nucleotide sequences include but is not limited to GenBank accession number AF024615 from *Mentha* x *piperita* (peppermint; gene Tspa11), and AY835398 from *Artemisia annua*. Picaud et al., *Phytochemistry* 66(9): 961-967 (2005).

In some embodiments, the heterologous nucleotide encodes a farnesol synthase. Illustrative examples of suitable nucleotide sequences include, but are not limited to GenBank accession number AF529266 from *Zea mays* and YDR481C from *Saccharomyces cerevisiae* (gene Pho8). Song, L., *Applied Biochemistry and Biotechnology* 128:149-158 (2006).

In some embodiments, the heterologous nucleotide encodes a nerolidol synthase. An illustrative example of a suitable nucleotide sequence includes, but is not limited to AF529266 from *Zea mays* (maize; gene tps1).

In some embodiments, the heterologous nucleotide encodes a patchouliol synthase. Illustrative examples of suitable nucleotide sequences include, but are not limited to AY508730 REGION: 1.1659 from *Pogostemon cablin*.

In some embodiments, the heterologous nucleotide encodes a nootkatone synthase. Illustrative examples of a suitable nucleotide sequence includes, but is not limited to AF441124 REGION: 1.1647 from *Citrus sinensis* and AY917195 REGION: 1.1653 from *Perilla frutescens*.

In some embodiments, the heterologous nucleotide encodes an abietadiene synthase. Illustrative examples of suitable nucleotide sequences include, but are not limited to: (U50768; *Abies grandis*) and (AY473621; *Picea abies*).

Methods of Producing Isoprenoids

In some embodiments where the genetically modified host cell comprises a heterologous nucleotide sequence encoding an NADH-using HMGR, the genetically modified host cell produces an increased amount of the isoprenoid compound compared to a host cell not comprising a heterologous nucleotide sequence encoding an NADH-using HMGR, but is otherwise genetically identical. In some embodiments, the increased amount is at least 10%, as measured, for example, in grams per liter of cell culture, milligrams per gram of dry cell weight, on a per unit volume of cell culture basis, on a per unit dry cell weight basis, on a per unit volume of cell culture per unit time basis, or on a per unit dry cell weight per unit time basis.

In some embodiments where the genetically modified host cell comprises both a heterologous nucleotide sequence encoding an ADA and a heterologous nucleotide sequence encoding an NADH-using HMGR, the genetically modified host cell produces an increased amount of the isoprenoid compound compared to: (i) a host cell not comprising a heterologous nucleotide sequence encoding an ADA, but is otherwise genetically identical; (ii) a host cell not comprising a heterologous nucleotide sequence encoding an NADH-using HMGR, but is otherwise genetically identical; or (iii) a host cell not comprising a heterologous nucleotide sequence encoding an ADA or a heterologous sequence encoding an NADH-using HMGR, but is otherwise genetically identical. In some embodiments, the increased amount is at least 10%, as measured, for example, in grams per liter of cell culture, milligrams per gram of dry cell weight, on a per unit volume of cell culture basis, on a per unit dry cell weight basis, on a per unit volume of cell culture per unit time basis, or on a per unit dry cell weight per unit time basis.

The methods generally involve growing a host cell under suitable conditions in a suitable medium comprising a carbon source. Suitable conditions and suitable media for growing microorganisms are well known in the art. In some embodiments, the carbon source is a monosaccharide (simple sugar), a disaccharide, a polysaccharide, a non-fermentable carbon source, or one or more combinations thereof. Non-limiting examples of suitable monosaccharides include glucose, galactose, mannose, fructose, ribose, and combinations thereof. Non-limiting examples of suitable disaccharides include sucrose, lactose, maltose, trehalose, cellobiose, and combinations thereof. Non-limiting examples of suitable polysaccharides include starch, glycogen, cellulose, chitin, and combinations thereof. Non-limiting examples of suitable non-fermentable carbon sources include acetate and glycerol. In some embodiments, the suitable medium is supplemented with one or more additional agents, such as, for example, an inducing compound (e.g., when one or more nucleotide sequences encoding a gene product are under the control of an inducible promoter), a repressing compound (e.g., when one or more nucleotide sequences encoding a gene product are under the control of a repressible promoter), or a selection agent (e.g., an antibiotic to select for microorganisms comprising the genetic modifications).

EXAMPLES

Example 1

Yield is a Function of Cell-Specific Rates

Single colonies were inoculated in 15 ml of 2% sucrose, 1% maltose, 2 g/L lysine LGM with 50 mM succinate pH 5.0 in a 125 ml flask, then grown at 28° C., with shaking at 200 r.p.m. to an OD600 between 4 to 9, with residual glucose between 3 to 6 g 1-1.50% glycerol was added to culture to a concentration of 20%, then 1 ml vials of cell suspension were stored at −80° C. 1-2 vials of cells were thawed and grown in media with 3 g 1-1 yeast extract, 7 g 1-1NH4H2PO4, 1 g 1-1 KH2PO4, 0.5 g 1-1 MgSO4.7H2O, 50 mM succinate pH 5.0, 4% sucrose, 2% maltose, 2 g/L lysine and a trace metal and vitamin solution for 24 h, then sub-cultured to OD600 reading of 0.1 in the same media for 24 h. 25 ml of culture was used to inoculate a 0.5-litre fermenter (Sartorius, Germany) with 225 ml fermentation media containing 15 g 1-1 NH4H2PO4, 20 g 1-1 total reducing sugar (TRS) from cane syrup (Florida Crystals, West Palm Beach), and a trace metal and vitamin solution. The fermenter temperature was cycled between 30-34° C. and pH was maintained at 5.0 with addition of NH4OH. In an initial batch phase, the fermenter was aerated at 0.5 volume per volume per minute (VVM) and agitation ramped to maintain 30% dissolved oxygen. After the initial sugar was consumed, the rise in dissolved oxygen triggered feeding of Florida cane syrup (~800 g glucose equivalents, (also known as total reducing sugars (TRS)) per litre) at 10 g TRS per litre per hour in pulses of 10 g TRS per litre doses. Between pulses, the feed rate was lowered to 1-5 g TRS per litre per hour. The high feed rate resumes when the dissolved oxygen spikes, indicating the exhaustion of residual carbon; the high feed rate ends after a set amount of sugar is added. As cell density increased, dissolved oxygen was allowed to reach 0%, and the pulse dose was increased to 50 g TRS per litre. Oxygen transfer rate was maintained at particular rates by adjusting agitation as volume increased. Hereon, feedrate was adjusted dynamically to meet demand using an algorithm (the feedrate algorithm) that alternates between a high feedrate and low feedrate. During the low feedrate, cells consume sugar and any overflow metabolites accumulated during the high feedrate. A rise in dissolved oxygen then triggers the high feedrate to resume. The length of time spent in the low feedrate reflects the extent to which cells were over- or under-fed in the prior high feedrate pulse; this information is monitored and used to tune the high feedrate up or down, keeping the low feedrate within a defined range. Over time, feed rate matches sugar demand from cells. The feedrate algorithm ensures minimal net accumulation of fermentation products other than farnesene, biomass, and CO2. The process continued for 8-13 days. The fermentation tank undergoes fill and draw. Accumulated broth was removed daily and assayed for biomass and farnesene concentration. A concentrated solution of NH4H2PO4, trace metals and vitamins was added periodically to maintain steady state concentrations.

Oxygen delivery is typically between 100 and 120 mmol/L/hr, also referred as oxygen transfer rate or OTR. Different oxygen transfer rates (20, 110, 180, 225) during fermentation runs were achieved by combination of variable agitation rate, air flow and feed rate. Once the peak biomass levels reached (grams dry cell weight or gDCW) in the production phase, cells experience microaerobic conditions and the dissolved oxygen (dO2) is nearly zero; in other words, the oxygen uptake rate (OUR) is then equal to the oxygen transfer rate (OTR).

Fermentation yield: Farnesene yield (Ysp) is calculated as weight/weight amount of farnesene produced divided by the amount of total reducing sugars (TRS, or glucose equivalents) added to a fermentor. Grams of farnesene produced divided by grams of total reduced sugar added, expressed as a percentage, also referred simply as 'yield'. gDW or gDCW is referred as grams of dry weight, a measure of cellular biomass or amount of cells in the fermentor.

Specific oxygen uptake rate (qO2) is the specific rate of oxygen consumption by the biomass in the fermentor expressed as mmol/O2/gDCW/h. Also known as specific oxygen utilization rate (sOUR).

Specific sugar uptake rate (qS) is the specific rate of sugar consumption by biomass in the fermenter expressed as mmol/TRS/gDCW/h.

Farnesene was quantitated as previously described (Sandoval, C. M. et al. (2014) *Metab Eng* vol. 25, pp. 215-226).

Yield and productivity are two major cost drivers for any biomanufacturing process. For the biomanufacturing of non-catabolic products, the cell-specific rate of production ($q_P$, in units of mol product/gram dry cell weight/hr) and Yield ($Y_{P/S}$, or rate of product formation/rate of sugar consumption) are frequently a function of other cellular rates such as specific growth rate (1/hour) or (hour$^{-1}$), $q_S$ (mol sugar consumed/gram dry cell weight/hr) or $q_{O2}$ (mol O2 consumed/gram dry weight/hr). Design of fermentation processes that achieve the optimal combination of yield and productivity for lowest cost production requires close characterization of this relationship.

Figure 2:
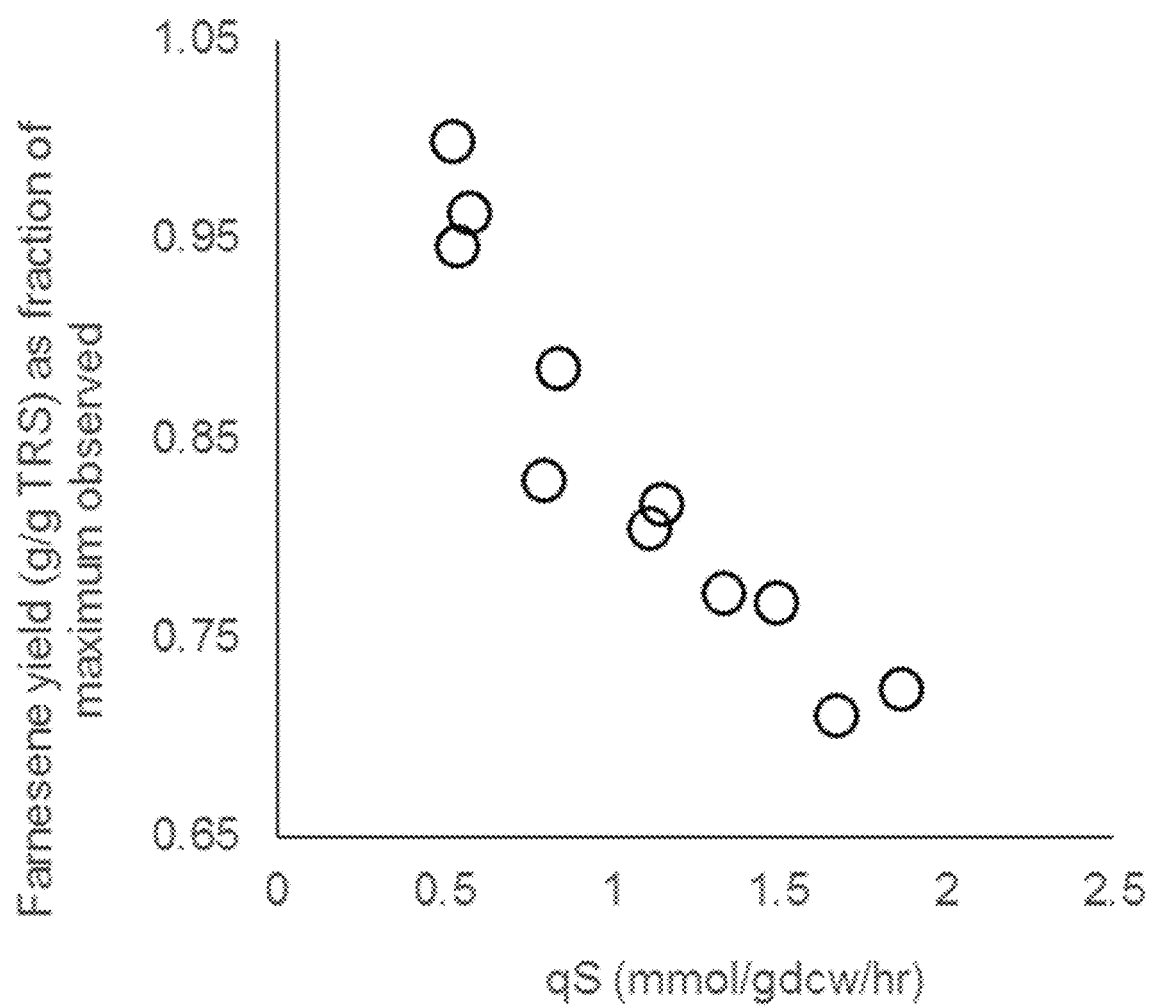
FIG. 2 is a graph of yield of farnesene at different cell specific sugar uptake values (qS).
Figure 3:
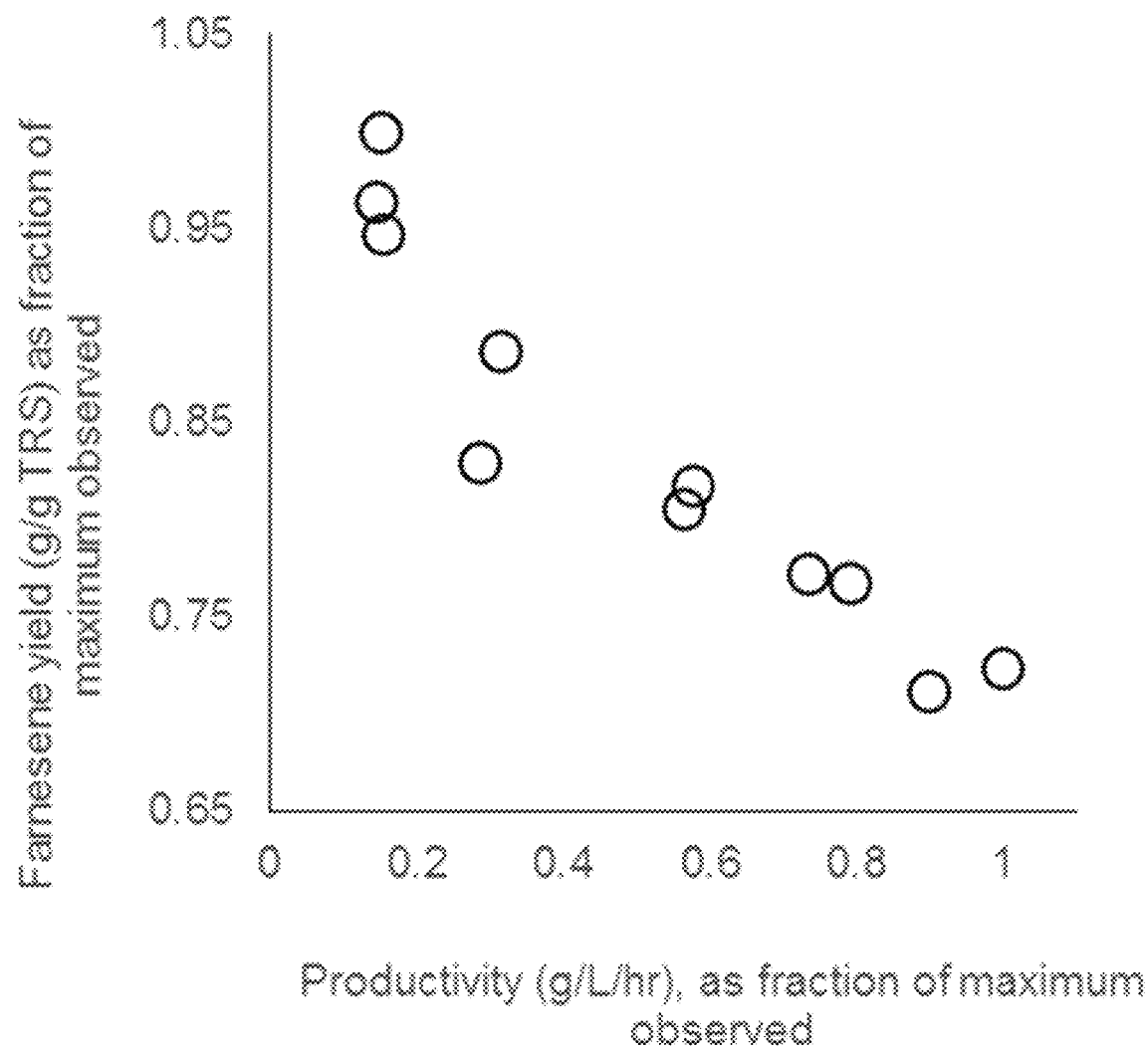
FIG. 3 is a graph of yield of farnesene at different productivity values.
Figure 4:
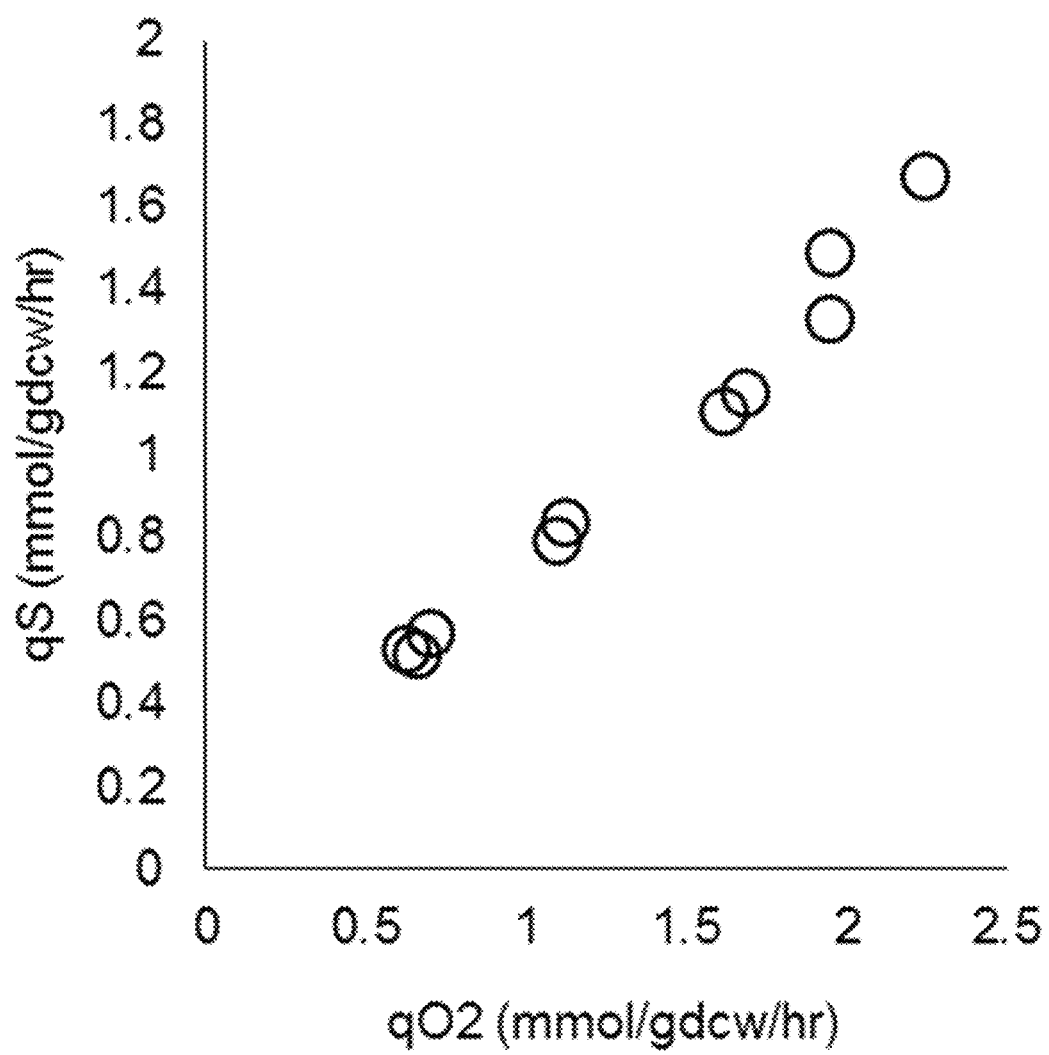
FIG. 4 is a graph of cell specific sugar uptake values (qS) at different oxygen uptake values (qO2).

For the production of isoprenoids, we have observed that yield ($Y_{P/S}$) is consistently anticorrelated with cell-specific rates of oxygen and sugar uptake rates, and by extension, volumetric productivity. In other words, the faster oxygen and sugar is taken up by our cells, the lower the isoprenoid yield. We refer to this relationship as "rate-yield coupling." FIG. 1 through FIG. 3 show this phenomenon for a single farnesene producing strain grown under different oxygen transfer rates (the rate at which oxygen is delivered to the bioreactor and taken up by cells). Yield goes down as cell specific sugar uptake, oxygen uptake, and productivity increase. FIG. 4 shows that using the feedrate algorithm, sugar uptake rate is directly proportional to oxygen uptake rate.

The anticorrelation between yield and productivity shown in FIG. 3 is problematic for industrial production of non-catabolic compounds—such as the isoprenoid farnesene—because productivity and yield are the two key cost drivers for the generation of non-catabolic compounds. When rate-yield coupling exists, any attempt to increase volumetric productivity by increasing the rate of oxygen transfer and/or sugar transfer to cells results in a concomitant decrease in yield, negating the cost benefit of increased productivity. If rate-yield coupling could be eliminated, then it would be possible to simultaneously achieve high yield and high productivity.

Example 2

Figure 5:
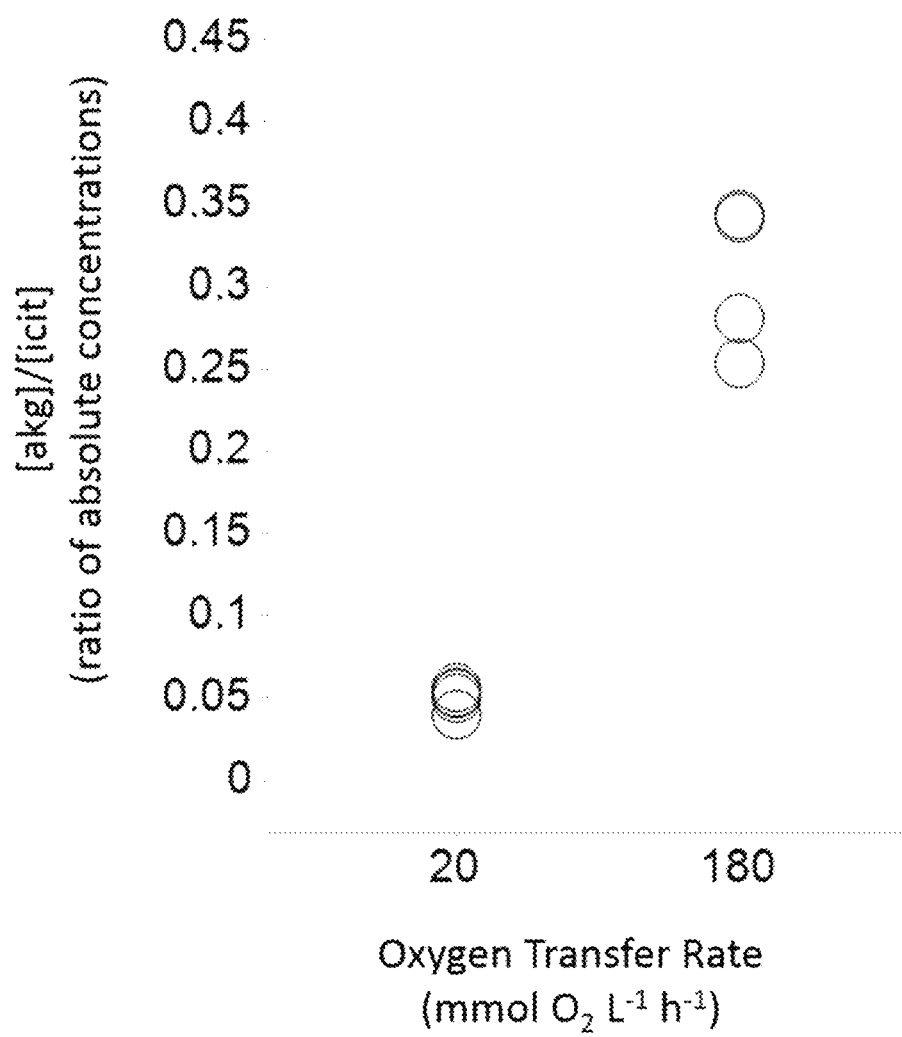
FIG. 5 is a graph plotting the ratio of alpha keto glutarate to isocitrate at different oxygen uptake rates.

Computational Modeling and Metabolomics Measurements Suggest ATP May Drive Coupling Between Rate and Yield To evaluate the possible mechanistic cause of rate yield coupling, we analyzed the absolute concentrations of central metabolites from glycolysis, the TCA cycle, the pentose phosphate pathway, and the isoprenoid pathway in fermentation samples from a single strain run at either low OTR (30 mmol $O_2$/L/hr) or high OTR (180 mmol $O_2$/L/hr). Sampling from bioreactors was performed using a rapid sampling protocol wherein a sample is immediately quenched upon removal from the tank, in order to capture the metabolic state. While the majority of central metabolites were measured at similar absolute concentrations in the low and high OTR conditions, two metabolites (isocitrate and alpha ketoglutarate) stood out as having very different concentrations (See FIG. 5). Interestingly, these two metabolites represent consecutive steps in the TCA cycle: isocitrate can be converted to alpha ketoglutarate through the action of the enzyme isocitrate dehydrogenase. We observed that isocitrate concentrations decrease and alpha ketoglutarate concentrations increased in the high OTR condition relative to the low OTR condition, suggesting that the flux rate through this step relative to others increases with the high OTR condition.

Previously it was established that excess ATP produced in catabolic pathways can be detrimental to rates and yields of a bioprocess. In terms of rates, this is because elevated ATP concentrations can be inhibitory to glycolysis. However, excess ATP can also decrease the yield of a bioprocess, since the excess ATP can drive formation of biomass, which then acts as a carbon sink that reduces product yield. An approximate stoichiometry for this is 1.5 mol excess ATP is removed or cleared from the system for every mol of Biomass formed.

Figure 6:
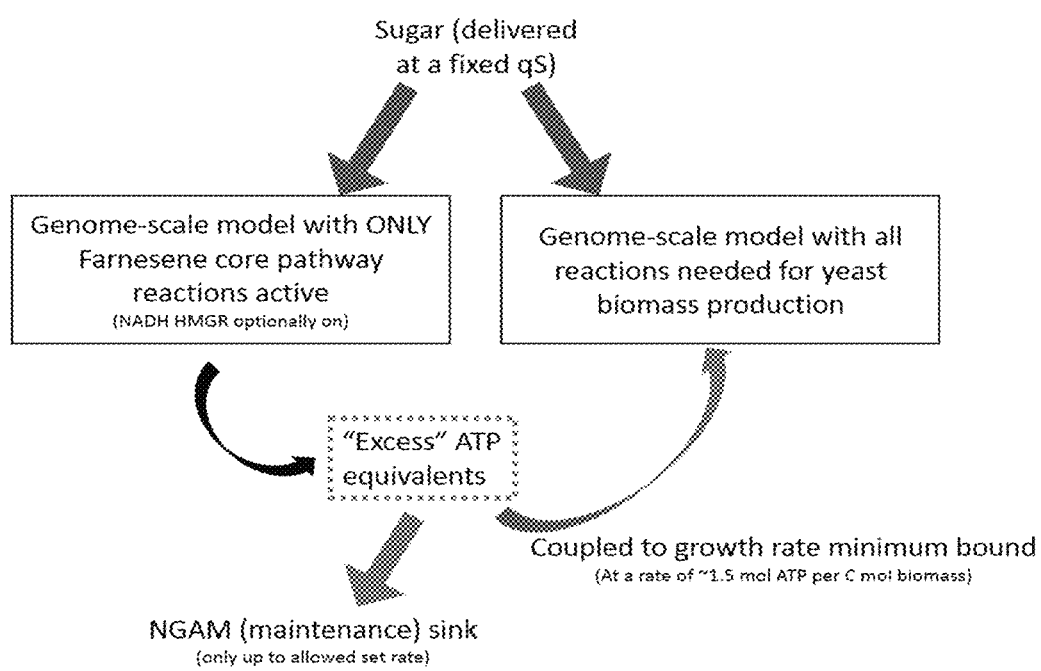
FIG. 6 is a diagram of a modification on a genome scale model that enabled the modeling of the impact of ATP production on yield of a product, by eliminating hydrolysis or futile cycles as potential sinks for ATP. (NGAM is "Non-growth associated maintenance.")

To determine whether higher flux through the TCA cycle at high OTRs could account for the lower farnesene yields, we developed a novel computational modeling framework (see FIG. 6) for evaluating the impact of ATP formation, based on a comprehensive genome-scale metabolic model. Whereas the typical genome scale model enables excess ATP to be hydrolyzed or "wasted" through futile reactions that may not happen in vivo, our new model was built such that a small amount of ATP to be apportioned to non-growth associated maintenance (or NGAM, assumed to be 0.4 mmol gDW−1 h−1.), while the remainder is strictly coupled to biomass formation, as has been commonly empirically observed. No futile cycles were permitted, and we assumed 1.5 mol ATP needed per mol Biomass formed.

Using this model, we examined the potential impact of the tricarboxylic acid cycle (TCA) flux on isoprenoid in silico. Our modeling demonstrated that an increase in TCA cycle flux from 20 to 180 OTR could indeed account for the rate-yield coupling effect observed. In other words, the rate-yield coupling effect could be explained by assuming that ATP produced from the TCA cycle at higher rates was "sunk" into biomass at a ratio of 1.5 mol ATP per mol biomass (assuming a conservative estimates of ~5.667 mol ATP/mol PYR that enters the TCA cycle.

Properties of Relevant Simulations Plotted Above to Come to this Conclusion:
  Simulations were excluded that were not within the 95% confidence interval (or CI) computed via 13C analysis for the proportion qS going through PTA at 180 OTR (*we assume it doesn't' change wildly with OTR).
  TCA cycle activity up to 25% of incoming qS. Our best estimate for TCA cycle flux as a proportion of incoming qS at 180 OTR is ~12% (around where qS ~1.4).

Materials and Methods for Example 2

Rapid Sampling and Absolute Quantitation of Metabolite Concentrations.
  Definitions: 13C IDMS means Carbon-13 isotope dilution mass spectrometry; MSTFA means N-Trimethylsilyl-N-methyl trifluoroacetamide; and MRM mode means Multiple reaction monitoring mode.
  Absolute intracellular concentrations of isocitrate and α-ketoglutarate were obtained in accordance with the procedures originally described by Canelas and Wahl. Briefly, tank broth is sampled into −80° C. methanol using a custom-built rapid sampling device, vortexed and weighted. The biomass is poured into a fast filtering apparatus and washed with 100%−80° C. methanol. The filtrate is added to a 50 mL centrifuge tube containing 30 mL of 75% v/v ethanol and 200 µL of '13C IDMS' internal standard extract. The mixture is boiled at 95° C. for 3 minutes then placed back on dry ice. The extract tubes are then evaporated to dryness in a CentriVap and resuspended in 600 µL of water. The water is filtered and dried again via lyophilization prior to 'MSTFA' derivatization and analysis.
  Absolute intracellular quantification of isocitrate and α-ketoglutarate was achieved using an Agilent 7000 triple quadrupole GC/MS in 'MRM mode' comparing signal ratio from sample extract to authentic standards (Sigma). Absolute concentrations were normalized to dry cell weight (measured at time of extraction).

Modeling:
  A genome-scale model representing yeast metabolism was produced following standard procedures. All reactions from the publically available reconstruction iTO977 were incorporated into the starting model. In addition, we added a "second generation" Farnesene pathway including 6 reactions as follows:
  Alternate HMG-CoA reductase (or NADH HMGR)
    's_3_hydroxy_3_methylglutaryl_coa_c+2.0 nadh_c<=>2.0 nad_c+r_mevalonate_c+coenzyme_a_c',
  Acetaldehyde dehydrogenase, acetylating (or ADA)
    'nad_c+coenzyme_a_c+acetaldehyde_c→acetyl_coa_c+nadh_c',
  Phosphoketolase acting on F6P (or PK-f6p)
    'phosphate_c+beta_d_fructofuranose_6_phosphate_c→h2o_c+acetyl_phosphate_c+d_erythrose_4_phosphate_c',
  Phosphoketolase acting on X5P (or PK-x5p)
    'phosphate_c+d_xylulose_5_phosphate_c→h2o_c+acetyl_phosphate_c+d_glyceraldehyde_3_phosphate_c'
  Phosphotransacetylase (or PTA)
    'coenzyme_a_c+acetyl_phosphate_c<=>phosphate_c+acetyl_coa_c',
  Farnesene Synthase (or FS)
    '_2_trans6_trans_farnesyl_diphosphate_c→diphosphate_c+beta_farnesene_c', The model was verified to produce Farnesene with a maximum theoretical yield of ~29.5% (g Farnesene/g Sugar). During this process we deactivated the following reactions to prevent uncontrolled free cycling among NAD/NADH/NADP/NADPH:

nadp_specific_glutamate_dehydrogenase_1
methylenetetrahydrofolate_dehydrogenase_nad_

A reaction named "atp_drain_flux_for_constant_maintanence_requirements" which simply represents the hydrolysis of ATP to ADP was added and constrained to a constant value of 0.4 mmol gDW−1 h−1.

Default environmental conditions were set by applying a custom function written in Python to work with the model objects of the cobrapy module version 0.3.2. The growth media was set to "glucose_aerobic_minimal" and functionally this allowed for glucose uptake at the rate of 1 mmol gDW−1 h−1 and unlimited o2, nh3, phosphate, sulfate, and h2o uptake.

Next a set of reactions referred to as the CORE farnesene biosynthetic pathway was defined. These reactions included: 'acetyl_coa_acetyltransferase'; 'glucokinase_glk1'; 'inorganic_pyrophosphatase'; 'dimethylallyltranstransferase'; 'atp_drain_flux_for_constant_maintanence_requirements; geranyltranstransferase'; 'phosphomevalonate_kinase'; 'hydroxymethylglutaryl_coa_synthase'; 'isopentenyl_diphosphate_delta_isomerase'; 'diphosphomevalonate_decarboxylase'; 'galactose_transporter'; 'farnesene_synthase'; 'exchange_of_betafarnesene_c'; 'exchange_of_phosphate_e'; 'exchange_of_alphadglucose_e'; 'exchange_of_h2o_e'; 'glucose_6_phosphate_isomerase; phosphofructokinase_1'; 'fructose_bisphosphate_aldolase'; 'triosephosphate_isomerase'; 'enolase_1'; 'transport_of_h2o_extracellular'; 'phosphoglycerate_kinase'; 'phosphoglycerate_mutase_1_1'; 'pyruvate_kinase_1'; 'pyruvate_decarboxylase_isozyme_1'; 'acetaldehyde_dehydrogenase_acetylating_'; '_3_hydroxy_3_methylglutaryl_coenzyme_a_reductase_1'; '_3_hydroxy_3_methylglutaryl_coenzyme_a_reductase_1_NADH'; 'mevalonate_kinase'; 'exchange_of_co2_e'; 'phosphoketolase_f6p'; 'phosphoketolase_x5p'; 'phosphotransacetylase'; 'transaldolase'; 'transketolase_1'; 'glucose_6_phosphate_1_dehydrogenase'; 'probable_6_phosphogluconolactonase_1'; '_6_phosphogluconate_dehydrogenase_decarboxylating_1'; 'transketolase_1_1'; 'ribose_5_phosphate_isomerase'; 'ribulose_phosphate_3_epimerase'; 'transport_of_carbon_dioxide_extracellular'; and 'glyceraldehyde_3_phosphate_dehydrogenase_1'.

The following reaction, which represents the Alternate HMG-CoA reductase (or NADH HMGR) was constrained to have 0 flux. This is because evidence suggests the majority of flux is carried by the native Sc.HMGR that uses NADPH vs. NADH:

'_3_hydroxy_3_methylglutaryl_coenzyme_a_reductase_1_NADH'

No flux was permitted to occur outside of these core reactions.

As flux is not permitted to occur outside the core reactions, any excess NADH would make the simulation unfeasible. So a reaction was added to allow extra NADH produced to convert to ATP (at an assumed stoichiometry of 1:1):

NADH+PI+ADP→NAD+ATP+H2O

We also permitted controlled free cycling among NAD/NADH/NADP/NADPH with the udhA reaction NADPH+NAD<=>NADP+NADH as this is a heterologous enzyme present in our top farnesene producers. This means excess NADPH can be converted to NADH and then to ATP using the reactions previously described.

We also introduced a reaction simulating loss of Pyruvate to the TCA cycle. 'PYR_leak_to_TCA':

PYR+5.6667 ADP+5.6667 Pi=3 CO2+5.6667 ATP+ 5.6667 H2O

Finally, we added yet another reaction that hydrolyzes ATP called the "CUSTOM_NGAM" reaction:

ATP+H2O→Pi+ADP

Once this constrained model was fully constructed it, we adjoined it to ANOTHER copy of the same yeast genome-scale metabolic model, but in this copy all reactions are unconstrained with one critical exception. Importantly, flux through the CUSTOM_NGAM reaction in the first model (the only possible drain of ATP, and NADH converted to ATP for that matter) was strictly coupled to the biomass formation reaction in the second (generally unconstrained) model. The default biomass reaction (in second model) was set to "biomass_1060_biomass". Flux through this reaction is reported as mu, or growth rate, with units 1/h. See FIG. 6 for a visual depiction of how the models are setup and interact. Both models SHARE the allotted glucose uptake maximum of 1 mmol gDW−1 h−1, so if there is excess energy produced by the first model it will come at the cost of having to send some sugar to the second model to be "sunk" into growth (biomass formation).

The coupling constraint was as follows:

Growth in (unconstrained) model≥CUSTOM_NGAM* (1./1000.)*(1./mol_atp_per_c_mol_biomass)* 12.0107*2

Where:

Growth in (unconstrained) model has units: h−1

CUSTOM_NGAM has units: mmol ATP gDW−1 h−1

The "(1./1000.)" term converts from mmol to mol, so after application of this term we have units: mol ATP gDW−1 h−1.

mol_atp_per_c_mol_biomass=1.4647 (unitless), so after application of this term we have units: cmol biomass gDW−1 h−1.

12.0107 is the atomic mass of Carbon (12.0107 g/1 cmol), so after application of this term we have units: g Carbon gDW−1 h−1.

The number "2" is included as the final term, since approximately 2 gDCW can be composed from 1 g Carbon, assuming the carbon content of a cell is about 50% of the dry weight (PMID 10482783). After application of this term, we have gDW gDW−1 h−1, and the gDW cancels leaving h−1 (matching the units on the left side of the equation for mu or growth rate).

To generate the final results, Farnesene yield in the first (constrained) model was optimized over the following parameter values for qS:

qS (20 to 180 OTR in equal intervals): [0.5, 0.92, 1.34, 1.76, 2.18, 2.6]

Figure 7:
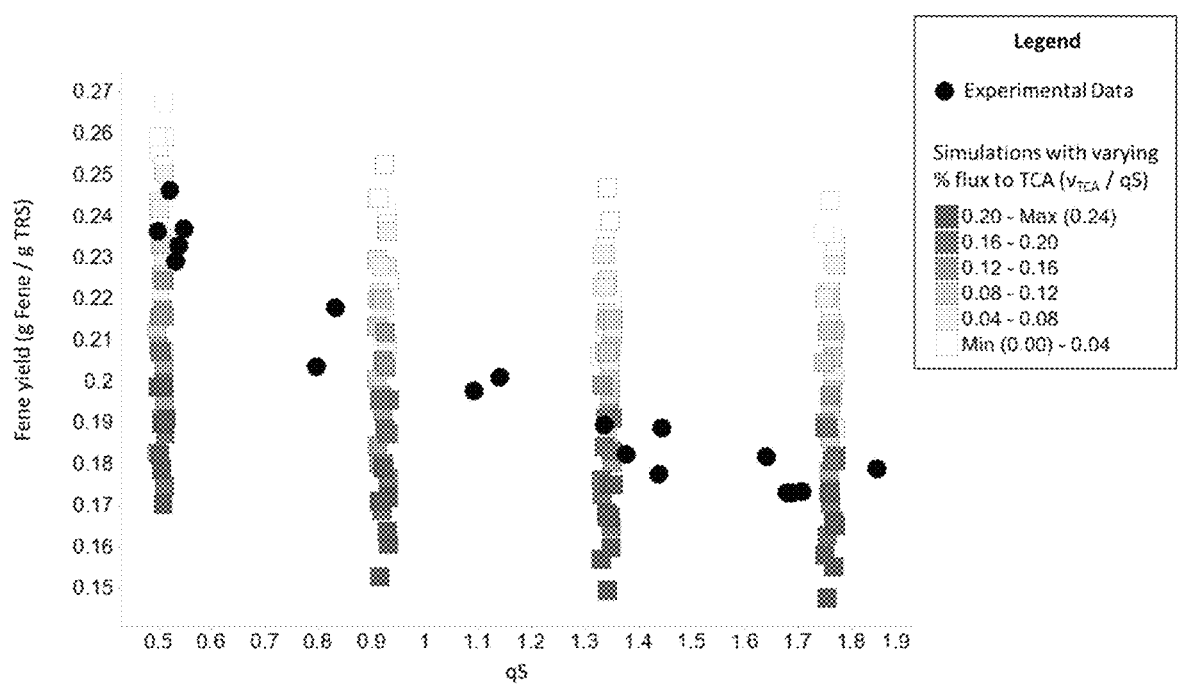
FIG. 7 is a graph plotting the data from a simulation of farnesene yield as a function of qS, at different assumed fluxes through the TCA cycle. Actual experimental data are plotted over the simulation values as black circles.

At each qS, we simulate all possible flux splits to the TCA cycle (from 0 flux into the TCA cycle up to the maximum) (see FIG. 7). To generate additional variation, we also simulate the unknown phosphotransacetylase (2$^{nd}$ generation farnesene pathway) flux from 0 to the maximum at each fixed qS and TCA cycle flux. As shown in FIG. 7, the experimental data demonstrates that the flux through the TCA cycle (as a fraction of qS) must increase.

Example 3

Futile ATP Burning Increases Product Yield Relative to Biomass

We hypothesized that excess ATP may affect rate-yield coupling, if biomass is a preferred sink for excess ATP. ATP expenditure for cell maintenance is constant regardless of specific rate of ATP production. Therefore, at low cell-specific rates, proportionately less ATP is available for biomass or non-catabolic compound production, whereas at high cell-specific rates, proportionately more ATP is available to spend on biomass or non-catabolic compound. If the most efficient way of expending excess ATP is for the cell to sink it into biomass, less carbon would be available for non-catabolic compound production and yield would decrease at high cell-specific rates. Conversely, at low cell-specific rates, there is less excess ATP to force biomass formation and proportionately more carbons can be shunted into non-catabolic compound production. This hypothesis predicts that reducing ATP levels to eliminate ATP excess that would otherwise be sunk into biomass would allow a more favorable partition of carbon into non-catabolic compounds like farnesene.

Benzoic acid can be used to deplete ATP in the cell by forcing the cells to use ATP to pump out excess protons that are moved into the cytoplasm by the benzoyl cation. A farnesene-producing strain was treated with different concentrations of benzoic acid and the effect on specific sugar uptake rate (qS), specific farnesene production rate (qP), and specific growth rate (mu) was measured. The yield (qP/qS) was calculated from measured specific sugar uptake rate and specific farnesene production rate.

Figure 8:
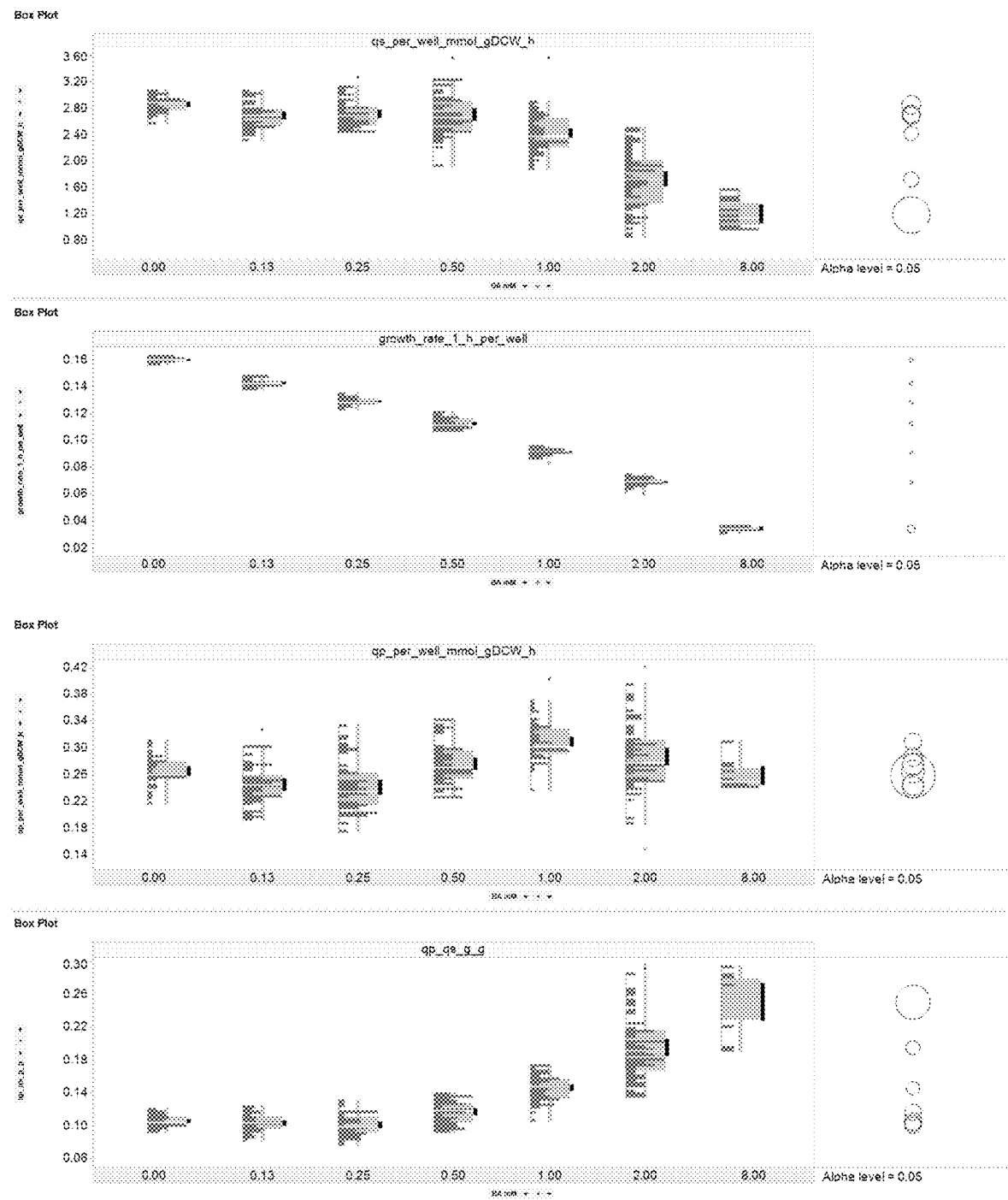
FIG. 8 is a set of graphs showing the effect of different benzoic acid concentrations (X axis=mM benzoic acid) on specific sugar uptake (qS) (Y axis top panel); growth rate (Y axis second panel from top); specific farnesene productivity (qP) (Y axis third panel from top); and calculated product yield (qP/qS) (Y axis bottom panel).

The effect of benzoic acid is shown in FIG. 8. Interestingly, while specific growth rates decreased linearly with increasing concentrations of benzoic acid, specific productivity did not change and even increased a little at intermediate concentrations. Increased benzoic acid concentrations (and associated increased ATP-wasting) was associated with more favorable partitioning of carbons into farnesene as reflected in the increased calculated yields (qP/qS). This data was intriguing and caused us to further directly measure rate-yield coupling in a strain that had been genetically modified to reduce ATP production.

Methods for Example 3

Single colonies were grown on CSM agar plates, then picked into sterile 96-well microtiter plates (1.1 mL working volume Axygen) containing 360 ul of defined liquid growth medium (LGM; as referenced in Example 1, Westfall et al, 2012) with 50 mM succinate (pH 5.0) and 2% sucrose+1% maltose+2 g/L lysine grown for 72 h at 28 C. 14 uL was sub-cultured in 360 uL of fresh defined LGM with 50 mM succinate (pH 5.0) with the indicated amounts of benzoic acid, then grown for 72 h at 33.5 C. Sucrose is spiked to 8% final concentration at day 3, then after 6 hours of incubation the culture (at early log phase) is diluted 26-fold into the production plate containing 8% sucrose and different concentrations of benzoic acid, thus avoiding a lag phase. Taking measurements of farnesene, biomass, and total residual sugar during log phase growth (at two times, T1 and T2) allows for the determination of specific productivity, growth rate, and specific sugar uptake rate. Farnesene is measured using full-well extraction with isopropanol, and quantified by UV absorbance at 220 nm with reference to a standard curve. Biomass was measured by assaying the fluorescent signal of intracellular tryptophan with an excitation wavelength of 290 nm and detection at 350 nm (UVOD). The relationship between this tryptophan signal and actual biomass is strain-dependent, and is determined empirically for each strain assayed. We do this by measuring both UVOD and biomass absorbance (OD) just prior to the start of production plates; this gives a per-well OD/UVOD conversion factor that is then used to convert UVOD signal at the end of production runs back to biomass. Another conversion we must make in determining biomass is from optical density (OD) to dry cell weight; this is also determined empirically. To eliminate any contribution of farnesene emulsion to the OD signal, cultures were diluted in a solution of 20% (v/v) PEG 20, 20% (v/v) ethanol, 2% (v/v) Triton X-114. Growth rates were determined by applying a linear regression to LN (OD) vs time. Total reducing sugars was measured by using an enzymatic determination of sucrose, fructose and glucose with an output of NADH absorption read at 340 nM, as described in various commercial kits, as such those sold by Sigma Aldrich.

Benzoic acid, acetic acid, sorbic acid, lactic acid, and propionic acid can all used to decrease biomass yields/cause ATP-wasting (when added at different levels). Many other carboxylic acids should be capable of reducing biomass yield (or causing ATP-wasting). The degree of ATP-wasting is generally related to the pKa of the acid and the octanol-water partitioning coefficient (log P) which both influence the permeability of the molecule across the membrane. At low extracellular pH, weak acids should occur predominantly in the un-dissociated form, which has relatively high membrane permeability. After entry into the cell via passive diffusion, the higher pH of the cytosol causes dissociation of the acid, thus acidifying the cell and triggering the ATP-dependent efflux of protons. Consequently, weak acids can cause, at the very least, a transient reduction of intracellular ATP levels. At high concentrations, ATP exhaustion, acidification of the cytoplasm and dissipation of the proton-motive force may occur. This 'weak-acid uncoupling' mechanism is customarily cited as the major mechanism underlying weak organic acid toxicity. Examples of weak acids that can be used to deplete cellular ATP levels are shown in Table 1 below.

TABLE 1

Examples of weak organic acids that can be used to deplete cellular ATP levels. The concentrations required to reduce the biomass yield to 50% of the reference condition ($YRC_{50}$) and the predicted concentration of un-dissociated acid at pH 5.0 are indicated along with the most commonly cited pKa and partition coefficient.

| Acid | pKa | Octanol-water partition coefficient (logP) | $YRC_{50}$ | Concentration Un-dissociated |
|---|---|---|---|---|
| Acetic Acid | 4.75 | −0.31 | 105.0 mM | 37.7 mM |
| Propionic Acid | 4.88 | 0.33 | 20.0 mM | 8.6 mM |
| Sorbic Acid | 4.76 | 1.33 | 1.3 mM | 0.47 mM |
| Benzoic Acid | 4.19 | 1.87 | 2.0 mM | 0.27 mM |

Example 4

Genetic Modifications that Lower ATP Levels Reduce Rate-Yield Coupling in Tanks

Figure 9:
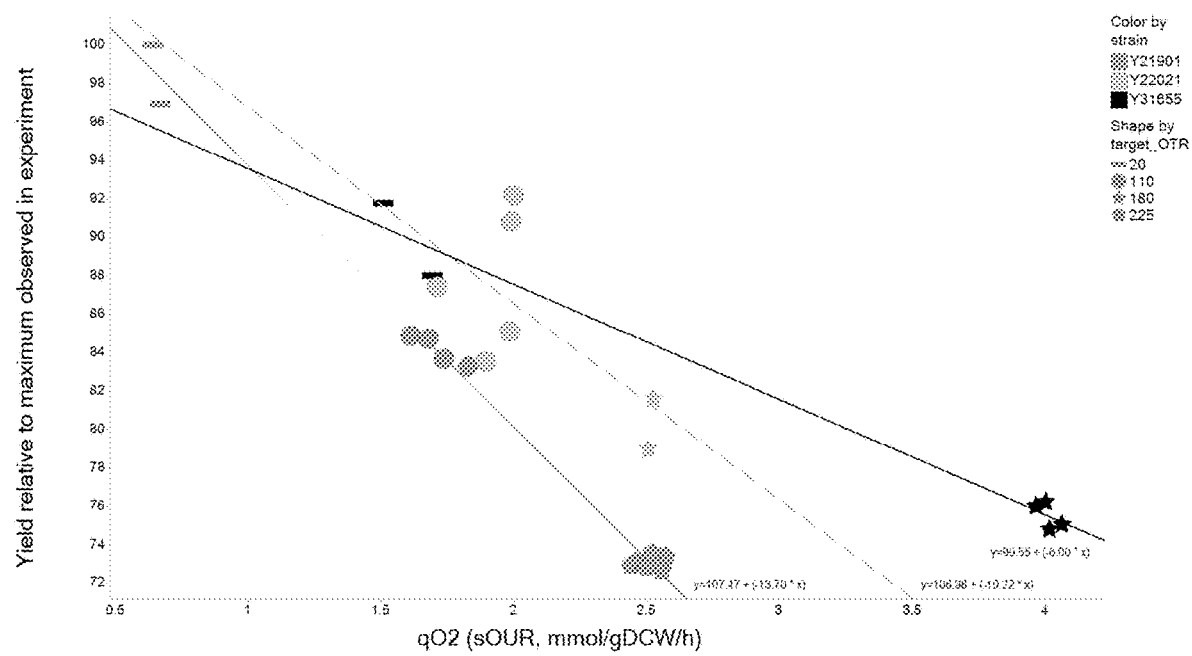
FIG. 9 is a graph showing farnesene yield over different specific oxygen uptake rates (qO2) for three strains: Y21901 (control); Y22021 (control); and Y31655 (Y22021 over expressing NOX).
Figure 10:
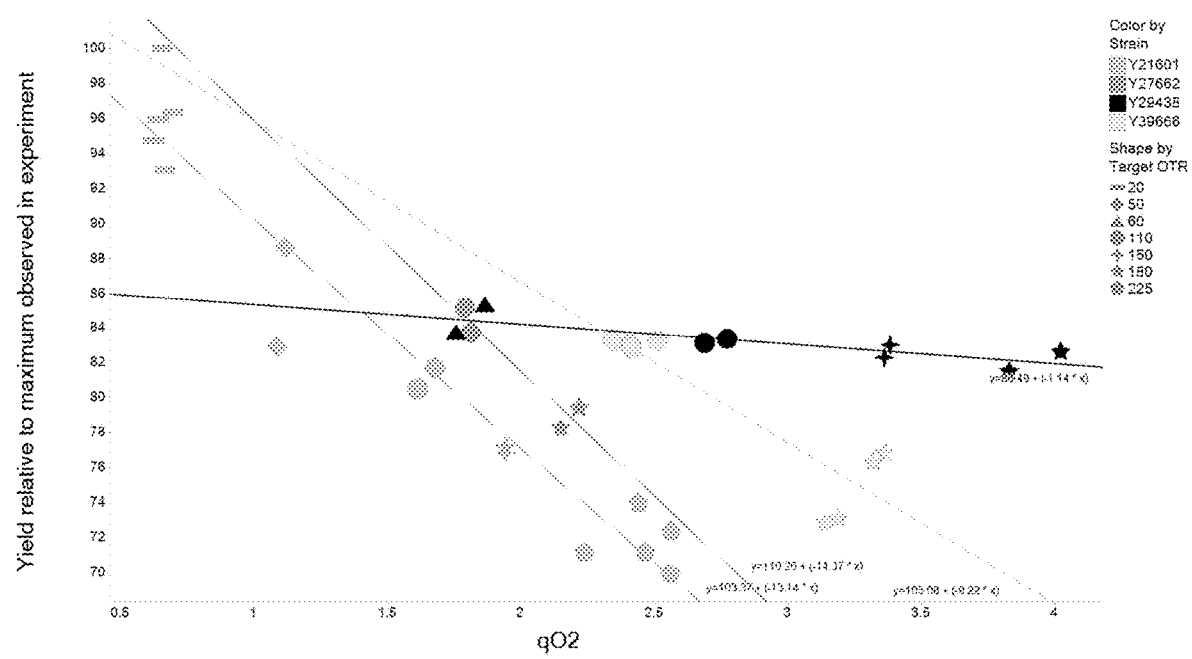
FIG. 10 is a graph showing farnesene yield over different specific oxygen uptake rates (qO2) for four strains: Y21601 (control); Y27662 (PYC1 downregulation); Y29438 (PYC1 and CIT1 downregulation); and Y39666 (CIT1 downregulation).

A farnesene-producing strain was modified by engineering overexpression of NOX (NADH oxidase) under the TDH3 promoter. The oxidation of NADH by NOX prevents NADH from being used as an electron donor for ATP synthesis by ATP synthase in the mitochondria. Thus, overexpression of NOX decreases intracellular ATP levels. This strain, Y31655, together with control strains (Y21901, Y22021) without the NOX engineering, were separately run in tanks set at different OTRs. The specific OUR (qO2) is a function of the OTR divided by the total biomass present in the tank. The rate-yield coupling effect was measured by plotting the product yield against the specific oxygen uptake rate from each tank condition. In FIG. 9, the relationship between yield and specific rate is shown in two different shades of gray for the control strains, and in black for the strain overexpressing NOX. The rate-yield coupling slope was significantly reduced (by half) in the NOX-overexpressing strain relative to the controls. This experiment shows that ATP levels affects rate-yield coupling; reduced intracellular ATP levels is associated with reduced coupling between yield and specific rate. This is consistent with our hypothesis that rate-yield coupling is driven by excess ATP that is sunk into biomass, drawing carbons away from farnesene production.

Materials and Methods

See Example 1 for details on bioreactor conditions.

The coding sequence of NADH Oxidase (defined as the nucleotide sequences spanning the start codon to the stop codon of the NADH Oxidase gene) from *Lactococcus lactis* was fused to the native *S. cerevisiae* TDH3 promoter at its 5' end, and to the terminator of the native *S. cerevisiae* TDH3 gene at its 3' end. The TDH3 promoter was defined to be the nucleotide sequence ~830 bp immediately upstream of the TDH3 start codon. The TDH3 terminator was defined to be the nucleotide sequence ~300 bp immediately downstream of the stop codon of the TDH3 gene. The TDH3 promoter-NOX-TDH3 terminator construct was integrated into the native GAS4 locus using flanking homology sequences, approximately 500 bp upstream and 500 bp downstream of the GAS4 gene, in accordance with standard yeast molecular genetic techniques.

Example 5

Reducing Flux to TCA Cycle Reduces Rate-Yield Coupling

To determine the effect on rate-yield coupling of reduced flux to the TCA cycle, which is a major source of electrons for ATP synthesis in the mitochondria, strains were made in which PYC1 or CIT1 were down-regulated, either singly or in combination. Pyc1 converts cytoplasmic pyruvate into oxaloacetate, which can be transported into the mitochondria, entering the TCA cycle. Cit1 is the rate-limiting enzyme of the TCA cycle. Down-regulation of both of these enzymes should significantly reduce carbon flux into the TCA cycle and reduce ATP production by ATP synthase in the mitochondria. We engineered down-regulation of CIT1 or PYC1 by replacing their native promoters with synthetic promoters that are active in the presence of maltose (such as during seed build conditions) but are inactive in the absence of maltose (such as during production conditions). We measured rate-yield coupling in the following farnesene-producing strains Y27662 (engineered to down-regulate PYC1), Y39666 (engineered to down-regulate CIT1), Y29438 (engineered to down-regulate both CIT1 and PYC1) and non-engineered control Y21601. Strikingly, the strain in which both PYC1 and CIT1 were down-regulated (Y29438), rate appears almost completely decoupled from yield. This observation proves that rate can be decoupled from yield, and identifies a solution to construct strains capable of maintaining both high yield and high specific rates that is compatible with manufacturing at scale. This solution is the culmination of observations from modeling and experimental evidence (all detailed above) that pointed to excess ATP as a major driver of the fate of carbons diverted into biosynthetic reactions.

Materials and Methods: Same as for NOX Experiment.

PYC1 and/or CIT1 down-regulation was achieved by replacing the native promoters of each gene with synthetic promoters that turned off in the absence of maltose, using standard yeast molecular genetic techniques for replacing or inserting DNA sequences in the yeast genome using the host's native homologous recombination machinery.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A method of decoupling yield and productivity of an isoprenoid produced in a yeast cell capable of making the isoprenoid, wherein the method comprises: adding one or more ATP depleting agents to the yeast cell and reducing ATP levels during production of the isoprenoid.

2. The method of claim 1, wherein the one or more ATP depleting agents is a weak organic acid.

3. The method of claim 2, wherein the weak organic acid is selected from sorbic acid, acetic acid, benzoic acid, and propionic acid.

4. The method of claim 3, wherein the weak organic acid is benzoic acid.

5. The method of claim 1, wherein the ATP levels are reduced by over expression of one or more ATP dissipation enzymes.

6. The method of claim 5, wherein the one or more ATP dissipation enzymes are selected from *Saccharomyces cerevisiae* SSB1 and ATP-diphosphohydrolase.

7. The method of claim 1, wherein the ATP levels are reduced by over expression of one or more ATP uncoupling enzymes.

8. The method of claim 7, wherein the one or more ATP uncoupling enzymes are selected from NADH oxidase (NOX) and alternative oxidase (AOX).

9. The method of claim 1, wherein the ATP levels are reduced by expression of a futile cycle in the yeast cell.

10. The method of claim 9, wherein the futile cycle is selected from simultaneous over expression of phosphofructokinase and fructose-1,6-bisphosphatase and simultaneous over expression of phosphoenolpyruvate carboxykinase and pyruvate carboxylase.

11. The method of claim 1, wherein the isoprenoid is selected from the group consisting of a hemiterpene, monoterpene, diterpene, triterpene, tetraterpene, sesquiterpene, and polyterpene.

12. The method of claim 1, wherein the isoprenoid is selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene, and valencene.

13. The method of claim 12, wherein the isoprenoid is β-farnesene.

14. The method of claim 1, wherein the yeast cell is a *Saccharomyces cerevisiae*.

15. The method of claim 1, wherein the ATP levels are reduced by reducing carbon flux through the citric acid cycle (TCA) in the yeast cell.

16. The method of claim 15, wherein carbon flux through the TCA cycle is reduced by decreasing expression or activity of one or more TCA enzymes.

17. The method of claim 16, wherein the TCA enzymes are selected from citrate synthase, aconitate hydratase, NAD-dependent isocitrate dehydrogenase, 2-ketoglutarate dehydrogenase, succinyl-CoA ligase, succinate dehydrogenase, fumarate hydralase, peroxisomal malate dehydrogenase, and pyruvate carboxylase.

* * * * *

SEQUENCE LISTING

```
<160> NUMBER OF SEQ ID NOS: 21

<210> SEQ ID NO 1
<211> LENGTH: 486
<212> TYPE: PRT
<213> ORGANISM: Saccharomyces cerevisiae

<400> SEQUENCE: 1

Met Val Gln Arg Leu Leu Pro Gly Ala His Ile Cys Arg Arg Ser Phe
1               5                   10                  15

Asn Ser Ser Ala Ile Ile Lys Ser Ser Ala Leu Thr Leu Lys Glu Ala
            20                  25                  30

Leu Glu Asn Val Ile Pro Lys Lys Arg Asp Ala Val Lys Lys Leu Lys
        35                  40                  45
```

```
Ala Cys Tyr Gly Ser Thr Phe Val Gly Pro Ile Thr Ile Ser Ser Val
 50                  55                  60
Leu Gly Gly Met Arg Gly Asn Gln Ser Met Phe Trp Gln Gly Thr Ser
 65                  70                  75                  80
Leu Asp Pro Glu His Gly Ile Lys Phe Gln Gly Leu Thr Ile Glu Glu
                 85                  90                  95
Cys Gln Asn Arg Leu Pro Asn Thr Gly Ile Asp Gly Asp Asn Phe Leu
                100                 105                 110
Pro Glu Ser Met Leu Trp Leu Met Thr Gly Val Pro Thr Phe
                115                 120                 125
Gln Gln Ala Ala Ser Phe Arg Lys Glu Leu Ala Ile Arg Gly Arg Lys
130                 135                 140
Leu Pro His Tyr Thr Glu Lys Val Leu Ser Ser Leu Pro Lys Asp Met
145                 150                 155                 160
His Pro Met Thr Gln Leu Ala Ile Gly Leu Ala Ser Met Asn Lys Gly
                165                 170                 175
Ser Leu Phe Ala Thr Asn Tyr Gln Lys Gly Leu Ile Gly Lys Met Glu
                180                 185                 190
Phe Trp Lys Asp Thr Leu Glu Asp Ser Leu Asn Leu Ile Ala Ser Leu
                195                 200                 205
Pro Leu Leu Thr Gly Arg Ile Tyr Ser Asn Ile Thr Asn Glu Gly His
                210                 215                 220
Pro Leu Gly Gln Tyr Ser Glu Glu Val Asp Trp Cys Thr Asn Ile Cys
225                 230                 235                 240
Ser Leu Leu Gly Met Thr Asn Gly Thr Asn Ser Ser Asn Thr Cys Asn
                245                 250                 255
Leu Thr Ser Gln Gln Ser Leu Asp Phe Ile Asn Leu Met Arg Leu Tyr
                260                 265                 270
Thr Gly Ile His Val Asp His Glu Gly Gly Asn Val Ser Ala His Thr
                275                 280                 285
Thr His Leu Val Gly Ser Ala Leu Ser Asp Pro Tyr Leu Ser Tyr Ser
                290                 295                 300
Ser Gly Ile Met Gly Leu Ala Gly Pro Leu His Gly Leu Ala Ala Gln
305                 310                 315                 320
Glu Val Val Arg Phe Leu Ile Glu Met Asn Ser Asn Ile Ser Ser Ile
                325                 330                 335
Ala Arg Glu Gln Glu Ile Lys Asp Tyr Leu Trp Lys Ile Leu Asn Ser
                340                 345                 350
Asn Arg Val Ile Pro Gly Tyr Gly His Ala Val Leu Arg Lys Pro Asp
                355                 360                 365
Pro Arg Phe Thr Ala Met Leu Glu Phe Ala Gln Lys Arg Pro Ile Glu
                370                 375                 380
Phe Glu Asn Asp Lys Asn Val Leu Leu Met Gln Lys Leu Ala Glu Ile
385                 390                 395                 400
Ala Pro Lys Val Leu Leu Glu His Gly Lys Ser Lys Asn Pro Phe Pro
                405                 410                 415
Asn Val Asp Ser Ala Ser Gly Ile Leu Phe Tyr His Tyr Gly Ile Arg
                420                 425                 430
Glu Leu Leu Phe Phe Thr Val Ile Phe Gly Cys Ser Arg Ala Met Gly
                435                 440                 445
Pro Leu Thr Gln Leu Val Trp Asp Arg Ile Leu Gly Leu Pro Ile Glu
                450                 455                 460
Arg Pro Lys Ser Leu Asn Leu Glu Gly Leu Glu Ala Leu Thr Lys Ala
```

```
                465                 470                 475                 480
Ser Asn Val Asn Lys Leu
                485

<210> SEQ ID NO 2
<211> LENGTH: 479
<212> TYPE: PRT
<213> ORGANISM: Saccharomyces cerevisiae

<400> SEQUENCE: 2

Met Ser Ala Ile Leu Ser Thr Thr Ser Lys Ser Phe Leu Ser Arg Gly
1               5                   10                  15

Ser Thr Arg Gln Cys Gln Asn Met Gln Lys Ala Leu Phe Ala Leu Leu
            20                  25                  30

Asn Ala Arg His Tyr Ser Ser Ala Ser Glu Gln Thr Leu Lys Glu Arg
        35                  40                  45

Phe Ala Glu Ile Ile Pro Ala Lys Ala Glu Ile Lys Lys Phe Lys
    50                  55                  60

Lys Glu His Gly Lys Thr Val Ile Gly Glu Val Leu Leu Glu Gln Ala
65                  70                  75                  80

Tyr Gly Gly Met Arg Gly Ile Lys Gly Leu Val Trp Glu Gly Ser Val
                85                  90                  95

Leu Asp Pro Glu Glu Gly Ile Arg Phe Arg Gly Arg Thr Ile Pro Glu
            100                 105                 110

Ile Gln Arg Glu Leu Pro Lys Ala Glu Gly Ser Thr Glu Pro Leu Pro
        115                 120                 125

Glu Ala Leu Phe Trp Leu Leu Leu Thr Gly Glu Ile Pro Thr Asp Ala
    130                 135                 140

Gln Val Lys Ala Leu Ser Ala Asp Leu Ala Ala Arg Ser Glu Ile Pro
145                 150                 155                 160

Glu His Val Ile Gln Leu Leu Asp Ser Leu Pro Lys Asp Leu His Pro
                165                 170                 175

Met Ala Gln Phe Ser Ile Ala Val Thr Ala Leu Glu Ser Glu Ser Lys
            180                 185                 190

Phe Ala Lys Ala Tyr Ala Gln Gly Val Ser Lys Glu Tyr Trp Ser
        195                 200                 205

Tyr Thr Phe Glu Asp Ser Leu Asp Leu Leu Gly Lys Leu Pro Val Ile
    210                 215                 220

Ala Ser Lys Ile Tyr Arg Asn Val Phe Lys Asp Gly Lys Ile Thr Ser
225                 230                 235                 240

Thr Asp Pro Asn Ala Asp Tyr Gly Lys Asn Leu Ala Gln Leu Leu Gly
                245                 250                 255

Tyr Glu Asn Lys Asp Phe Ile Asp Leu Met Arg Leu Tyr Leu Thr Ile
            260                 265                 270

His Ser Asp His Glu Gly Gly Asn Val Ser Ala His Thr Thr His Leu
        275                 280                 285

Val Gly Ser Ala Leu Ser Ser Pro Tyr Leu Ser Leu Ala Ala Gly Leu
    290                 295                 300

Asn Gly Leu Ala Gly Pro Leu His Gly Arg Ala Asn Gln Glu Val Leu
305                 310                 315                 320

Glu Trp Leu Phe Lys Leu Arg Glu Val Lys Gly Asp Tyr Ser Lys
                325                 330                 335

Glu Thr Ile Glu Lys Tyr Leu Trp Asp Thr Leu Asn Ala Gly Arg Val
            340                 345                 350
```

Val Pro Gly Tyr Gly His Ala Val Leu Arg Lys Thr Asp Pro Arg Tyr
            355                 360                 365

Thr Ala Gln Arg Glu Phe Ala Leu Lys His Phe Pro Asp Tyr Glu Leu
    370                 375                 380

Phe Lys Leu Val Ser Thr Ile Tyr Glu Val Ala Pro Gly Val Leu Thr
385                 390                 395                 400

Lys His Gly Lys Thr Lys Asn Pro Trp Pro Asn Val Asp Ser His Ser
                405                 410                 415

Gly Val Leu Leu Gln Tyr Tyr Gly Leu Thr Glu Ala Ser Phe Tyr Thr
                420                 425                 430

Val Leu Phe Gly Val Ala Arg Ala Ile Gly Val Leu Pro Gln Leu Ile
            435                 440                 445

Ile Asp Arg Ala Val Gly Ala Pro Ile Glu Arg Pro Lys Ser Phe Ser
        450                 455                 460

Thr Glu Lys Tyr Lys Glu Leu Val Lys Lys Ile Glu Ser Lys Asn
465                 470                 475

<210> SEQ ID NO 3
<211> LENGTH: 778
<212> TYPE: PRT
<213> ORGANISM: Pseudomonas mevalonii

<400> SEQUENCE: 3

Met Leu Ser Ala Arg Ser Ala Ile Lys Arg Pro Ile Val Arg Gly Leu
1               5                   10                  15

Ala Thr Val Ser Asn Leu Thr Arg Asp Ser Lys Val Asn Gln Asn Leu
            20                  25                  30

Leu Glu Asp His Ser Phe Ile Asn Tyr Lys Gln Asn Val Glu Thr Leu
        35                  40                  45

Asp Ile Val Arg Lys Arg Leu Asn Arg Pro Phe Thr Tyr Ala Glu Lys
    50                  55                  60

Ile Leu Tyr Gly His Leu Asp Asp Pro His Gly Gln Asp Ile Gln Arg
65                  70                  75                  80

Gly Val Ser Tyr Leu Lys Leu Arg Pro Asp Arg Val Ala Cys Gln Asp
                85                  90                  95

Ala Thr Ala Gln Met Ala Ile Leu Gln Phe Met Ser Ala Gly Leu Pro
            100                 105                 110

Gln Val Ala Lys Pro Val Thr Val His Cys Asp His Leu Ile Gln Ala
        115                 120                 125

Gln Val Gly Gly Glu Lys Asp Leu Lys Arg Ala Ile Asp Leu Asn Lys
    130                 135                 140

Glu Val Tyr Asp Phe Leu Ala Ser Ala Thr Ala Lys Tyr Asn Met Gly
145                 150                 155                 160

Phe Trp Lys Pro Gly Ser Gly Ile Ile His Gln Ile Val Leu Glu Asn
                165                 170                 175

Tyr Ala Phe Pro Gly Ala Leu Ile Ile Gly Thr Asp Ser His Thr Pro
            180                 185                 190

Asn Ala Gly Gly Leu Gly Gln Leu Ala Ile Gly Val Gly Gly Ala Asp
        195                 200                 205

Ala Val Asp Val Met Ala Gly Arg Pro Trp Glu Leu Lys Ala Pro Lys
    210                 215                 220

Ile Leu Gly Val Lys Leu Thr Gly Lys Met Asn Gly Trp Thr Ser Pro
225                 230                 235                 240

Lys Asp Ile Ile Leu Lys Leu Ala Gly Ile Thr Thr Val Lys Gly Gly
                245                 250                 255

-continued

Thr Gly Lys Ile Val Glu Tyr Phe Gly Asp Gly Val Asp Thr Phe Ser
            260                 265                 270

Ala Thr Gly Met Gly Thr Ile Cys Asn Met Gly Ala Glu Ile Gly Ala
        275                 280                 285

Thr Thr Ser Val Phe Pro Phe Asn Lys Ser Met Ile Glu Tyr Leu Glu
    290                 295                 300

Ala Thr Gly Arg Gly Lys Ile Ala Asp Phe Ala Lys Leu Tyr His Lys
305                 310                 315                 320

Asp Leu Leu Ser Ala Asp Lys Asp Ala Glu Tyr Asp Glu Val Val Glu
                325                 330                 335

Ile Asp Leu Asn Thr Leu Glu Pro Tyr Ile Asn Gly Pro Phe Thr Pro
            340                 345                 350

Asp Leu Ala Thr Pro Val Ser Lys Met Lys Glu Val Ala Val Ala Asn
        355                 360                 365

Asn Trp Pro Leu Asp Val Arg Val Gly Leu Ile Gly Ser Cys Thr Asn
    370                 375                 380

Ser Ser Tyr Glu Asp Met Ser Arg Ser Ala Ser Ile Val Lys Asp Ala
385                 390                 395                 400

Ala Ala His Gly Leu Lys Ser Lys Thr Ile Phe Thr Val Thr Pro Gly
                405                 410                 415

Ser Glu Gln Ile Arg Ala Thr Ile Glu Arg Asp Gly Gln Leu Glu Thr
            420                 425                 430

Phe Lys Glu Phe Gly Gly Ile Val Leu Ala Asn Ala Cys Gly Pro Cys
        435                 440                 445

Ile Gly Gln Trp Asp Arg Arg Asp Ile Lys Lys Gly Asp Lys Asn Thr
    450                 455                 460

Ile Val Ser Ser Tyr Asn Arg Asn Phe Thr Ser Arg Asn Asp Gly Asn
465                 470                 475                 480

Pro Gln Thr His Ala Phe Val Ala Ser Pro Glu Leu Val Thr Ala Phe
                485                 490                 495

Ala Ile Ala Gly Asp Leu Arg Phe Asn Pro Leu Thr Asp Lys Leu Lys
            500                 505                 510

Asp Lys Asp Gly Asn Glu Phe Met Leu Lys Pro Pro His Gly Asp Gly
        515                 520                 525

Leu Pro Gln Arg Gly Tyr Asp Ala Gly Glu Asn Thr Tyr Gln Ala Pro
    530                 535                 540

Pro Ala Asp Arg Ser Thr Val Glu Val Lys Val Ser Pro Thr Ser Asp
545                 550                 555                 560

Arg Leu Gln Leu Leu Lys Pro Phe Lys Pro Trp Asp Gly Lys Asp Ala
                565                 570                 575

Lys Asp Met Pro Ile Leu Ile Lys Ala Val Gly Lys Thr Thr Thr Asp
            580                 585                 590

His Ile Ser Met Ala Gly Pro Trp Leu Lys Tyr Arg Gly His Leu Glu
        595                 600                 605

Asn Ile Ser Asn Asn Tyr Met Ile Gly Ala Ile Asn Ala Glu Asn Lys
    610                 615                 620

Lys Ala Asn Cys Val Lys Asn Val Tyr Thr Gly Glu Tyr Lys Gly Val
625                 630                 635                 640

Pro Asp Thr Ala Arg Asp Tyr Arg Asp Gln Gly Ile Lys Trp Val Val
                645                 650                 655

Ile Gly Asp Glu Asn Phe Gly Glu Gly Ser Ser Arg Glu His Ala Ala
            660                 665                 670

```
Leu Glu Pro Arg Phe Leu Gly Gly Phe Ala Ile Ile Thr Lys Ser Phe
            675                 680                 685

Ala Arg Ile His Glu Thr Asn Leu Lys Lys Gln Gly Leu Leu Pro Leu
    690                 695                 700

Asn Phe Lys Asn Pro Ala Asp Tyr Asp Lys Ile Asn Pro Asp Asp Arg
705                 710                 715                 720

Ile Asp Ile Leu Gly Leu Ala Glu Leu Ala Pro Gly Lys Pro Val Thr
                725                 730                 735

Met Arg Val His Pro Lys Asn Gly Lys Pro Trp Asp Ala Val Leu Thr
            740                 745                 750

His Thr Phe Asn Asp Glu Gln Ile Glu Trp Phe Lys Tyr Gly Ser Ala
    755                 760                 765

Leu Asn Lys Ile Lys Ala Asp Glu Lys Lys
    770                 775

<210> SEQ ID NO 4
<211> LENGTH: 369
<212> TYPE: PRT
<213> ORGANISM: Pseudomonas mevalonii

<400> SEQUENCE: 4

Met Leu Arg Asn Thr Phe Phe Arg Asn Thr Ser Arg Arg Phe Leu Ala
1               5                   10                  15

Thr Val Lys Gln Pro Ser Ile Gly Arg Tyr Thr Gly Lys Pro Asn Pro
            20                  25                  30

Ser Thr Gly Lys Tyr Thr Val Ser Phe Ile Glu Gly Asp Gly Ile Gly
        35                  40                  45

Pro Glu Ile Ser Lys Ser Val Lys Lys Ile Phe Ser Ala Ala Asn Val
    50                  55                  60

Pro Ile Glu Trp Glu Ser Cys Asp Val Ser Pro Ile Phe Val Asn Gly
65                  70                  75                  80

Leu Thr Thr Ile Pro Asp Pro Ala Val Gln Ser Ile Thr Lys Asn Leu
                85                  90                  95

Val Ala Leu Lys Gly Pro Leu Ala Thr Pro Ile Gly Lys Gly His Arg
            100                 105                 110

Ser Leu Asn Leu Thr Leu Arg Lys Thr Phe Gly Leu Phe Ala Asn Val
        115                 120                 125

Arg Pro Ala Lys Ser Ile Glu Gly Phe Lys Thr Thr Tyr Glu Asn Val
    130                 135                 140

Asp Leu Val Leu Ile Arg Glu Asn Thr Glu Gly Glu Tyr Ser Gly Ile
145                 150                 155                 160

Glu His Ile Val Cys Pro Gly Val Val Gln Ser Ile Lys Leu Ile Thr
                165                 170                 175

Arg Asp Ala Ser Glu Arg Val Ile Arg Tyr Ala Phe Glu Tyr Ala Arg
            180                 185                 190

Ala Ile Gly Arg Pro Arg Val Ile Val His Lys Ser Thr Ile Gln
        195                 200                 205

Arg Leu Ala Asp Gly Leu Phe Val Asn Val Ala Lys Glu Leu Ser Lys
    210                 215                 220

Glu Tyr Pro Asp Leu Thr Leu Glu Thr Glu Leu Ile Asp Asn Ser Val
225                 230                 235                 240

Leu Lys Val Val Thr Asn Pro Ser Ala Tyr Thr Asp Ala Val Ser Val
                245                 250                 255

Cys Pro Asn Leu Tyr Gly Asp Ile Leu Ser Asp Leu Asn Ser Gly Leu
            260                 265                 270
```

```
Ser Ala Gly Ser Leu Gly Leu Thr Pro Ser Ala Asn Ile Gly His Lys
            275                 280                 285

Ile Ser Ile Phe Glu Ala Val His Gly Ser Ala Pro Asp Ile Ala Gly
            290                 295                 300

Gln Asp Lys Ala Asn Pro Thr Ala Leu Leu Ser Ser Val Met Met
305                 310                 315                 320

Leu Asn His Met Gly Leu Thr Asn His Ala Asp Gln Ile Gln Asn Ala
                325                 330                 335

Val Leu Ser Thr Ile Ala Ser Gly Pro Glu Asn Arg Thr Gly Asp Leu
            340                 345                 350

Ala Gly Thr Ala Thr Thr Ser Ser Phe Thr Glu Ala Val Ile Lys Arg
            355                 360                 365

Leu
```

<210> SEQ ID NO 5
<211> LENGTH: 360
<212> TYPE: PRT
<213> ORGANISM: Silicibacter pomeroyi

<400> SEQUENCE: 5

```
Met Leu Asn Arg Thr Ile Ala Lys Arg Thr Leu Ala Thr Ala Ala Gln
1               5                   10                  15

Ala Glu Arg Thr Leu Pro Lys Lys Tyr Gly Gly Arg Phe Thr Val Thr
            20                  25                  30

Leu Ile Pro Gly Asp Gly Val Gly Lys Glu Ile Thr Asp Ser Val Arg
            35                  40                  45

Thr Ile Phe Glu Ala Glu Asn Ile Pro Ile Asp Trp Glu Thr Ile Asn
        50                  55                  60

Ile Lys Gln Thr Asp His Lys Glu Gly Val Tyr Glu Ala Val Glu Ser
65                  70                  75                  80

Leu Lys Arg Asn Lys Ile Gly Leu Lys Gly Leu Trp His Thr Pro Ala
            85                  90                  95

Asp Gln Thr Gly His Gly Ser Leu Asn Val Ala Leu Arg Lys Gln Leu
            100                 105                 110

Asp Ile Tyr Ala Asn Val Ala Leu Phe Lys Ser Leu Lys Gly Val Lys
            115                 120                 125

Thr Arg Ile Pro Asp Ile Asp Leu Ile Val Ile Arg Glu Asn Thr Glu
            130                 135                 140

Gly Glu Phe Ser Gly Leu Glu His Glu Ser Val Pro Gly Val Val Glu
145                 150                 155                 160

Ser Leu Lys Val Met Thr Arg Pro Lys Thr Glu Arg Ile Ala Arg Phe
                165                 170                 175

Ala Phe Asp Phe Ala Lys Lys Tyr Asn Arg Lys Ser Val Thr Ala Val
            180                 185                 190

His Lys Ala Asn Ile Met Lys Leu Gly Asp Gly Leu Phe Arg Asn Ile
            195                 200                 205

Ile Thr Glu Ile Gly Gln Lys Glu Tyr Pro Asp Ile Asp Val Ser Ser
            210                 215                 220

Ile Ile Val Asp Asn Ala Ser Met Gln Ala Val Ala Lys Pro His Gln
225                 230                 235                 240

Phe Asp Val Leu Val Thr Pro Ser Met Tyr Gly Thr Ile Leu Gly Asn
                245                 250                 255

Ile Gly Ala Ala Leu Ile Gly Gly Pro Gly Leu Val Ala Gly Ala Asn
            260                 265                 270
```

```
Phe Gly Arg Asp Tyr Ala Val Phe Glu Pro Gly Ser Arg His Val Gly
            275                 280                 285

Leu Asp Ile Lys Gly Gln Asn Val Ala Asn Pro Thr Ala Met Ile Leu
290                 295                 300

Ser Ser Thr Leu Met Leu Asn His Leu Gly Leu Asn Glu Tyr Ala Thr
305                 310                 315                 320

Arg Ile Ser Lys Ala Val His Glu Thr Ile Ala Glu Gly Lys His Thr
                325                 330                 335

Thr Arg Asp Ile Gly Gly Ser Ser Thr Thr Asp Phe Thr Asn Glu
                340                 345                 350

Ile Ile Asn Lys Leu Ser Thr Met
                355                 360

<210> SEQ ID NO 6
<211> LENGTH: 463
<212> TYPE: PRT
<213> ORGANISM: Silicibacter pomeroyi

<400> SEQUENCE: 6

Met Leu Ser Arg Ala Thr Arg Thr Ala Ala Ala Lys Ser Leu Val Lys
1               5                   10                  15

Ser Lys Val Ala Arg Asn Val Met Ala Ala Ser Phe Val Lys Arg His
                20                  25                  30

Ala Ser Thr Ser Leu Phe Lys Gln Ala Asn Lys Val Glu Ser Leu Gly
            35                  40                  45

Ser Ile Tyr Leu Ser Gly Lys Lys Ile Ser Val Ala Ala Asn Pro Phe
        50                  55                  60

Ser Ile Thr Ser Asn Arg Phe Lys Ser Thr Ser Ile Glu Val Pro Pro
65                  70                  75                  80

Met Ala Glu Ser Leu Thr Glu Gly Ser Leu Lys Glu Tyr Thr Lys Asn
                85                  90                  95

Val Gly Asp Phe Ile Lys Glu Asp Glu Leu Leu Ala Thr Ile Glu Thr
            100                 105                 110

Asp Lys Ile Asp Ile Glu Val Asn Ser Pro Val Ser Gly Thr Val Thr
        115                 120                 125

Lys Leu Asn Phe Lys Pro Glu Asp Thr Val Thr Val Gly Glu Glu Leu
    130                 135                 140

Ala Gln Val Glu Pro Gly Glu Ala Pro Ala Glu Gly Ser Gly Glu Ser
145                 150                 155                 160

Lys Pro Glu Pro Thr Glu Gln Ala Glu Pro Ser Gln Gly Val Ala Ala
                165                 170                 175

Arg Glu Asn Ser Ser Glu Glu Thr Ala Ser Lys Lys Glu Ala Ala Pro
            180                 185                 190

Lys Lys Glu Ala Ala Pro Lys Lys Glu Val Thr Glu Pro Lys Lys Ala
        195                 200                 205

Asp Gln Pro Lys Lys Thr Val Ser Lys Ala Glu Pro Pro Val Ala
    210                 215                 220

Ser Asn Ser Phe Thr Pro Phe Pro Arg Thr Glu Thr Arg Val Lys Met
225                 230                 235                 240

Asn Arg Met Arg Leu Arg Ile Ala Glu Arg Leu Lys Glu Ser Gln Asn
                245                 250                 255

Thr Ala Ala Ser Leu Thr Thr Phe Asn Glu Val Asp Met Ser Ala Leu
            260                 265                 270

Met Glu Met Arg Lys Leu Tyr Lys Asp Glu Ile Ile Lys Lys Thr Gly
```

```
            275                 280                 285
Thr Lys Phe Gly Phe Met Gly Leu Phe Ser Lys Ala Cys Thr Leu Ala
        290                 295                 300

Ala Lys Asp Ile Pro Ala Val Asn Gly Ala Ile Glu Gly Asp Gln Ile
305                 310                 315                 320

Val Tyr Arg Asp Tyr Thr Asp Ile Ser Val Ala Val Ala Thr Pro Lys
                    325                 330                 335

Gly Leu Val Thr Pro Val Val Arg Asn Ala Glu Ser Leu Ser Val Leu
                340                 345                 350

Asp Ile Glu Asn Glu Ile Val Arg Leu Ser His Lys Ala Arg Asp Gly
            355                 360                 365

Lys Leu Thr Leu Glu Asp Met Thr Gly Gly Thr Phe Thr Ile Ser Asn
    370                 375                 380

Gly Gly Val Phe Gly Ser Leu Tyr Gly Thr Pro Ile Ile Asn Ser Pro
385                 390                 395                 400

Gln Thr Ala Val Leu Gly Leu His Gly Val Lys Glu Arg Pro Val Thr
                    405                 410                 415

Val Asn Gly Gln Ile Val Ser Arg Pro Met Met Tyr Leu Ala Leu Thr
                420                 425                 430

Tyr Asp His Arg Leu Leu Asp Gly Arg Glu Ala Val Thr Phe Leu Lys
            435                 440                 445

Thr Val Lys Glu Leu Ile Glu Asp Pro Arg Lys Met Leu Leu Trp
    450                 455                 460

<210> SEQ ID NO 7
<211> LENGTH: 1014
<212> TYPE: PRT
<213> ORGANISM: Delftia acidovorans

<400> SEQUENCE: 7

Met Leu Arg Phe Val Ser Ser Gln Thr Cys Arg Tyr Ser Ser Arg Gly
1               5                   10                  15

Leu Leu Lys Thr Ser Leu Leu Lys Asn Ala Ser Thr Val Lys Ile Val
            20                  25                  30

Gly Arg Gly Leu Ala Thr Thr Gly Thr Asp Asn Phe Leu Ser Thr Ser
        35                  40                  45

Asn Ala Thr Tyr Ile Asp Glu Met Tyr Gln Ala Trp Gln Lys Asp Pro
50                  55                  60

Ser Ser Val His Val Ser Trp Asp Ala Tyr Phe Lys Asn Met Ser Asn
65                  70                  75                  80

Pro Lys Ile Pro Ala Thr Lys Ala Phe Gln Ala Pro Ser Ile Ser
                85                  90                  95

Asn Phe Pro Gln Gly Thr Glu Ala Ala Pro Leu Gly Thr Ala Met Thr
                100                 105                 110

Gly Ser Val Asp Glu Asn Val Ser Ile His Leu Lys Val Gln Leu Leu
            115                 120                 125

Cys Arg Ala Tyr Gln Val Arg Gly His Leu Lys Ala His Ile Asp Pro
    130                 135                 140

Leu Gly Ile Ser Phe Gly Ser Asn Lys Asn Pro Val Pro Glu
145                 150                 155                 160

Leu Thr Leu Asp Tyr Tyr Gly Phe Ser Lys His Asp Leu Asp Lys Glu
                165                 170                 175

Ile Asn Leu Gly Pro Gly Ile Leu Pro Arg Phe Ala Arg Asp Gly Lys
            180                 185                 190
```

-continued

```
Ser Lys Met Ser Leu Lys Glu Ile Val Asp His Leu Glu Lys Leu Tyr
        195                 200                 205

Cys Ser Ser Tyr Gly Val Gln Tyr Thr His Ile Pro Ser Lys Gln Lys
    210                 215                 220

Cys Asp Trp Leu Arg Glu Arg Ile Glu Ile Pro Glu Pro Tyr Gln Tyr
225                 230                 235                 240

Thr Val Asp Gln Lys Arg Gln Ile Leu Asp Arg Leu Thr Trp Ala Thr
                245                 250                 255

Ser Phe Glu Ser Phe Leu Ser Thr Lys Phe Pro Asn Asp Lys Arg Phe
            260                 265                 270

Gly Leu Glu Gly Leu Glu Ser Val Val Pro Gly Ile Lys Thr Leu Val
        275                 280                 285

Asp Arg Ser Val Glu Leu Gly Val Glu Asp Ile Val Leu Gly Met Ala
    290                 295                 300

His Arg Gly Arg Leu Asn Val Leu Ser Asn Val Val Arg Lys Pro Asn
305                 310                 315                 320

Glu Ser Ile Phe Ser Glu Phe Lys Gly Ser Ser Ala Arg Asp Asp Ile
                325                 330                 335

Glu Gly Ser Gly Asp Val Lys Tyr His Leu Gly Met Asn Tyr Gln Arg
            340                 345                 350

Pro Thr Thr Ser Gly Lys Tyr Val Asn Leu Ser Leu Val Ala Asn Pro
        355                 360                 365

Ser His Leu Glu Ser Gln Asp Pro Val Val Leu Gly Arg Thr Arg Ala
    370                 375                 380

Leu Leu His Ala Lys Asn Asp Leu Lys Glu Lys Thr Lys Ala Leu Gly
385                 390                 395                 400

Val Leu Leu His Gly Asp Ala Ala Phe Ala Gly Gln Gly Val Val Tyr
                405                 410                 415

Glu Thr Met Gly Phe Leu Thr Leu Pro Glu Tyr Ser Thr Gly Gly Thr
            420                 425                 430

Ile His Val Ile Thr Asn Asn Gln Ile Gly Phe Thr Thr Asp Pro Arg
        435                 440                 445

Phe Ala Arg Ser Thr Pro Tyr Pro Ser Asp Leu Ala Lys Ala Ile Asp
    450                 455                 460

Ala Pro Ile Phe His Val Asn Ala Asn Asp Val Glu Ala Val Thr Phe
465                 470                 475                 480

Ile Phe Asn Leu Ala Ala Glu Trp Arg His Lys Phe His Thr Asp Ala
                485                 490                 495

Ile Ile Asp Val Val Gly Trp Arg Lys His Gly His Asn Glu Thr Asp
            500                 505                 510

Gln Pro Ser Phe Thr Gln Pro Leu Met Tyr Lys Lys Ile Ala Lys Gln
        515                 520                 525

Lys Ser Val Ile Asp Val Tyr Thr Glu Lys Leu Ile Ser Glu Gly Thr
    530                 535                 540

Phe Ser Lys Lys Asp Ile Asp Glu His Lys Lys Trp Val Trp Asn Leu
545                 550                 555                 560

Phe Glu Asp Ala Phe Glu Lys Ala Lys Asp Tyr Val Pro Ser Gln Arg
                565                 570                 575

Glu Trp Leu Thr Ala Ala Trp Glu Gly Phe Lys Ser Pro Lys Glu Leu
            580                 585                 590

Ala Thr Glu Ile Leu Pro His Glu Pro Thr Asn Val Pro Glu Ser Thr
        595                 600                 605

Leu Lys Glu Leu Gly Lys Val Leu Ser Ser Trp Pro Glu Gly Phe Glu
```

```
                610             615             620
Val His Lys Asn Leu Lys Arg Ile Leu Lys Asn Arg Gly Lys Ser Ile
625             630             635             640

Glu Thr Gly Glu Gly Ile Asp Trp Ala Thr Gly Ala Leu Ala Phe
                645             650             655

Gly Thr Leu Val Leu Asp Gly Gln Asn Val Arg Val Ser Gly Glu Asp
            660             665             670

Val Glu Arg Gly Thr Phe Ser Gln Arg His Ala Val Leu His Asp Gln
        675             680             685

Gln Ser Glu Ala Ile Tyr Thr Pro Leu Ser Thr Leu Asn Asn Glu Lys
    690             695             700

Ala Asp Phe Thr Ile Ala Asn Ser Ser Leu Ser Glu Tyr Gly Val Met
705             710             715             720

Gly Phe Glu Tyr Gly Tyr Ser Leu Thr Ser Pro Asp Tyr Leu Val Met
                725             730             735

Trp Glu Ala Gln Phe Gly Asp Phe Ala Asn Thr Ala Gln Val Ile Ile
            740             745             750

Asp Gln Phe Ile Ala Gly Gly Glu Gln Lys Trp Lys Gln Arg Ser Gly
        755             760             765

Leu Val Leu Ser Leu Pro His Gly Tyr Asp Gly Gln Gly Pro Glu His
    770             775             780

Ser Ser Gly Arg Leu Glu Arg Phe Leu Gln Leu Ala Asn Glu Asp Pro
785             790             795             800

Arg Tyr Phe Pro Ser Glu Glu Lys Leu Gln Arg Gln His Gln Asp Cys
                805             810             815

Asn Phe Gln Val Val Tyr Pro Thr Thr Pro Ala Asn Leu Phe His Ile
            820             825             830

Leu Arg Arg Gln Gln His Arg Gln Phe Arg Lys Pro Leu Ala Leu Phe
        835             840             845

Phe Ser Lys Gln Leu Leu Arg His Pro Leu Ala Arg Ser Ser Leu Ser
    850             855             860

Glu Phe Thr Glu Gly Gly Phe Gln Trp Ile Ile Glu Asp Ile Glu His
865             870             875             880

Gly Lys Ser Ile Gly Thr Lys Glu Glu Thr Lys Arg Leu Val Leu Leu
                885             890             895

Ser Gly Gln Val Tyr Thr Ala Leu His Lys Arg Arg Glu Ser Leu Gly
            900             905             910

Asp Lys Thr Thr Ala Phe Leu Lys Ile Glu Gln Leu His Pro Phe Pro
        915             920             925

Phe Ala Gln Leu Arg Asp Ser Leu Asn Ser Tyr Pro Asn Leu Glu Glu
    930             935             940

Ile Val Trp Cys Gln Glu Glu Pro Leu Asn Met Gly Ser Trp Ala Tyr
945             950             955             960

Thr Glu Pro Arg Leu His Thr Thr Leu Lys Glu Thr Asp Lys Tyr Lys
                965             970             975

Asp Phe Lys Val Arg Tyr Cys Gly Arg Asn Pro Ser Gly Ala Val Ala
            980             985             990

Ala Gly Ser Lys Ser Leu His Leu Ala Glu Glu Asp Ala Phe Leu Lys
        995             1000            1005

Asp Val Phe Gln Gln Ser
    1010
```

<210> SEQ ID NO 8

```
<211> LENGTH: 499
<212> TYPE: PRT
<213> ORGANISM: Delftia acidovorans

<400> SEQUENCE: 8
```

| | | | | | | | | | | | | | | |
|---|---|---|---|---|---|---|---|---|---|---|---|---|---|---|
| Met | Leu | Arg | Ile | Arg | Ser | Leu | Leu | Asn | Asn | Lys | Arg | Ala | Phe | Ser | Ser |
| 1 | | | | 5 | | | | | 10 | | | | | 15 | |

| Thr | Val | Arg | Thr | Leu | Thr | Ile | Asn | Lys | Ser | His | Asp | Val | Val | Ile | Ile |
|---|---|---|---|---|---|---|---|---|---|---|---|---|---|---|---|
| | | 20 | | | | | 25 | | | | | 30 | | | |

| Gly | Gly | Gly | Pro | Ala | Gly | Tyr | Val | Ala | Ile | Lys | Ala | Ala | Gln | Leu |
|---|---|---|---|---|---|---|---|---|---|---|---|---|---|---|
| | | 35 | | | | | 40 | | | | 45 | | | |

| Gly | Phe | Asn | Thr | Ala | Cys | Val | Glu | Lys | Arg | Gly | Lys | Leu | Gly | Gly | Thr |
|---|---|---|---|---|---|---|---|---|---|---|---|---|---|---|---|
| | 50 | | | | | 55 | | | | | 60 | | | | |

| Cys | Leu | Asn | Val | Gly | Cys | Ile | Pro | Ser | Lys | Ala | Leu | Leu | Asn | Asn | Ser |
|---|---|---|---|---|---|---|---|---|---|---|---|---|---|---|---|
| 65 | | | | | 70 | | | | | 75 | | | | | 80 |

| His | Leu | Phe | His | Gln | Met | His | Thr | Glu | Ala | Gln | Lys | Arg | Gly | Ile | Asp |
|---|---|---|---|---|---|---|---|---|---|---|---|---|---|---|---|
| | | | | 85 | | | | | 90 | | | | | 95 | |

| Val | Asn | Gly | Asp | Ile | Lys | Ile | Asn | Val | Ala | Asn | Phe | Gln | Lys | Ala | Lys |
|---|---|---|---|---|---|---|---|---|---|---|---|---|---|---|---|
| | | | 100 | | | | | 105 | | | | | 110 | | |

| Asp | Asp | Ala | Val | Lys | Gln | Leu | Thr | Gly | Gly | Ile | Glu | Leu | Leu | Phe | Lys |
|---|---|---|---|---|---|---|---|---|---|---|---|---|---|---|---|
| | | 115 | | | | | 120 | | | | | 125 | | | |

| Lys | Asn | Lys | Val | Thr | Tyr | Tyr | Lys | Gly | Asn | Gly | Ser | Phe | Glu | Asp | Glu |
|---|---|---|---|---|---|---|---|---|---|---|---|---|---|---|---|
| | 130 | | | | | 135 | | | | | 140 | | | | |

| Thr | Lys | Ile | Arg | Val | Thr | Pro | Val | Asp | Gly | Leu | Glu | Gly | Thr | Val | Lys |
|---|---|---|---|---|---|---|---|---|---|---|---|---|---|---|---|
| 145 | | | | | 150 | | | | | 155 | | | | | 160 |

| Glu | Asp | His | Ile | Leu | Asp | Val | Lys | Asn | Ile | Ile | Val | Ala | Thr | Gly | Ser |
|---|---|---|---|---|---|---|---|---|---|---|---|---|---|---|---|
| | | | | 165 | | | | | 170 | | | | | 175 | |

| Glu | Val | Thr | Pro | Phe | Pro | Gly | Ile | Glu | Ile | Asp | Glu | Glu | Lys | Ile | Val |
|---|---|---|---|---|---|---|---|---|---|---|---|---|---|---|---|
| | | | 180 | | | | | 185 | | | | | 190 | | |

| Ser | Ser | Thr | Gly | Ala | Leu | Ser | Leu | Lys | Glu | Ile | Pro | Lys | Arg | Leu | Thr |
|---|---|---|---|---|---|---|---|---|---|---|---|---|---|---|---|
| | | 195 | | | | | 200 | | | | | 205 | | | |

| Ile | Ile | Gly | Gly | Gly | Ile | Ile | Gly | Leu | Glu | Met | Gly | Ser | Val | Tyr | Ser |
|---|---|---|---|---|---|---|---|---|---|---|---|---|---|---|---|
| | 210 | | | | | 215 | | | | | 220 | | | | |

| Arg | Leu | Gly | Ser | Lys | Val | Thr | Val | Val | Glu | Phe | Gln | Pro | Gln | Ile | Gly |
|---|---|---|---|---|---|---|---|---|---|---|---|---|---|---|---|
| 225 | | | | | 230 | | | | | 235 | | | | | 240 |

| Ala | Ser | Met | Asp | Gly | Glu | Val | Ala | Lys | Ala | Thr | Gln | Lys | Phe | Leu | Lys |
|---|---|---|---|---|---|---|---|---|---|---|---|---|---|---|---|
| | | | 245 | | | | | 250 | | | | | 255 | | |

| Lys | Gln | Gly | Leu | Asp | Phe | Lys | Leu | Ser | Thr | Lys | Val | Ile | Ser | Ala | Lys |
|---|---|---|---|---|---|---|---|---|---|---|---|---|---|---|---|
| | | 260 | | | | | 265 | | | | | 270 | | | |

| Arg | Asn | Asp | Asp | Lys | Asn | Val | Val | Glu | Ile | Val | Val | Glu | Asp | Thr | Lys |
|---|---|---|---|---|---|---|---|---|---|---|---|---|---|---|---|
| | 275 | | | | | 280 | | | | | 285 | | | | |

| Thr | Asn | Lys | Gln | Glu | Asn | Leu | Glu | Ala | Glu | Val | Leu | Leu | Val | Ala | Val |
|---|---|---|---|---|---|---|---|---|---|---|---|---|---|---|---|
| 290 | | | | | 295 | | | | | 300 | | | | | |

| Gly | Arg | Arg | Pro | Tyr | Ile | Ala | Gly | Leu | Gly | Ala | Glu | Lys | Ile | Gly | Leu |
|---|---|---|---|---|---|---|---|---|---|---|---|---|---|---|---|
| 305 | | | | 310 | | | | | 315 | | | | | 320 | |

| Glu | Val | Asp | Lys | Arg | Gly | Arg | Leu | Val | Ile | Asp | Gln | Phe | Asn | Ser |
|---|---|---|---|---|---|---|---|---|---|---|---|---|---|---|
| | | | 325 | | | | | 330 | | | | | 335 | |

| Lys | Phe | Pro | His | Ile | Lys | Val | Val | Gly | Asp | Val | Thr | Phe | Gly | Pro | Met |
|---|---|---|---|---|---|---|---|---|---|---|---|---|---|---|---|
| | | | 340 | | | | | 345 | | | | | 350 | | |

| Leu | Ala | His | Lys | Ala | Glu | Glu | Gly | Ile | Ala | Ala | Val | Glu | Met | Leu |
|---|---|---|---|---|---|---|---|---|---|---|---|---|---|---|
| | | 355 | | | | | 360 | | | | | 365 | | |

| Lys | Thr | Gly | His | Gly | His | Val | Asn | Tyr | Asn | Asn | Ile | Pro | Ser | Val | Met |
|---|---|---|---|---|---|---|---|---|---|---|---|---|---|---|---|
| | 370 | | | | | 375 | | | | | 380 | | | | |

| Tyr | Ser | His | Pro | Glu | Val | Ala | Trp | Val | Gly | Lys | Thr | Glu | Glu | Gln | Leu |
|---|---|---|---|---|---|---|---|---|---|---|---|---|---|---|---|

```
385                 390                 395                 400
Lys Glu Ala Gly Ile Asp Tyr Lys Ile Gly Lys Phe Pro Phe Ala Ala
                405                 410                 415

Asn Ser Arg Ala Lys Thr Asn Gln Asp Thr Glu Gly Phe Val Lys Ile
                420                 425                 430

Leu Ile Asp Ser Lys Thr Glu Arg Ile Leu Gly Ala His Ile Ile Gly
                435                 440                 445

Pro Asn Ala Gly Glu Met Ile Ala Glu Ala Gly Leu Ala Leu Glu Tyr
    450                 455                 460

Gly Ala Ser Ala Glu Asp Val Ala Arg Val Cys His Ala His Pro Thr
465                 470                 475                 480

Leu Ser Glu Ala Phe Lys Glu Ala Asn Met Ala Ala Tyr Asp Lys Ala
                485                 490                 495

Ile His Cys

<210> SEQ ID NO 9
<211> LENGTH: 427
<212> TYPE: PRT
<213> ORGANISM: Saccharomyces cerevisiae

<400> SEQUENCE: 9

Met Tyr Ser Arg Lys Ser Leu Ser Leu Ile Ser Lys Cys Gly Gln Leu
1               5                   10                  15

Ser Arg Leu Asn Ala Gln Ala Ala Leu Gln Ala Arg Arg His Leu Ser
                20                  25                  30

Ile His Glu Tyr Arg Ser Ala Gln Leu Leu Arg Glu Tyr Gly Ile Gly
            35                  40                  45

Thr Pro Glu Gly Phe Pro Ala Phe Thr Pro Glu Glu Ala Phe Glu Ala
        50                  55                  60

Ala Lys Lys Leu Asn Thr Asn Lys Leu Val Ile Lys Ala Gln Ala Leu
65                  70                  75                  80

Thr Gly Gly Arg Gly Lys Gly His Phe Asp Thr Gly Tyr Lys Ser Gly
                85                  90                  95

Val His Met Ile Glu Ser Pro Gln Gln Ala Glu Asp Val Ala Lys Glu
                100                 105                 110

Met Leu Asn His Asn Leu Ile Thr Lys Gln Thr Gly Ile Ala Gly Lys
                115                 120                 125

Pro Val Ser Ala Val Tyr Ile Val Lys Arg Val Asp Thr Lys His Glu
    130                 135                 140

Ala Tyr Leu Ser Ile Leu Met Asp Arg Gln Thr Lys Lys Pro Met Ile
145                 150                 155                 160

Ile Ala Ser Ser Gln Gly Gly Met Asn Ile Glu Glu Val Ala Glu Arg
                165                 170                 175

Thr Pro Asp Ala Ile Lys Lys Phe Ser Ile Glu Thr Ser Lys Gly Leu
                180                 185                 190

Ser Pro Gln Met Ala Lys Asp Val Ala Lys Ser Leu Gly Phe Ser Pro
                195                 200                 205

Asp Ala Gln Asp Glu Ala Ala Lys Ala Val Ser Asn Leu Tyr Lys Ile
    210                 215                 220

Phe Met Glu Arg Asp Ala Thr Gln Val Glu Ile Asn Pro Leu Ser Glu
225                 230                 235                 240

Ile Glu His Asp Pro Thr His Lys Ile Met Cys Thr Asp Ala Lys Phe
                245                 250                 255

Gly Phe Asp Asp Asn Ala Ser Phe Arg Gln Glu Lys Ile Tyr Ser Trp
```

```
                    260                 265                 270
Arg Asp Leu Ser Gln Glu Asp Pro Asp Glu Val Lys Ala Lys Lys Tyr
            275                 280                 285

Asp Leu Asn Phe Val Lys Leu Lys Gly Asn Ile Gly Cys Leu Val Asn
            290                 295                 300

Gly Ala Gly Leu Ala Met Ala Thr Met Asp Val Ile Lys Leu Asn Gly
305                 310                 315                 320

Gly Asp Pro Ala Asn Phe Leu Asp Cys Gly Gly Ala Thr Pro Glu
            325                 330                 335

Thr Ile Lys Gln Gly Phe Glu Leu Ile Leu Ser Asn Lys Asn Val Asp
            340                 345                 350

Ala Ile Phe Val Asn Ile Phe Gly Gly Ile Val Arg Cys Asp Tyr Val
            355                 360                 365

Ala Leu Gly Leu Val Glu Ala Ala Arg Glu Leu Glu Val Arg Val Pro
            370                 375                 380

Ile Val Ala Arg Leu Gln Gly Thr Lys Val Glu Glu Gly Arg Asp Ile
385                 390                 395                 400

Ile Asn Lys Ser Gly Val Lys Ile Tyr Ser Phe Asp Glu Leu Asp Pro
            405                 410                 415

Ala Ala Lys Lys Val Val Glu Leu Thr Gln Asn
            420                 425

<210> SEQ ID NO 10
<211> LENGTH: 329
<212> TYPE: PRT
<213> ORGANISM: Saccharomyces cerevisiae

<400> SEQUENCE: 10

Met Leu Arg Ser Thr Val Ser Lys Ala Ser Leu Lys Ile Cys Arg His
1               5                   10                  15

Phe His Arg Glu Ser Ile Pro Tyr Asp Lys Thr Ile Lys Asn Leu Leu
            20                  25                  30

Leu Pro Lys Asp Thr Lys Val Ile Phe Gln Gly Phe Thr Gly Lys Gln
            35                  40                  45

Gly Thr Phe His Ala Ser Ile Ser Gln Glu Tyr Gly Thr Asn Val Val
            50                  55                  60

Gly Gly Thr Asn Pro Lys Lys Ala Gly Gln Thr His Leu Gly Gln Pro
65                  70                  75                  80

Val Phe Ala Ser Val Lys Asp Ala Ile Lys Glu Thr Gly Ala Thr Ala
            85                  90                  95

Ser Ala Ile Phe Val Pro Pro Ile Ala Ala Ala Ile Lys Glu
            100                 105                 110

Ser Ile Glu Ala Glu Ile Pro Leu Ala Val Cys Ile Thr Glu Gly Ile
            115                 120                 125

Pro Gln His Asp Met Leu Tyr Ile Ala Glu Met Leu Gln Thr Gln Asp
            130                 135                 140

Lys Thr Arg Leu Val Gly Pro Asn Cys Pro Gly Ile Ile Asn Pro Ala
145                 150                 155                 160

Thr Lys Val Arg Ile Gly Ile Gln Pro Pro Lys Ile Phe Gln Ala Gly
            165                 170                 175

Lys Ile Gly Ile Ile Ser Arg Ser Gly Thr Leu Thr Tyr Glu Ala Val
            180                 185                 190

Gln Gln Thr Thr Lys Thr Asp Leu Gly Gln Ser Leu Val Ile Gly Met
            195                 200                 205
```

```
Gly Gly Asp Ala Phe Pro Gly Thr Asp Phe Ile Asp Ala Leu Lys Leu
            210                 215                 220

Phe Leu Glu Asp Glu Thr Thr Glu Gly Ile Ile Met Leu Gly Glu Ile
225                 230                 235                 240

Gly Gly Lys Ala Glu Ile Glu Ala Ala Gln Phe Leu Lys Glu Tyr Asn
            245                 250                 255

Phe Ser Arg Ser Lys Pro Met Pro Val Ala Ser Phe Ile Ala Gly Thr
            260                 265                 270

Val Ala Gly Gln Met Lys Gly Val Arg Met Gly His Ser Gly Ala Ile
            275                 280                 285

Val Glu Gly Ser Gly Thr Asp Ala Glu Ser Lys Lys Gln Ala Leu Arg
            290                 295                 300

Asp Val Gly Val Ala Val Val Glu Ser Pro Gly Tyr Leu Gly Gln Ala
305                 310                 315                 320

Leu Leu Asp Gln Phe Ala Lys Phe Lys
            325
```

<210> SEQ ID NO 11
<211> LENGTH: 640
<212> TYPE: PRT
<213> ORGANISM: Saccharomyces cerevisiae

<400> SEQUENCE: 11

```
Met Leu Ser Leu Lys Lys Ser Ala Leu Ser Lys Leu Thr Leu Leu Arg
1               5                   10                  15

Asn Thr Arg Thr Phe Thr Ser Ser Ala Leu Val Arg Gln Thr Gln Gly
            20                  25                  30

Ser Val Asn Gly Ser Ala Ser Arg Ser Ala Asp Gly Lys Tyr His Ile
            35                  40                  45

Ile Asp His Glu Tyr Asp Cys Val Val Ile Gly Ala Gly Gly Ala Gly
        50                  55                  60

Leu Arg Ala Ala Phe Gly Leu Ala Glu Ala Gly Tyr Lys Thr Ala Cys
65                  70                  75                  80

Ile Ser Lys Leu Phe Pro Thr Arg Ser His Thr Val Ala Ala Gln Gly
                85                  90                  95

Gly Ile Asn Ala Ala Leu Gly Asn Met His Lys Asp Asn Trp Lys Trp
            100                 105                 110

His Met Tyr Asp Thr Val Lys Gly Ser Asp Trp Leu Gly Asp Gln Asp
            115                 120                 125

Ser Ile His Tyr Met Thr Arg Glu Ala Pro Lys Ser Ile Ile Glu Leu
        130                 135                 140

Glu His Tyr Gly Val Pro Phe Ser Arg Thr Glu Asn Gly Lys Ile Tyr
145                 150                 155                 160

Gln Arg Ala Phe Gly Gly Gln Thr Lys Glu Tyr Gly Lys Gly Ala Gln
                165                 170                 175

Ala Tyr Arg Thr Cys Ala Val Ala Asp Arg Thr Gly His Ala Leu Leu
            180                 185                 190

His Thr Leu Tyr Gly Gln Ala Leu Arg His Asp Thr His Phe Phe Ile
            195                 200                 205

Glu Tyr Phe Ala Leu Asp Leu Leu Thr His Asn Gly Glu Val Val Gly
        210                 215                 220

Val Ile Ala Tyr Asn Gln Glu Asp Gly Thr Ile His Arg Phe Arg Ala
225                 230                 235                 240

His Lys Thr Ile Ile Ala Thr Gly Gly Tyr Gly Arg Ala Tyr Phe Ser
                245                 250                 255
```

-continued

Cys Thr Ser Ala His Thr Cys Thr Gly Asp Gly Asn Ala Met Val Ser
            260                 265                 270

Arg Ala Gly Phe Pro Leu Gln Asp Leu Glu Phe Val Gln Phe His Pro
        275                 280                 285

Ser Gly Ile Tyr Gly Ser Gly Cys Leu Ile Thr Glu Gly Ala Arg Gly
    290                 295                 300

Glu Gly Gly Phe Leu Val Asn Ser Gly Glu Arg Phe Met Glu Arg
305                 310                 315                 320

Tyr Ala Pro Thr Ala Lys Asp Leu Ala Cys Arg Asp Val Val Ser Arg
                325                 330                 335

Ala Ile Thr Met Glu Ile Arg Glu Gly Arg Gly Val Gly Lys Lys Lys
            340                 345                 350

Asp His Met Tyr Leu Gln Leu Ser His Leu Pro Pro Glu Val Leu Lys
        355                 360                 365

Glu Arg Leu Pro Gly Ile Ser Glu Thr Ala Ala Ile Phe Ala Gly Val
    370                 375                 380

Asp Val Thr Lys Glu Pro Ile Pro Ile Ile Pro Thr Val His Tyr Asn
385                 390                 395                 400

Met Gly Gly Ile Pro Thr Lys Trp Asn Gly Glu Ala Leu Thr Ile Asp
                405                 410                 415

Glu Glu Thr Gly Glu Asp Lys Val Ile Pro Gly Leu Met Ala Cys Gly
            420                 425                 430

Glu Ala Ala Cys Val Ser Val His Gly Ala Asn Arg Leu Gly Ala Asn
        435                 440                 445

Ser Leu Leu Asp Leu Val Val Phe Gly Arg Ala Val Ala His Thr Val
    450                 455                 460

Ala Asp Thr Leu Gln Pro Gly Leu Pro His Lys Pro Leu Pro Ser Asp
465                 470                 475                 480

Leu Gly Lys Glu Ser Ile Ala Asn Leu Asp Lys Leu Arg Asn Ala Asn
                485                 490                 495

Gly Ser Arg Ser Thr Ala Glu Ile Arg Met Asn Met Lys Gln Thr Met
            500                 505                 510

Gln Lys Asp Val Ser Val Phe Arg Thr Gln Ser Ser Leu Asp Glu Gly
        515                 520                 525

Val Arg Asn Ile Thr Ala Val Glu Lys Thr Phe Asp Asp Val Lys Thr
    530                 535                 540

Thr Asp Arg Ser Met Ile Trp Asn Ser Asp Leu Val Glu Thr Leu Glu
545                 550                 555                 560

Leu Gln Asn Leu Leu Thr Cys Ala Ser Gln Thr Ala Val Ser Ala Ala
                565                 570                 575

Asn Arg Lys Glu Ser Arg Gly Ala His Ala Arg Glu Asp Tyr Pro Asn
            580                 585                 590

Arg Asp Asp Glu His Trp Met Lys His Thr Leu Ser Trp Gln Lys Asp
        595                 600                 605

Val Ala Ala Pro Val Thr Leu Lys Tyr Arg Arg Val Ile Asp His Thr
    610                 615                 620

Leu Asp Glu Lys Glu Cys Pro Ser Val Pro Pro Thr Val Arg Ala Tyr
625                 630                 635                 640

<210> SEQ ID NO 12
<211> LENGTH: 266
<212> TYPE: PRT
<213> ORGANISM: Saccharomyces cerevisiae

<400> SEQUENCE: 12

```
Met Leu Asn Val Leu Leu Arg Arg Lys Ala Phe Cys Leu Val Thr Lys
1               5                   10                  15

Lys Gly Met Ala Thr Ala Thr Ala Ala Thr His Thr Pro Arg
            20                  25                  30

Leu Lys Thr Phe Lys Val Tyr Arg Trp Asn Pro Asp Glu Pro Ser Ala
                35                  40                  45

Lys Pro His Leu Gln Ser Tyr Gln Val Asp Leu Asn Asp Cys Gly Pro
        50                  55                  60

Met Val Leu Asp Ala Leu Leu Lys Ile Lys Asp Glu Gln Asp Ser Thr
65                  70                  75                  80

Leu Thr Phe Arg Arg Ser Cys Arg Glu Gly Ile Cys Gly Ser Cys Ala
                85                  90                  95

Met Asn Ile Gly Gly Arg Asn Thr Leu Ala Cys Ile Cys Lys Ile Asp
            100                 105                 110

Gln Asn Glu Ser Lys Gln Leu Lys Ile Tyr Pro Leu Pro His Met Phe
        115                 120                 125

Ile Val Lys Asp Leu Val Pro Asp Leu Thr Asn Phe Tyr Gln Gln Tyr
    130                 135                 140

Lys Ser Ile Gln Pro Tyr Leu Gln Arg Ser Ser Phe Pro Lys Asp Gly
145                 150                 155                 160

Thr Glu Val Leu Gln Ser Ile Glu Asp Arg Lys Lys Leu Asp Gly Leu
                165                 170                 175

Tyr Glu Cys Ile Leu Cys Ala Cys Cys Ser Thr Ser Cys Pro Ser Tyr
            180                 185                 190

Trp Trp Asn Gln Glu Gln Tyr Leu Gly Pro Ala Val Leu Met Gln Ala
        195                 200                 205

Tyr Arg Trp Leu Ile Asp Ser Arg Asp Gln Ala Thr Lys Thr Arg Lys
    210                 215                 220

Ala Met Leu Asn Asn Ser Met Ser Leu Tyr Arg Cys His Thr Ile Met
225                 230                 235                 240

Asn Cys Thr Arg Thr Cys Pro Lys Gly Leu Asn Pro Gly Leu Ala Ile
                245                 250                 255

Ala Glu Ile Lys Lys Ser Leu Ala Phe Ala
            260                 265
```

<210> SEQ ID NO 13
<211> LENGTH: 198
<212> TYPE: PRT
<213> ORGANISM: Saccharomyces cerevisiae

<400> SEQUENCE: 13

```
Met Ser Ala Met Met Val Lys Leu Gly Leu Asn Lys Ser Ala Leu Leu
1               5                   10                  15

Leu Lys Pro Ser Ala Phe Ser Arg Ala Ala Leu Ser Ser Ser Arg
            20                  25                  30

Arg Leu Leu Phe Asn Thr Ala Arg Thr Asn Phe Leu Ser Thr Ser Pro
                35                  40                  45

Leu Lys Asn Val Ala Ser Glu Met Asn Thr Lys Ala Ala Ile Ala Glu
        50                  55                  60

Glu Gln Ile Leu Asn Lys Gln Arg Ala Lys Arg Pro Ile Ser Pro His
65                  70                  75                  80

Leu Thr Ile Tyr Gln Pro Gln Leu Thr Trp Tyr Leu Ser Ser Leu His
                85                  90                  95
```

-continued

```
Arg Ile Ser Leu Val Leu Met Gly Leu Gly Phe Tyr Leu Phe Thr Ile
                100                 105                 110

Leu Phe Gly Val Ser Gly Leu Leu Gly Leu Gly Leu Thr Thr Glu Lys
            115                 120                 125

Val Ser Asn Trp Tyr His Gln Lys Phe Ser Lys Ile Thr Glu Trp Ser
        130                 135                 140

Ile Lys Gly Ser Phe Ala Tyr Leu Phe Ala Ile His Tyr Gly Gly Ala
145                 150                 155                 160

Ile Arg His Leu Ile Trp Asp Thr Ala Lys Glu Leu Thr Leu Lys Gly
                165                 170                 175

Val Tyr Arg Thr Gly Tyr Ala Leu Ile Gly Phe Thr Ala Val Leu Gly
            180                 185                 190

Thr Tyr Leu Leu Thr Leu
        195

<210> SEQ ID NO 14
<211> LENGTH: 488
<212> TYPE: PRT
<213> ORGANISM: Saccharomyces cerevisiae

<400> SEQUENCE: 14

Met Leu Arg Phe Thr Asn Cys Ser Cys Lys Thr Phe Val Lys Ser Ser
1               5                   10                  15

Tyr Lys Leu Asn Ile Arg Arg Met Asn Ser Ser Phe Arg Thr Glu Thr
                20                  25                  30

Asp Ala Phe Gly Glu Ile His Val Pro Ala Asp Lys Tyr Trp Gly Ala
            35                  40                  45

Gln Thr Gln Arg Ser Phe Gln Asn Phe Lys Ile Gly Gly Ala Arg Glu
        50                  55                  60

Arg Met Pro Leu Pro Leu Val His Ala Phe Gly Val Leu Lys Lys Ser
65                  70                  75                  80

Ala Ala Ile Val Asn Glu Ser Leu Gly Gly Leu Asp Pro Lys Ile Ser
                85                  90                  95

Lys Ala Ile Gln Gln Ala Ala Asp Glu Val Ala Ser Gly Lys Leu Asp
                100                 105                 110

Asp His Phe Pro Leu Val Val Phe Gln Thr Gly Ser Gly Thr Gln Ser
            115                 120                 125

Asn Met Asn Ala Asn Glu Val Ile Ser Asn Arg Ala Ile Glu Ile Leu
        130                 135                 140

Gly Gly Lys Ile Gly Ser Lys Gln Val His Pro Asn Asn His Cys Asn
145                 150                 155                 160

Gln Ser Gln Ser Ser Asn Asp Thr Phe Pro Thr Val Met His Ile Ala
                165                 170                 175

Ala Ser Leu Gln Ile Gln Asn Glu Leu Ile Pro Glu Leu Thr Asn Leu
            180                 185                 190

Lys Asn Ala Leu Glu Ala Lys Ser Lys Glu Phe Asp His Ile Val Lys
        195                 200                 205

Ile Gly Arg Thr His Leu Gln Asp Ala Thr Pro Leu Thr Leu Gly Gln
    210                 215                 220

Glu Phe Ser Gly Tyr Val Gln Gln Val Glu Asn Gly Ile Gln Arg Val
225                 230                 235                 240

Ala His Ser Leu Lys Thr Leu Ser Phe Leu Ala Gln Gly Gly Thr Ala
                245                 250                 255

Val Gly Thr Gly Leu Asn Thr Lys Pro Gly Phe Asp Val Lys Ile Ala
            260                 265                 270
```

```
Glu Gln Ile Ser Lys Glu Thr Gly Leu Lys Phe Gln Thr Ala Pro Asn
            275                 280                 285

Lys Phe Glu Ala Leu Ala Ala His Asp Ala Ile Val Glu Cys Ser Gly
        290                 295                 300

Ala Leu Asn Thr Leu Ala Cys Ser Leu Phe Lys Ile Ala Gln Asp Ile
305                 310                 315                 320

Arg Tyr Leu Gly Ser Gly Pro Arg Cys Gly Tyr His Glu Leu Met Leu
                325                 330                 335

Pro Glu Asn Glu Pro Gly Ser Ser Ile Met Pro Gly Lys Val Asn Pro
            340                 345                 350

Thr Gln Asn Glu Ala Leu Thr Gln Val Cys Val Gln Val Met Gly Asn
        355                 360                 365

Asn Ala Ala Ile Thr Phe Ala Gly Ser Gln Gly Gln Phe Glu Leu Asn
370                 375                 380

Val Phe Lys Pro Val Met Ile Ala Asn Leu Leu Asn Ser Ile Arg Leu
385                 390                 395                 400

Ile Thr Asp Ala Ala Tyr Ser Phe Arg Val His Cys Val Glu Gly Ile
                405                 410                 415

Lys Ala Asn Glu Pro Arg Ile His Glu Leu Leu Thr Lys Ser Leu Met
            420                 425                 430

Leu Val Thr Ala Leu Asn Pro Lys Ile Gly Tyr Asp Ala Ala Ser Lys
        435                 440                 445

Val Ala Lys Asn Ala His Lys Lys Gly Ile Thr Leu Lys Glu Ser Ala
450                 455                 460

Leu Glu Leu Gly Val Leu Thr Glu Lys Glu Phe Asp Glu Trp Val Val
465                 470                 475                 480

Pro Glu His Met Leu Gly Pro Lys
                485

<210> SEQ ID NO 15
<211> LENGTH: 343
<212> TYPE: PRT
<213> ORGANISM: Saccharomyces cerevisiae

<400> SEQUENCE: 15

Met Val Lys Val Ala Ile Leu Gly Ala Ser Gly Gly Val Gly Gln Pro
1               5                   10                  15

Leu Ser Leu Leu Leu Lys Leu Ser Pro Tyr Val Ser Glu Leu Ala Leu
            20                  25                  30

Tyr Asp Ile Arg Ala Ala Glu Gly Ile Gly Lys Asp Leu Ser His Ile
        35                  40                  45

Asn Thr Asn Ser Ser Cys Val Gly Tyr Asp Lys Asp Ser Ile Glu Asn
50                  55                  60

Thr Leu Ser Asn Ala Gln Val Val Leu Ile Pro Ala Gly Val Pro Arg
65                  70                  75                  80

Lys Pro Gly Leu Thr Arg Asp Asp Leu Phe Lys Met Asn Ala Gly Ile
                85                  90                  95

Val Lys Ser Leu Val Thr Ala Val Gly Lys Phe Ala Pro Asn Ala Arg
            100                 105                 110

Ile Leu Val Ile Ser Asn Pro Val Asn Ser Leu Val Pro Ile Ala Val
        115                 120                 125

Glu Thr Leu Lys Lys Met Gly Lys Phe Lys Pro Gly Asn Val Met Gly
    130                 135                 140

Val Thr Asn Leu Asp Leu Val Arg Ala Glu Thr Phe Leu Val Asp Tyr
```

```
                145                 150                 155                 160
Leu Met Leu Lys Asn Pro Lys Ile Gly Gln Glu Gln Asp Lys Thr Thr
                    165                 170                 175

Met His Arg Lys Val Thr Val Ile Gly Gly His Ser Gly Glu Thr Ile
                    180                 185                 190

Ile Pro Ile Ile Thr Asp Lys Ser Leu Val Phe Gln Leu Asp Lys Gln
                    195                 200                 205

Tyr Glu His Phe Ile His Arg Val Gln Phe Gly Gly Asp Glu Ile Val
                    210                 215                 220

Lys Ala Lys Gln Gly Ala Gly Ser Ala Thr Leu Ser Met Ala Phe Ala
225                 230                 235                 240

Gly Ala Lys Phe Ala Glu Glu Val Leu Arg Ser Phe His Asn Glu Lys
                    245                 250                 255

Pro Glu Thr Glu Ser Leu Ser Ala Phe Val Tyr Leu Pro Gly Leu Lys
                    260                 265                 270

Asn Gly Lys Lys Ala Gln Gln Leu Val Gly Asp Asn Ser Ile Glu Tyr
                    275                 280                 285

Phe Ser Leu Pro Ile Val Leu Arg Asn Gly Ser Val Val Ser Ile Asp
290                 295                 300

Thr Ser Val Leu Glu Lys Leu Ser Pro Arg Glu Gln Leu Val Asn
305                 310                 315                 320

Thr Ala Val Lys Glu Leu Arg Lys Asn Ile Lys Gly Lys Ser Phe
                    325                 330                 335

Ile Leu Asp Ser Ser Lys Leu
                    340

<210> SEQ ID NO 16
<211> LENGTH: 377
<212> TYPE: PRT
<213> ORGANISM: Saccharomyces cerevisiae

<400> SEQUENCE: 16

Met Pro His Ser Val Thr Pro Ser Ile Glu Gln Asp Ser Leu Lys Ile
1               5                   10                  15

Ala Ile Leu Gly Ala Ala Gly Gly Ile Gly Gln Ser Leu Ser Leu Leu
                20                  25                  30

Leu Lys Ala Gln Leu Gln Tyr Gln Leu Lys Glu Ser Asn Arg Ser Val
            35                  40                  45

Thr His Ile His Leu Ala Leu Tyr Asp Val Asn Gln Glu Ala Ile Asn
        50                  55                  60

Gly Val Thr Ala Asp Leu Ser His Ile Asp Thr Pro Ile Ser Val Ser
65                  70                  75                  80

Ser His Ser Pro Ala Gly Gly Ile Glu Asn Cys Leu His Asn Ala Ser
                85                  90                  95

Ile Val Val Ile Pro Ala Gly Val Pro Arg Lys Pro Gly Met Thr Arg
            100                 105                 110

Asp Asp Leu Phe Asn Val Asn Ala Gly Ile Ile Ser Gln Leu Gly Asp
        115                 120                 125

Ser Ile Ala Glu Cys Cys Asp Leu Ser Lys Val Phe Val Leu Val Ile
    130                 135                 140

Ser Asn Pro Val Asn Ser Leu Val Pro Val Met Val Ser Asn Ile Leu
145                 150                 155                 160

Lys Asn His Pro Gln Ser Arg Asn Ser Gly Ile Glu Arg Arg Ile Met
                165                 170                 175
```

```
Gly Val Thr Lys Leu Asp Ile Val Arg Ala Ser Thr Phe Leu Arg Glu
            180                 185                 190

Ile Asn Ile Glu Ser Gly Leu Thr Pro Arg Val Asn Ser Met Pro Asp
        195                 200                 205

Val Pro Val Ile Gly Gly His Ser Gly Glu Thr Ile Ile Pro Leu Phe
    210                 215                 220

Ser Gln Ser Asn Phe Leu Ser Arg Leu Asn Glu Asp Gln Leu Lys Tyr
225                 230                 235                 240

Leu Ile His Arg Val Gln Tyr Gly Gly Asp Glu Val Val Lys Ala Lys
                245                 250                 255

Asn Gly Lys Gly Ser Ala Thr Leu Ser Met Ala His Ala Gly Tyr Lys
            260                 265                 270

Cys Val Val Gln Phe Val Ser Leu Leu Leu Gly Asn Ile Glu Gln Ile
        275                 280                 285

His Gly Thr Tyr Tyr Val Pro Leu Lys Asp Ala Asn Asn Phe Pro Ile
    290                 295                 300

Ala Pro Gly Ala Asp Gln Leu Leu Pro Leu Val Asp Gly Ala Asp Tyr
305                 310                 315                 320

Phe Ala Ile Pro Leu Thr Ile Thr Thr Lys Gly Val Ser Tyr Val Asp
                325                 330                 335

Tyr Asp Ile Val Asn Arg Met Asn Asp Met Glu Arg Asn Gln Met Leu
            340                 345                 350

Pro Ile Cys Val Ser Gln Leu Lys Lys Asn Ile Asp Lys Gly Leu Glu
        355                 360                 365

Phe Val Ala Ser Arg Ser Ala Ser Ser
    370                 375

<210> SEQ ID NO 17
<211> LENGTH: 334
<212> TYPE: PRT
<213> ORGANISM: Saccharomyces cerevisiae

<400> SEQUENCE: 17

Met Leu Ser Arg Val Ala Lys Arg Ala Phe Ser Ser Thr Val Ala Asn
1               5                   10                  15

Pro Tyr Lys Val Thr Val Leu Gly Ala Gly Gly Ile Gly Gln Pro
            20                  25                  30

Leu Ser Leu Leu Leu Lys Leu Asn His Lys Val Thr Asp Leu Arg Leu
        35                  40                  45

Tyr Asp Leu Lys Gly Ala Lys Gly Val Ala Thr Asp Leu Ser His Ile
    50                  55                  60

Pro Thr Asn Ser Val Val Lys Gly Phe Thr Pro Glu Glu Pro Asp Gly
65                  70                  75                  80

Leu Asn Asn Ala Leu Lys Asp Thr Asp Met Val Leu Ile Pro Ala Gly
                85                  90                  95

Val Pro Arg Lys Pro Gly Met Thr Arg Asp Asp Leu Phe Ala Ile Asn
            100                 105                 110

Ala Ser Ile Val Arg Asp Leu Ala Ala Ala Thr Ala Glu Ser Ala Pro
        115                 120                 125

Asn Ala Ala Ile Leu Val Ile Ser Asn Pro Val Asn Ser Thr Val Pro
    130                 135                 140

Ile Val Ala Gln Val Leu Lys Asn Lys Gly Val Tyr Asn Pro Lys Lys
145                 150                 155                 160

Leu Phe Gly Val Thr Thr Leu Asp Ser Ile Arg Ala Ala Arg Phe Ile
                165                 170                 175
```

```
Ser Glu Val Glu Asn Thr Asp Pro Thr Gln Glu Arg Val Asn Val Ile
            180                 185                 190

Gly Gly His Ser Gly Ile Thr Ile Ile Pro Leu Ile Ser Gln Thr Asn
            195                 200                 205

His Lys Leu Met Ser Asp Asp Lys Arg His Glu Leu Ile His Arg Ile
            210                 215                 220

Gln Phe Gly Gly Asp Glu Val Val Lys Ala Lys Asn Gly Ala Gly Ser
225                 230                 235                 240

Ala Thr Leu Ser Met Ala His Ala Gly Ala Lys Phe Ala Asn Ala Val
                245                 250                 255

Leu Ser Gly Phe Lys Gly Glu Arg Asp Val Ile Glu Pro Ser Phe Val
            260                 265                 270

Asp Ser Pro Leu Phe Lys Ser Glu Gly Ile Glu Phe Phe Ala Ser Pro
            275                 280                 285

Val Thr Leu Gly Pro Asp Gly Ile Glu Lys Ile His Pro Ile Gly Glu
            290                 295                 300

Leu Ser Ser Glu Glu Glu Met Leu Gln Lys Cys Lys Glu Thr Leu
305                 310                 315                 320

Lys Lys Asn Ile Glu Lys Gly Val Asn Phe Val Ala Ser Lys
            325                 330

<210> SEQ ID NO 18
<211> LENGTH: 1178
<212> TYPE: PRT
<213> ORGANISM: Saccharomyces cerevisiae

<400> SEQUENCE: 18

Met Ser Gln Arg Lys Phe Ala Gly Leu Arg Asp Asn Phe Asn Leu Leu
1               5                   10                  15

Gly Glu Lys Asn Lys Ile Leu Val Ala Asn Arg Gly Glu Ile Pro Ile
            20                  25                  30

Arg Ile Phe Arg Thr Ala His Glu Leu Ser Met Gln Thr Val Ala Ile
            35                  40                  45

Tyr Ser His Glu Asp Arg Leu Ser Thr His Lys Gln Lys Ala Asp Glu
50                  55                  60

Ala Tyr Val Ile Gly Glu Val Gly Gln Tyr Thr Pro Val Gly Ala Tyr
65                  70                  75                  80

Leu Ala Ile Asp Glu Ile Ile Ser Ile Ala Gln Lys His Gln Val Asp
                85                  90                  95

Phe Ile His Pro Gly Tyr Gly Phe Leu Ser Glu Asn Ser Glu Phe Ala
            100                 105                 110

Asp Lys Val Val Lys Ala Gly Ile Thr Trp Ile Gly Pro Pro Ala Glu
            115                 120                 125

Val Ile Asp Ser Val Gly Asp Lys Val Ser Ala Arg Asn Leu Ala Ala
            130                 135                 140

Lys Ala Asn Val Pro Thr Val Pro Gly Thr Pro Gly Pro Ile Glu Thr
145                 150                 155                 160

Val Glu Glu Ala Leu Asp Phe Val Asn Glu Tyr Gly Tyr Pro Val Ile
                165                 170                 175

Ile Lys Ala Ala Phe Gly Gly Gly Gly Arg Gly Met Arg Val Val Arg
            180                 185                 190

Glu Gly Asp Asp Val Ala Asp Ala Phe Gln Arg Ala Thr Ser Glu Ala
            195                 200                 205

Arg Thr Ala Phe Gly Asn Gly Thr Cys Phe Val Glu Arg Phe Leu Asp
```

-continued

```
                210                 215                 220
Lys Pro Lys His Ile Glu Val Gln Leu Leu Ala Asp Asn His Gly Asn
225                 230                 235                 240

Val Val His Leu Phe Glu Arg Asp Cys Ser Val Gln Arg Arg His Gln
                245                 250                 255

Lys Val Val Glu Val Ala Pro Ala Lys Thr Leu Pro Arg Glu Val Arg
                260                 265                 270

Asp Ala Ile Leu Thr Asp Ala Val Lys Leu Ala Lys Glu Cys Gly Tyr
                275                 280                 285

Arg Asn Ala Gly Thr Ala Glu Phe Leu Val Asp Asn Gln Asn Arg His
                290                 295                 300

Tyr Phe Ile Glu Ile Asn Pro Arg Ile Gln Val Glu His Thr Ile Thr
305                 310                 315                 320

Glu Glu Ile Thr Gly Ile Asp Ile Val Ala Ala Gln Ile Gln Ile Ala
                325                 330                 335

Ala Gly Ala Ser Leu Pro Gln Leu Gly Leu Phe Gln Asp Lys Ile Thr
                340                 345                 350

Thr Arg Gly Phe Ala Ile Gln Cys Arg Ile Thr Thr Glu Asp Pro Ala
                355                 360                 365

Lys Asn Phe Gln Pro Asp Thr Gly Arg Ile Glu Val Tyr Arg Ser Ala
370                 375                 380

Gly Gly Asn Gly Val Arg Leu Asp Gly Gly Asn Ala Tyr Ala Gly Thr
385                 390                 395                 400

Ile Ile Ser Pro His Tyr Asp Ser Met Leu Val Lys Cys Ser Cys Ser
                405                 410                 415

Gly Ser Thr Tyr Glu Ile Val Arg Arg Lys Met Ile Arg Ala Leu Ile
                420                 425                 430

Glu Phe Arg Ile Arg Gly Val Lys Thr Asn Ile Pro Phe Leu Leu Thr
                435                 440                 445

Leu Leu Thr Asn Pro Val Phe Ile Glu Gly Thr Tyr Trp Thr Thr Phe
450                 455                 460

Ile Asp Asp Thr Pro Gln Leu Phe Gln Met Val Ser Ser Gln Asn Arg
465                 470                 475                 480

Ala Gln Lys Leu Leu His Tyr Leu Ala Asp Val Ala Val Asn Gly Ser
                485                 490                 495

Ser Ile Lys Gly Gln Ile Gly Leu Pro Lys Leu Lys Ser Asn Pro Ser
                500                 505                 510

Val Pro His Leu His Asp Ala Gln Gly Asn Val Ile Asn Val Thr Lys
                515                 520                 525

Ser Ala Pro Pro Ser Gly Trp Arg Gln Val Leu Leu Glu Lys Gly Pro
530                 535                 540

Ala Glu Phe Ala Arg Gln Val Arg Gln Phe Asn Gly Thr Leu Leu Met
545                 550                 555                 560

Asp Thr Thr Trp Arg Asp Ala His Gln Ser Leu Leu Ala Thr Arg Val
                565                 570                 575

Arg Thr His Asp Leu Ala Thr Ile Ala Pro Thr Thr Ala His Ala Leu
                580                 585                 590

Ala Gly Arg Phe Ala Leu Glu Cys Trp Gly Gly Ala Thr Phe Asp Val
                595                 600                 605

Ala Met Arg Phe Leu His Glu Asp Pro Trp Glu Arg Leu Arg Lys Leu
                610                 615                 620

Arg Ser Leu Val Pro Asn Ile Pro Phe Gln Met Leu Leu Arg Gly Ala
625                 630                 635                 640
```

```
Asn Gly Val Ala Tyr Ser Ser Leu Pro Asp Asn Ala Ile Asp His Phe
                645                 650                 655

Val Lys Gln Ala Lys Asp Asn Gly Val Asp Ile Phe Arg Val Phe Asp
                660                 665                 670

Ala Leu Asn Asp Leu Glu Gln Leu Lys Val Gly Val Asp Ala Val Lys
                675                 680                 685

Lys Ala Gly Val Val Glu Ala Thr Val Cys Phe Ser Gly Asp Met
690                 695                 700

Leu Gln Pro Gly Lys Lys Tyr Asn Leu Asp Tyr Tyr Leu Glu Ile Ala
705                 710                 715                 720

Glu Lys Ile Val Gln Met Gly Thr His Ile Leu Gly Ile Lys Asp Met
                725                 730                 735

Ala Gly Thr Met Lys Pro Ala Ala Lys Leu Leu Ile Gly Ser Leu
                740                 745                 750

Arg Ala Lys Tyr Pro Asp Leu Pro Ile His Val His Thr His Asp Ser
                755                 760                 765

Ala Gly Thr Ala Val Ala Ser Met Thr Ala Cys Ala Leu Ala Gly Ala
                770                 775                 780

Asp Val Val Asp Val Ala Ile Asn Ser Met Ser Gly Leu Thr Ser Gln
785                 790                 795                 800

Pro Ser Ile Asn Ala Leu Leu Ala Ser Leu Glu Gly Asn Ile Asp Thr
                805                 810                 815

Gly Ile Asn Val Glu His Val Arg Glu Leu Asp Ala Tyr Trp Ala Glu
                820                 825                 830

Met Arg Leu Leu Tyr Ser Cys Phe Glu Ala Asp Leu Lys Gly Pro Asp
                835                 840                 845

Pro Glu Val Tyr Gln His Glu Ile Pro Gly Gly Gln Leu Thr Asn Leu
                850                 855                 860

Leu Phe Gln Ala Gln Gln Leu Gly Leu Gly Glu Gln Trp Ala Glu Thr
865                 870                 875                 880

Lys Arg Ala Tyr Arg Glu Ala Asn Tyr Leu Leu Gly Asp Ile Val Lys
                885                 890                 895

Val Thr Pro Thr Ser Lys Val Val Gly Asp Leu Ala Gln Phe Met Val
                900                 905                 910

Ser Asn Lys Leu Thr Ser Asp Asp Val Arg Arg Leu Ala Asn Ser Leu
                915                 920                 925

Asp Phe Pro Asp Ser Val Met Asp Phe Phe Glu Gly Leu Ile Gly Gln
                930                 935                 940

Pro Tyr Gly Gly Phe Pro Glu Pro Phe Arg Ser Asp Val Leu Arg Asn
945                 950                 955                 960

Lys Arg Arg Lys Leu Thr Cys Arg Pro Gly Leu Glu Leu Glu Pro Phe
                965                 970                 975

Asp Leu Glu Lys Ile Arg Glu Asp Leu Gln Asn Arg Phe Gly Asp Val
                980                 985                 990

Asp Glu Cys Asp Val Ala Ser Tyr Asn Met Tyr Pro Arg Val Tyr Glu
                995                 1000                1005

Asp Phe Gln Lys Met Arg Glu Thr Tyr Gly Asp Leu Ser Val Leu
                1010                1015                1020

Pro Thr Arg Ser Phe Leu Ser Pro Leu Glu Thr Asp Glu Glu Ile
                1025                1030                1035

Glu Val Val Ile Glu Gln Gly Lys Thr Leu Ile Ile Lys Leu Gln
                1040                1045                1050
```

```
Ala  Val  Gly  Asp  Leu  Asn  Lys  Lys  Thr  Gly  Glu  Arg  Glu  Val  Tyr
     1055                1060                1065

Phe  Asp  Leu  Asn  Gly  Glu  Met  Arg  Lys  Ile  Arg  Val  Ala  Asp  Arg
     1070                1075                1080

Ser  Gln  Lys  Val  Glu  Thr  Val  Thr  Lys  Ser  Lys  Ala  Asp  Met  His
     1085                1090                1095

Asp  Pro  Leu  His  Ile  Gly  Ala  Pro  Met  Ala  Gly  Val  Ile  Val  Glu
     1100                1105                1110

Val  Lys  Val  His  Lys  Gly  Ser  Leu  Ile  Lys  Lys  Gly  Gln  Pro  Val
     1115                1120                1125

Ala  Val  Leu  Ser  Ala  Met  Lys  Met  Glu  Met  Ile  Ile  Ser  Ser  Pro
     1130                1135                1140

Ser  Asp  Gly  Gln  Val  Lys  Glu  Val  Phe  Val  Ser  Asp  Gly  Glu  Asn
     1145                1150                1155

Val  Asp  Ser  Ser  Asp  Leu  Leu  Val  Leu  Glu  Asp  Gln  Val  Pro
     1160                1165                1170

Val  Glu  Thr  Lys  Ala
     1175

<210> SEQ ID NO 19
<211> LENGTH: 1180
<212> TYPE: PRT
<213> ORGANISM: Saccharomyces cerevisiae

<400> SEQUENCE: 19

Met  Ser  Ser  Ser  Lys  Lys  Leu  Ala  Gly  Leu  Arg  Asp  Asn  Phe  Ser  Leu
1                 5                   10                  15

Leu  Gly  Glu  Lys  Asn  Lys  Ile  Leu  Val  Ala  Asn  Arg  Gly  Glu  Ile  Pro
                 20                  25                  30

Ile  Arg  Ile  Phe  Arg  Ser  Ala  His  Glu  Leu  Ser  Met  Arg  Thr  Ile  Ala
                 35                  40                  45

Ile  Tyr  Ser  His  Glu  Asp  Arg  Leu  Ser  Met  His  Arg  Leu  Lys  Ala  Asp
            50                  55                  60

Glu  Ala  Tyr  Val  Ile  Gly  Glu  Glu  Gly  Gln  Tyr  Thr  Pro  Val  Gly  Ala
65                  70                  75                  80

Tyr  Leu  Ala  Met  Asp  Glu  Ile  Ile  Glu  Ile  Ala  Lys  Lys  His  Lys  Val
                 85                  90                  95

Asp  Phe  Ile  His  Pro  Gly  Tyr  Gly  Phe  Leu  Ser  Glu  Asn  Ser  Glu  Phe
            100                 105                 110

Ala  Asp  Lys  Val  Val  Lys  Ala  Gly  Ile  Thr  Trp  Ile  Gly  Pro  Pro  Ala
            115                 120                 125

Glu  Val  Ile  Asp  Ser  Val  Gly  Asp  Lys  Val  Ser  Ala  Arg  His  Leu  Ala
            130                 135                 140

Ala  Arg  Ala  Asn  Val  Pro  Thr  Val  Pro  Gly  Thr  Pro  Gly  Pro  Ile  Glu
145                 150                 155                 160

Thr  Val  Gln  Glu  Ala  Leu  Asp  Phe  Val  Asn  Glu  Tyr  Gly  Tyr  Pro  Val
                 165                 170                 175

Ile  Ile  Lys  Ala  Ala  Phe  Gly  Gly  Gly  Gly  Arg  Gly  Met  Arg  Val  Val
            180                 185                 190

Arg  Glu  Gly  Asp  Asp  Val  Ala  Asp  Ala  Phe  Gln  Arg  Ala  Thr  Ser  Glu
            195                 200                 205

Ala  Arg  Thr  Ala  Phe  Gly  Asn  Gly  Thr  Cys  Phe  Val  Glu  Arg  Phe  Leu
            210                 215                 220

Asp  Lys  Pro  Lys  His  Ile  Glu  Val  Gln  Leu  Leu  Ala  Asp  Asn  His  Gly
225                 230                 235                 240
```

```
Asn Val Val His Leu Phe Glu Arg Asp Cys Ser Val Gln Arg Arg His
            245                 250                 255

Gln Lys Val Val Glu Val Ala Pro Ala Lys Thr Leu Pro Arg Glu Val
            260                 265                 270

Arg Asp Ala Ile Leu Thr Asp Ala Val Lys Leu Ala Lys Val Cys Gly
            275                 280                 285

Tyr Arg Asn Ala Gly Thr Ala Glu Phe Leu Val Asp Asn Gln Asn Arg
            290                 295                 300

His Tyr Phe Ile Glu Ile Asn Pro Arg Ile Gln Val Glu His Thr Ile
305                 310                 315                 320

Thr Glu Glu Ile Thr Gly Ile Asp Ile Val Ser Ala Gln Ile Gln Ile
            325                 330                 335

Ala Ala Gly Ala Thr Leu Thr Gln Leu Gly Leu Leu Gln Asp Lys Ile
            340                 345                 350

Thr Thr Arg Gly Phe Ser Ile Gln Cys Arg Ile Thr Thr Glu Asp Pro
            355                 360                 365

Ser Lys Asn Phe Gln Pro Asp Thr Gly Arg Leu Glu Val Tyr Arg Ser
            370                 375                 380

Ala Gly Gly Asn Gly Val Arg Leu Asp Gly Gly Asn Ala Tyr Ala Gly
385                 390                 395                 400

Ala Thr Ile Ser Pro His Tyr Asp Ser Met Leu Val Lys Cys Ser Cys
            405                 410                 415

Ser Gly Ser Thr Tyr Glu Ile Val Arg Arg Lys Met Ile Arg Ala Leu
            420                 425                 430

Ile Glu Phe Arg Ile Arg Gly Val Lys Thr Asn Ile Pro Phe Leu Leu
            435                 440                 445

Thr Leu Leu Thr Asn Pro Val Phe Ile Glu Gly Thr Tyr Trp Thr Thr
            450                 455                 460

Phe Ile Asp Asp Thr Pro Gln Leu Phe Gln Met Val Ser Ser Gln Asn
465                 470                 475                 480

Arg Ala Gln Lys Leu Leu His Tyr Leu Ala Asp Leu Ala Val Asn Gly
            485                 490                 495

Ser Ser Ile Lys Gly Gln Ile Gly Leu Pro Lys Leu Lys Ser Asn Pro
            500                 505                 510

Ser Val Pro His Leu His Asp Ala Gln Gly Asn Val Ile Asn Val Thr
            515                 520                 525

Lys Ser Ala Pro Pro Ser Gly Trp Arg Gln Val Leu Leu Glu Lys Gly
            530                 535                 540

Pro Ser Glu Phe Ala Lys Gln Val Arg Gln Phe Asn Gly Thr Leu Leu
545                 550                 555                 560

Met Asp Thr Thr Trp Arg Asp Ala His Gln Ser Leu Leu Ala Thr Arg
            565                 570                 575

Val Arg Thr His Asp Leu Ala Thr Ile Ala Pro Thr Thr Ala His Ala
            580                 585                 590

Leu Ala Gly Ala Phe Ala Leu Glu Cys Trp Gly Gly Ala Thr Phe Asp
            595                 600                 605

Val Ala Met Arg Phe Leu His Glu Asp Pro Trp Glu Arg Leu Arg Lys
            610                 615                 620

Leu Arg Ser Leu Val Pro Asn Ile Pro Phe Gln Met Leu Leu Arg Gly
625                 630                 635                 640

Ala Asn Gly Val Ala Tyr Ser Ser Leu Pro Asp Asn Ala Ile Asp His
            645                 650                 655
```

```
Phe Val Lys Gln Ala Lys Asp Asn Gly Val Asp Ile Phe Arg Val Phe
            660                 665                 670

Asp Ala Leu Asn Asp Leu Glu Gln Leu Lys Val Gly Val Asn Ala Val
        675                 680                 685

Lys Lys Ala Gly Gly Val Val Glu Ala Thr Val Cys Tyr Ser Gly Asp
    690                 695                 700

Met Leu Gln Pro Gly Lys Lys Tyr Asn Leu Asp Tyr Tyr Leu Glu Val
705                 710                 715                 720

Val Glu Lys Ile Val Gln Met Gly Thr His Ile Leu Gly Ile Lys Asp
                725                 730                 735

Met Ala Gly Thr Met Lys Pro Ala Ala Lys Leu Leu Ile Gly Ser
            740                 745                 750

Leu Arg Thr Arg Tyr Pro Asp Leu Pro Ile His Val His Ser His Asp
        755                 760                 765

Ser Ala Gly Thr Ala Val Ala Ser Met Thr Ala Cys Ala Leu Ala Gly
    770                 775                 780

Ala Asp Val Val Asp Val Ala Ile Asn Ser Met Ser Gly Leu Thr Ser
785                 790                 795                 800

Gln Pro Ser Ile Asn Ala Leu Leu Ala Ser Leu Glu Gly Asn Ile Asp
                805                 810                 815

Thr Gly Ile Asn Val Glu His Val Arg Glu Leu Asp Ala Tyr Trp Ala
            820                 825                 830

Glu Met Arg Leu Leu Tyr Ser Cys Phe Glu Ala Asp Leu Lys Gly Pro
        835                 840                 845

Asp Pro Glu Val Tyr Gln His Glu Ile Pro Gly Gly Gln Leu Thr Asn
850                 855                 860

Leu Leu Phe Gln Ala Gln Gln Leu Gly Leu Gly Glu Gln Trp Ala Glu
865                 870                 875                 880

Thr Lys Arg Ala Tyr Arg Glu Ala Asn Tyr Leu Leu Gly Asp Ile Val
            885                 890                 895

Lys Val Thr Pro Thr Ser Lys Val Val Gly Asp Leu Ala Gln Phe Met
        900                 905                 910

Val Ser Asn Lys Leu Thr Ser Asp Asp Ile Arg Arg Leu Ala Asn Ser
    915                 920                 925

Leu Asp Phe Pro Asp Ser Val Met Asp Phe Phe Glu Gly Leu Ile Gly
930                 935                 940

Gln Pro Tyr Gly Gly Phe Pro Glu Pro Leu Arg Ser Asp Val Leu Arg
945                 950                 955                 960

Asn Lys Arg Arg Lys Leu Thr Cys Arg Pro Gly Leu Glu Leu Glu Pro
            965                 970                 975

Phe Asp Leu Glu Lys Ile Arg Glu Asp Leu Gln Asn Arg Phe Gly Asp
        980                 985                 990

Ile Asp Glu Cys Asp Val Ala Ser Tyr Asn Met Tyr Pro Arg Val Tyr
    995                 1000                1005

Glu Asp Phe Gln Lys Ile Arg Glu Thr Tyr Gly Asp Leu Ser Val
    1010                1015                1020

Leu Pro Thr Lys Asn Phe Leu Ala Pro Ala Glu Pro Asp Glu Glu
    1025                1030                1035

Ile Glu Val Thr Ile Glu Gln Gly Lys Thr Leu Ile Ile Lys Leu
    1040                1045                1050

Gln Ala Val Gly Asp Leu Asn Lys Lys Thr Gly Gln Arg Glu Val
    1055                1060                1065

Tyr Phe Glu Leu Asn Gly Glu Leu Arg Lys Ile Arg Val Ala Asp
```

```
                    1070                1075                1080

Lys  Ser  Gln  Asn  Ile  Gln  Ser  Val  Ala  Lys  Pro  Lys  Ala  Asp  Val
          1085                1090                1095

His  Asp  Thr  His  Gln  Ile  Gly  Ala  Pro  Met  Ala  Gly  Val  Ile  Ile
          1100                1105                1110

Glu  Val  Lys  Val  His  Lys  Gly  Ser  Leu  Val  Lys  Lys  Gly  Glu  Ser
          1115                1120                1125

Ile  Ala  Val  Leu  Ser  Ala  Met  Lys  Met  Glu  Met  Val  Val  Ser  Ser
          1130                1135                1140

Pro  Ala  Asp  Gly  Gln  Val  Lys  Asp  Val  Phe  Ile  Lys  Asp  Gly  Glu
          1145                1150                1155

Ser  Val  Asp  Ala  Ser  Asp  Leu  Leu  Val  Val  Leu  Glu  Glu  Glu  Thr
          1160                1165                1170

Leu  Pro  Pro  Ser  Gln  Lys  Lys
          1175                1180

<210> SEQ ID NO 20
<211> LENGTH: 446
<212> TYPE: PRT
<213> ORGANISM: Saccharomyces cerevisiae

<400> SEQUENCE: 20

Met  Lys  Ile  Val  Val  Ile  Gly  Thr  Asn  His  Ala  Gly  Ile  Ala  Thr  Ala
1                 5                  10                 15

Asn  Thr  Leu  Leu  Glu  Gln  Tyr  Pro  Gly  His  Glu  Ile  Val  Met  Ile  Asp
                  20                 25                 30

Arg  Asn  Ser  Asn  Met  Ser  Tyr  Leu  Gly  Cys  Gly  Thr  Ala  Ile  Trp  Val
                  35                 40                 45

Gly  Arg  Gln  Ile  Glu  Lys  Pro  Asp  Glu  Leu  Phe  Tyr  Ala  Lys  Ala  Glu
         50                  55                 60

Asp  Phe  Glu  Ala  Lys  Gly  Val  Lys  Ile  Leu  Thr  Glu  Thr  Glu  Val  Ser
65                 70                 75                 80

Glu  Ile  Asp  Phe  Ala  Asn  Lys  Lys  Val  Tyr  Ala  Lys  Thr  Lys  Ser  Asp
                  85                 90                 95

Asp  Glu  Ile  Ile  Glu  Ala  Tyr  Asp  Lys  Leu  Val  Leu  Ala  Thr  Gly  Ser
                  100                105                110

Arg  Pro  Ile  Ile  Pro  Asn  Leu  Pro  Gly  Lys  Asp  Leu  Lys  Gly  Ile  His
                  115                120                125

Phe  Leu  Lys  Leu  Phe  Gln  Glu  Gly  Gln  Ala  Ile  Asp  Ala  Glu  Phe  Ala
         130                 135                140

Lys  Glu  Lys  Val  Lys  Arg  Ile  Ala  Val  Ile  Gly  Ala  Gly  Tyr  Ile  Gly
145                150                155                160

Thr  Glu  Ile  Ala  Glu  Ala  Ala  Lys  Arg  Arg  Gly  Lys  Glu  Val  Leu  Leu
                  165                170                175

Phe  Asp  Ala  Glu  Asn  Thr  Ser  Leu  Ala  Ser  Tyr  Tyr  Asp  Glu  Glu  Phe
                  180                185                190

Ala  Lys  Gly  Met  Asp  Glu  Asn  Leu  Ala  Gln  His  Gly  Ile  Glu  Leu  His
                  195                200                205

Phe  Gly  Glu  Leu  Ala  Lys  Glu  Phe  Lys  Ala  Asn  Glu  Glu  Gly  Tyr  Val
         210                 215                220

Ser  Gln  Ile  Val  Thr  Asn  Lys  Ala  Thr  Tyr  Asp  Val  Asp  Leu  Val  Ile
225                230                235                240

Asn  Cys  Ile  Gly  Phe  Thr  Ala  Asn  Ser  Ala  Leu  Ala  Ser  Asp  Lys  Leu
                  245                250                255
```

```
Ala Thr Phe Lys Asn Gly Ala Ile Lys Val Asp Lys His Gln Gln Ser
            260                 265                 270

Ser Asp Pro Asp Val Tyr Ala Val Gly Asp Val Ala Thr Ile Tyr Ser
        275                 280                 285

Asn Ala Leu Gln Asp Phe Thr Tyr Ile Ala Leu Ala Ser Asn Ala Val
    290                 295                 300

Arg Ser Gly Ile Val Ala Gly His Asn Ile Gly Gly Lys Glu Leu Glu
305                 310                 315                 320

Ser Val Gly Val Gln Gly Ser Asn Gly Ile Ser Ile Phe Gly Tyr Asn
                325                 330                 335

Met Thr Ser Thr Gly Leu Ser Val Lys Ala Ala Lys Lys Leu Gly Leu
            340                 345                 350

Glu Val Ser Phe Ser Asp Phe Glu Asp Lys Gln Lys Ala Trp Phe Leu
        355                 360                 365

His Glu Asn Asn Asp Ser Val Lys Ile Arg Ile Val Tyr Glu Thr Lys
    370                 375                 380

Ser Arg Arg Ile Ile Gly Ala Gln Leu Ala Ser Lys Ser Glu Ile Ile
385                 390                 395                 400

Ala Gly Asn Ile Asn Met Phe Ser Leu Ala Ile Gln Glu Lys Lys Thr
                405                 410                 415

Ile Asp Glu Leu Ala Leu Leu Asp Leu Phe Phe Leu Pro His Phe Asn
            420                 425                 430

Ser Pro Tyr Asn Tyr Met Thr Val Ala Ala Leu Asn Ala Lys
        435                 440                 445

<210> SEQ ID NO 21
<211> LENGTH: 356
<212> TYPE: PRT
<213> ORGANISM: Saccharomyces cerevisiae

<400> SEQUENCE: 21

Met Tyr Pro Thr Ser Gly Cys Ala Arg Val Leu Met Ala Cys Pro Ala
1               5                   10                  15

Pro Ala Met Leu Arg Gly Pro Leu Leu Arg Pro Ser Thr Thr Ala Ile
            20                  25                  30

Arg Gly Leu Arg Gly Ser Pro Leu Leu Tyr His Tyr Ala Ala Thr Ser
        35                  40                  45

Asn Ser Asn Met Arg Tyr Phe Ser Ser Thr Ser Arg Arg Trp Ile Lys
    50                  55                  60

Glu Phe Phe Ala Pro Pro Lys Glu Thr Asp His Ile Val Glu Ser Val
65                  70                  75                  80

Thr Thr Trp Lys His Pro Val Phe Thr Glu Lys Gln Met Lys Glu Ile
                85                  90                  95

Ala Ile Ala His Arg Glu Ala Lys Asn Trp Ser Asp Trp Val Ala Leu
            100                 105                 110

Gly Thr Val Arg Phe Leu Arg Trp Ala Thr Asp Leu Ala Thr Gly Tyr
        115                 120                 125

Arg His Ala Ala Pro Gly Lys Gln Gly Val Glu Val Pro Glu Gln Phe
    130                 135                 140

Gln Met Thr Glu Arg Lys Trp Val Ile Arg Phe Ile Phe Leu Glu Thr
145                 150                 155                 160

Val Ala Gly Val Pro Gly Met Val Gly Gly Met Leu Arg His Leu Arg
                165                 170                 175

Ser Leu Arg Arg Met Lys Arg Asp Asn Gly Trp Ile Glu Thr Leu Leu
            180                 185                 190
```

```
Glu Glu Ala Tyr Asn Glu Arg Met His Leu Leu Ser Phe Leu Lys Leu
        195             200             205

Ala Gln Pro Gly Trp Phe Met Arg Leu Met Val Leu Gly Ala Gln Gly
    210             215             220

Val Phe Phe Asn Gly Phe Phe Ile Ser Tyr Leu Ile Ser Pro Arg Thr
225             230             235             240

Cys His Arg Phe Val Gly Tyr Leu Glu Glu Glu Ala Val Met Thr Tyr
            245             250             255

Thr His Ala Ile Lys Asp Leu Glu Ser Gly Lys Leu Pro Asn Trp Ala
            260             265             270

Asn Gln Pro Ala Pro Asp Ile Ala Val Ala Tyr Trp Gln Met Pro Glu
    275             280             285

Gly Lys Arg Thr Ile Leu Asp Leu Leu Tyr Tyr Ile Arg Ala Asp Glu
    290             295             300

Ala Lys His Arg Glu Val Asn His Thr Leu Ala Asn Leu Lys Gln Gly
305             310             315             320

Val Asp Pro Asn Pro Tyr Ala Ala Lys Tyr Asp Asn Pro Glu Ala Pro
            325             330             335

His Pro Thr Lys Ser Ala Glu Ile Val Lys Pro Thr Gly Trp Glu Arg
            340             345             350

Asp Glu Val Ile
        355
```

UNITED STATES PATENT AND TRADEMARK OFFICE
CERTIFICATE OF CORRECTION

| | | |
|---|---|---|
| PATENT NO. | : 12,098,407 B2 | Page 1 of 1 |
| APPLICATION NO. | : 17/616843 | |
| DATED | : September 24, 2024 | |
| INVENTOR(S) | : Penelope R. Chua et al. | |

It is certified that error appears in the above-identified patent and that said Letters Patent is hereby corrected as shown below:

On the Title Page

Column 1, at Item (73) should read:
Assignee: Amyris, Inc., Emeryville, CA (US)

Signed and Sealed this
Nineteenth Day of November, 2024

Katherine Kelly Vidal
*Director of the United States Patent and Trademark Office*